(12) United States Patent
Goldeck et al.

(10) Patent No.: US 10,059,943 B2
(45) Date of Patent: Aug. 28, 2018

(54) RIG-I LIGANDS AND METHODS FOR PRODUCING THEM

(71) Applicant: RHEINISCHE FRIEDRICH-WILHELMS-UNIVERSITÄT BONN, Bonn (DE)

(72) Inventors: Marion Goldeck, Bonn (DE); Jasper Van Den Boorn, Bonn (DE); János Ludwig, Göttingen (DE); Christine Schuberth-Wagner, Siegburg (DE)

(73) Assignee: Rheinische Friedrich-Wilhelms-Universität Bonn, Bonn (DE)

( * ) Notice: Subject to any disclaimer, the term of this patent is extended or adjusted under 35 U.S.C. 154(b) by 439 days.

(21) Appl. No.: 14/431,859

(22) PCT Filed: Sep. 26, 2013

(86) PCT No.: PCT/EP2013/070117
§ 371 (c)(1),
(2) Date: Mar. 27, 2015

(87) PCT Pub. No.: WO2014/049079
PCT Pub. Date: Apr. 3, 2014

(65) Prior Publication Data
US 2016/0152983 A1     Jun. 2, 2016

(30) Foreign Application Priority Data

Sep. 27, 2012 (EP) .................................... 12186444

(51) Int. Cl.
| | | |
|---|---|---|
| C12N 15/113 | (2010.01) |
| C07H 21/00 | (2006.01) |
| C07H 21/02 | (2006.01) |
| A61K 9/00 | (2006.01) |
| C12N 15/11 | (2006.01) |
| C12N 15/117 | (2010.01) |

(52) U.S. Cl.
CPC .......... *C12N 15/113* (2013.01); *A61K 9/0021* (2013.01); *C07H 21/02* (2013.01); *C12N 15/111* (2013.01); *C12N 15/117* (2013.01); *C12N 15/1137* (2013.01); *C12N 2310/17* (2013.01); *C12N 2310/315* (2013.01); *C12N 2310/321* (2013.01); *C12N 2310/3513* (2013.01); *C12N 2310/3515* (2013.01); *C12N 2310/3517* (2013.01); *C12N 2310/3527* (2013.01); *C12N 2310/3533* (2013.01); *C12N 2320/32* (2013.01)

(58) Field of Classification Search
CPC .............................. C12N 15/113; C07H 21/02
USPC ................ 536/23.1; 514/42, 43, 44 A, 44 R
See application file for complete search history.

(56) References Cited

U.S. PATENT DOCUMENTS

| | | | |
|---|---|---|---|
| 3,534,017 | A | 10/1970 | Fujimoto et al. |
| 4,210,746 | A | 7/1980 | Kerr et al. |
| 4,522,811 | A | 6/1985 | Eppstein et al. |
| 5,166,195 | A | 11/1992 | Ecker |
| 5,194,428 | A | 3/1993 | Agrawal et al. |
| 5,264,423 | A | 11/1993 | Cohen et al. |
| 5,271,941 | A | 12/1993 | Cho-Chung |
| 5,292,875 | A | 3/1994 | Stec et al. |
| 5,366,878 | A | 11/1994 | Pederson et al. |
| 5,606,049 | A | 2/1997 | Vaghefi |
| 5,635,377 | A | 6/1997 | Pederson et al. |
| 5,644,048 | A | 7/1997 | Yau |
| 5,646,267 | A | 7/1997 | Stec et al. |
| 5,652,355 | A | 7/1997 | Metelev et al. |
| 5,736,294 | A | 4/1998 | Ecker et al. |
| 5,770,713 | A | 6/1998 | Imbach et al. |
| 6,143,881 | A | 11/2000 | Metelev et al. |
| 6,344,323 | B1 | 2/2002 | Seifert |
| 6,346,614 | B1 | 2/2002 | Metelev et al. |
| 6,369,209 | B1 | 4/2002 | Manoharan et al. |
| 6,737,520 | B2 | 5/2004 | Mohan et al. |
| 6,900,308 | B2 | 5/2005 | Wyrzykiewicz et al. |
| 7,119,184 | B2 | 10/2006 | Manoharan et al. |
| 7,217,807 | B2 | 5/2007 | Bentwich |
| 7,285,658 | B2 | 10/2007 | Cook et al. |
| 7,371,735 | B2 | 5/2008 | Harel-Bellan et al. |
| 7,598,230 | B2 | 10/2009 | Cook et al. |
| 7,696,334 | B1 | 4/2010 | Bentwich |
| 7,696,342 | B1 | 4/2010 | Bentwich |
| 7,759,478 | B1 | 7/2010 | Bentwich |
| 7,790,867 | B2 | 9/2010 | Bentwich |
| 7,807,653 | B2 | 10/2010 | Cook et al. |
| 7,862,816 | B2 | 1/2011 | Krasnoperov et al. |
| 8,563,709 | B2 | 10/2013 | Iba et al. |
| 8,912,158 | B2 | 12/2014 | Dimmeler et al. |

(Continued)

FOREIGN PATENT DOCUMENTS

| | | |
|---|---|---|
| CN | 1434054 A | 8/2003 |
| CN | 101088565 A | 12/2007 |

(Continued)

OTHER PUBLICATIONS

Chawla-Sarkar et al., "Apoptosis and interferons: Role of interferon-stimulated genes as mediators of apoptosis", Apoptosis, 2003, 8(3), pp. 237-249.

(Continued)

*Primary Examiner* — Jezia Riley
(74) *Attorney, Agent, or Firm* — Rothwell, Figg, Ernst & Manbeck, P.C.

(57) ABSTRACT

The present invention relates to new triphosphate-modified oligonucleotides which may act as RIG-I ligands as well as a new method allowing the synthesis and purification in high yield and purity suitable for pharmaceutical applications.

17 Claims, 24 Drawing Sheets

Specification includes a Sequence Listing.

(56) References Cited

U.S. PATENT DOCUMENTS

| | | |
|---|---|---|
| 2003/0129615 A1 | 7/2003 | Wyrzykiewicz et al. |
| 2003/0171570 A1 | 9/2003 | Schweitzer |
| 2003/0203868 A1 | 10/2003 | Bushman |
| 2004/0059104 A1 | 3/2004 | Cook et al. |
| 2004/0234999 A1 | 11/2004 | Farrar et al. |
| 2004/0261149 A1 | 12/2004 | Fauquet et al. |
| 2005/0026861 A1 | 3/2005 | Kandimalla et al. |
| 2005/0182005 A1 | 8/2005 | Tuschl et al. |
| 2005/0222060 A1 | 10/2005 | Bot et al. |
| 2005/0249736 A1 | 11/2005 | Krasnoperov et al. |
| 2006/0035815 A1 | 2/2006 | Chen et al. |
| 2006/0178334 A1 | 8/2006 | Rossi et al. |
| 2007/0066521 A1 | 3/2007 | Fauquet |
| 2007/0259832 A1 | 11/2007 | Cook et al. |
| 2007/0265220 A1 | 11/2007 | Rossi et al. |
| 2007/0265224 A1 | 11/2007 | Cook et al. |
| 2007/0287681 A1 | 12/2007 | Jeong et al. |
| 2008/0171712 A1 | 7/2008 | Kandimalla et al. |
| 2008/0188428 A1 | 8/2008 | Bentwich |
| 2008/0250532 A1 | 10/2008 | Abdullah et al. |
| 2009/0143327 A1 | 6/2009 | Smolke et al. |
| 2009/0203121 A1 | 8/2009 | Hochberg et al. |
| 2009/0203131 A1 | 8/2009 | Reineke et al. |
| 2009/0203894 A1 | 8/2009 | Liu et al. |
| 2010/0178272 A1 | 7/2010 | Hartmann |
| 2010/0260788 A1 | 10/2010 | Debelak et al. |
| 2010/0303859 A1 | 12/2010 | Williams |
| 2011/0130738 A1 | 6/2011 | Schmidt |
| 2011/0165133 A1 | 7/2011 | Rabinovich et al. |
| 2011/0245481 A1 | 10/2011 | Iba et al. |
| 2011/0247091 A1 | 10/2011 | Magor et al. |
| 2012/0225924 A1 | 9/2012 | Lin et al. |
| 2013/0121989 A1 | 5/2013 | Gaertig et al. |
| 2013/0189367 A1 | 7/2013 | Zhang et al. |
| 2013/0302252 A1 | 11/2013 | Zhang et al. |
| 2014/0171368 A1 | 6/2014 | Goepferich et al. |
| 2015/0018407 A1 | 1/2015 | Dimmeler et al. |

FOREIGN PATENT DOCUMENTS

| | | |
|---|---|---|
| CN | 101190944 A | 6/2008 |
| CN | 101632833 A | 1/2010 |
| CN | 101974529 A | 2/2011 |
| CN | 102475892 A | 5/2012 |
| DE | 1 695 303 A1 | 4/1972 |
| DE | 41 10 085 A1 | 10/1992 |
| DE | 10 2007 052 114 A1 | 5/2009 |
| EP | 0 021 099 A1 | 1/1981 |
| EP | 0 031 285 A2 | 7/1981 |
| EP | 0 043 075 A2 | 1/1982 |
| EP | 0 081 099 A2 | 6/1983 |
| EP | 0 339 842 A2 | 11/1989 |
| EP | 0 386 563 A1 | 9/1990 |
| EP | 0 415 901 A2 | 3/1991 |
| EP | 0 698 034 B1 | 2/1996 |
| EP | 0 754 188 B1 | 11/1997 |
| EP | 0 788 366 B1 | 12/1999 |
| EP | 0 739 899 B1 | 6/2001 |
| EP | 1 247 815 A2 | 10/2002 |
| EP | 1 493 818 A2 | 1/2005 |
| EP | 1 505 152 A1 | 2/2005 |
| EP | 1 626 086 A2 | 2/2006 |
| EP | 1 637 597 A1 | 3/2006 |
| EP | 1 657 306 A1 | 5/2006 |
| EP | 1 743 901 A2 | 1/2007 |
| EP | 5020019.5 A1 | 3/2007 |
| EP | 5020020.3 A1 | 3/2007 |
| EP | 05 020 019.5 A1 | 12/2007 |
| EP | 05 020 020.3 A1 | 12/2007 |
| EP | 06 016 578.4 A1 | 12/2007 |
| EP | 6016578.4 A1 | 2/2008 |
| EP | 1 939 291 A2 | 7/2008 |
| EP | 2 113 565 A1 | 11/2009 |
| EP | 2 141 234 A1 | 1/2010 |
| EP | 2 207 797 A1 | 7/2010 |
| EP | 1 453 962 B1 | 8/2010 |
| EP | 2 213 738 A2 | 8/2010 |
| EP | 2 284 266 A2 | 2/2011 |
| EP | 2 327 783 A1 | 6/2011 |
| EP | 2 338 449 A1 | 6/2011 |
| EP | 2 338 499 A1 | 6/2011 |
| EP | 1 857 119 B1 | 11/2011 |
| EP | 2 277 508 B1 | 4/2012 |
| EP | 1 969 125 B1 | 6/2012 |
| EP | 2 497 827 A1 | 9/2012 |
| EP | 2 123 757 B1 | 10/2012 |
| EP | 2 508 530 A1 | 10/2012 |
| EP | 2 514 758 A1 | 10/2012 |
| EP | 2 518 150 A2 | 10/2012 |
| EP | 2508530 A1 | 10/2012 |
| EP | 1 920 775 B1 | 12/2012 |
| EP | 2 551 354 A1 | 1/2013 |
| EP | 1 915 448 B1 | 9/2013 |
| EP | 2 671 949 A1 | 12/2013 |
| EP | 1 957 648 B1 | 4/2014 |
| EP | 1 973 574 B1 | 4/2014 |
| EP | 2 712 870 A1 | 4/2014 |
| EP | 2 069 500 B1 | 9/2014 |
| EP | 2 207 787 B1 | 11/2014 |
| EP | 2 492 355 B1 | 4/2015 |
| JP | 0H6-501843 A | 3/1994 |
| JP | H6-501843 A | 3/1994 |
| JP | 07-099976 A | 4/1995 |
| JP | 08-154687 A | 6/1996 |
| JP | 2003-535043 A | 11/2003 |
| JP | 2005-526778 A | 9/2005 |
| JP | 2006-238795 A | 9/2006 |
| WO | WO 84/00688 A1 | 3/1984 |
| WO | WO 89/08146 A1 | 9/1989 |
| WO | WO 90/14353 A1 | 11/1990 |
| WO | WO 1991/006309 A1 | 5/1991 |
| WO | WO 92/02641 A1 | 2/1992 |
| WO | WO 92/03454 A1 | 3/1992 |
| WO | WO 92/17484 A1 | 10/1992 |
| WO | WO 93/07882 A1 | 4/1993 |
| WO | WO 93/08296 A1 | 4/1993 |
| WO | WO 93/23569 A1 | 11/1993 |
| WO | WO 94/02501 A1 | 2/1994 |
| WO | WO 94/15619 A1 | 7/1994 |
| WO | WO 94/17093 A1 | 8/1994 |
| WO | WO 94/24144 A2 | 10/1994 |
| WO | WO 94/26764 A1 | 11/1994 |
| WO | WO 95/03406 A2 | 2/1995 |
| WO | WO 95/32719 A1 | 12/1995 |
| WO | WO 96/02556 A2 | 2/1996 |
| WO | WO 96/07392 A2 | 3/1996 |
| WO | WO 1996/18736 A2 | 6/1996 |
| WO | WO 1996/19572 A1 | 6/1996 |
| WO | WO 96/040159 A1 | 12/1996 |
| WO | WO 96/041812 A1 | 12/1996 |
| WO | WO 99/55857 A2 | 11/1999 |
| WO | WO 00/66609 A1 | 11/2000 |
| WO | WO 01/16312 A2 | 3/2001 |
| WO | WO 2001/022990 A2 | 5/2001 |
| WO | WO 01/068077 A2 | 9/2001 |
| WO | WO 01/70751 A1 | 9/2001 |
| WO | WO 2001/068077 A2 | 9/2001 |
| WO | WO 02/10432 A2 | 2/2002 |
| WO | WO 03/008432 A1 | 1/2003 |
| WO | WO 2003/008432 A1 | 1/2003 |
| WO | WO 03/012052 A2 | 2/2003 |
| WO | WO 03/072757 A2 | 9/2003 |
| WO | WO 03/078595 A2 | 9/2003 |
| WO | WO 03/086280 A2 | 10/2003 |
| WO | WO 03/087367 A2 | 10/2003 |
| WO | WO 03/087368 A2 | 10/2003 |
| WO | WO 03/101375 A2 | 12/2003 |
| WO | WO 2003/101375 | 12/2003 |
| WO | WO 2004/015062 A2 | 2/2004 |
| WO | 2004/022777 A1 | 3/2004 |
| WO | WO 2004/020631 A2 | 3/2004 |
| WO | WO 2004/024063 A2 | 3/2004 |
| WO | WO 2004/044123 A2 | 5/2004 |
| WO | WO 2004/045543 A2 | 6/2004 |

(56) References Cited

FOREIGN PATENT DOCUMENTS

| | | |
|---|---|---|
| WO | WO 2004/048511 A2 | 6/2004 |
| WO | WO 2004/061423 A2 | 7/2004 |
| WO | WO 2004/074441 A2 | 9/2004 |
| WO | WO 2004/080418 A2 | 9/2004 |
| WO | WO 2004/080425 A2 | 9/2004 |
| WO | WO 2004/083430 A2 | 9/2004 |
| WO | WO 2004/085623 A2 | 10/2004 |
| WO | WO 2004/106517 A1 | 12/2004 |
| WO | WO 2004/111190 A2 | 12/2004 |
| WO | WO 2005/005632 A2 | 1/2005 |
| WO | WO 2005/076979 A2 | 8/2005 |
| WO | WO 2005/089287 A2 | 9/2005 |
| WO | WO 2005/108573 A2 | 11/2005 |
| WO | WO 2005/117991 A2 | 12/2005 |
| WO | WO 2006/016574 A1 | 2/2006 |
| WO | WO 2006/063252 A2 | 6/2006 |
| WO | WO 2006/074400 A2 | 7/2006 |
| WO | WO 2006/078646 A2 | 7/2006 |
| WO | WO 2006/105361 A2 | 10/2006 |
| WO | WO 2006/110813 A2 | 10/2006 |
| WO | WO 2006/119643 A1 | 11/2006 |
| WO | WO 2006/122409 A1 | 11/2006 |
| WO | WO 2006/128739 A1 | 12/2006 |
| WO | WO 2006/130949 A1 | 12/2006 |
| WO | WO 2007/021142 A1 | 2/2007 |
| WO | WO 2007/030619 A2 | 3/2007 |
| WO | WO 2007/031319 A1 | 3/2007 |
| WO | WO 2007/031322 | 3/2007 |
| WO | WO 2007/038788 A2 | 4/2007 |
| WO | WO 2007/051303 A1 | 5/2007 |
| WO | WO 2007/107304 A2 | 9/2007 |
| WO | WO 2008/017473 A2 | 2/2008 |
| WO | WO 2008/045576 A2 | 4/2008 |
| WO | WO 2008/076127 A1 | 6/2008 |
| WO | 2008077600 A1 | 7/2008 |
| WO | WO 2008/080091 A2 | 7/2008 |
| WO | WO 2008/087641 A2 | 7/2008 |
| WO | WO 2008/087642 A2 | 7/2008 |
| WO | WO 2008/099396 A1 | 8/2008 |
| WO | WO 2008/124165 A2 | 10/2008 |
| WO | WO 2008/131807 A2 | 11/2008 |
| WO | WO 2008/134593 A1 | 11/2008 |
| WO | 2009014612 A2 | 1/2009 |
| WO | WO 2009/018500 A1 | 2/2009 |
| WO | WO 2009/038707 A2 | 3/2009 |
| WO | WO 2009/046541 A1 | 4/2009 |
| WO | WO 2009/051659 A2 | 4/2009 |
| WO | 2009060281 A2 | 5/2009 |
| WO | WO 2009/056116 A1 | 5/2009 |
| WO | WO 2009/060124 A2 | 5/2009 |
| WO | WO 2009/060281 A2 | 5/2009 |
| WO | WO 2009/061417 A1 | 5/2009 |
| WO | WO 2009/064590 A2 | 5/2009 |
| WO | WO 2009/068677 A1 | 6/2009 |
| WO | WO 2009/083738 A2 | 7/2009 |
| WO | WO 2009/141146 A1 | 11/2009 |
| WO | WO 2009/146556 A1 | 12/2009 |
| WO | WO 2009/151600 A2 | 12/2009 |
| WO | WO 2010/028079 A2 | 3/2010 |
| WO | WO 2010/042742 A2 | 4/2010 |
| WO | WO 2010/042749 A2 | 4/2010 |
| WO | WO 2010/042751 A2 | 4/2010 |
| WO | WO 2010/042755 A2 | 4/2010 |
| WO | WO 2010/047216 A1 | 4/2010 |
| WO | WO 2010/062502 A1 | 6/2010 |
| WO | WO 2010/099161 A1 | 9/2010 |
| WO | WO 2010/118263 A1 | 10/2010 |
| WO | WO 2010/120874 A2 | 10/2010 |
| WO | WO 2010/136192 A1 | 12/2010 |
| WO | WO 2010/147655 A2 | 12/2010 |
| WO | WO 2011/008857 A1 | 1/2011 |
| WO | WO 2011/011716 A1 | 1/2011 |
| WO | 2011028218 A1 | 3/2011 |
| WO | WO 2011/028218 A1 | 3/2011 |
| WO | WO 2011/064130 A1 | 6/2011 |
| WO | WO 2011/133559 A2 | 10/2011 |
| WO | WO 2011/138328 A2 | 11/2011 |
| WO | WO 2011/140285 A2 | 11/2011 |
| WO | WO 2012/056449 A2 | 5/2012 |
| WO | WO 2012/056457 A2 | 5/2012 |
| WO | WO 2012/091523 A2 | 7/2012 |
| WO | WO 2012/125987 A2 | 9/2012 |
| WO | 2012130886 A1 | 10/2012 |
| WO | WO 2012/130886 A1 | 10/2012 |
| WO | WO 2013/003887 A1 | 1/2013 |
| WO | WO 2013/013820 A1 | 1/2013 |
| WO | WO 2013/020986 A1 | 2/2013 |
| WO | WO 2013/053480 A1 | 4/2013 |
| WO | WO 2013/053481 A1 | 4/2013 |
| WO | WO 2013/075140 A1 | 5/2013 |
| WO | WO 2013/153082 A1 | 10/2013 |
| WO | WO 2014/049079 A1 | 4/2014 |
| WO | WO 2014/124433 A1 | 8/2014 |

OTHER PUBLICATIONS

Scheel et al., "Toll-like receptor-dependent activation of several human blood cell types by protamine-condensed mRNA", Eur. J. Immunol, 2005, 35: pp. 1557-1566.
Sledz et al., "RNA interference in biology and disease", Blood, 2005, 106(3), pp. 787-794.
Absher, et al., Nature 223:715-717 (Aug. 16, 1969).
Adam, et al., Blood, 106(1):338-344 (2005).
Adelfinskaya, et al., Angew. Chem. Int. Ed., 46:4356-4358 (2007).
Adelfinskaya, et al., Nucleic Acids Research, 35(15):5060-5072 (2007).
Aigner, et al., J. Biomed. Biotechnol.2006(4):71659 (2006).
Akira, et al., C R Biol. 327(6):581-9 (2004).
Aleman, et al., RNA 13(3):385-395 (Mar. 2007).
Alexopoulou, et al., Nature, 413(6857):732-8 (2001).
Ambion, Life Technologies Corporation, Catalog Nos. AM 1330, AM1333, AM1334, AM1338, Publ. No. 1330M, Revision G. (2012).
Andrejeva, et al., Proc Natl Acad Se; USA, 101:17264-9 (Dec. 7, 2004).
Arnold, et al., J.Biol.Chem., 274(5):1706-2716 (1999).
Barton, et al., Nat Immunol 7:49-56 (Jan. 2006).
Bartonschlager, et al., J. Gen. Virol., 81:1631-1648 (2000).
Bass, et al., Cell 55(6):1089-98 (1988).
Baudin, et al., EMBO J., 13(13):3158-3166 (1994).
Behlke, et al., Mol Ther, 13(4):644-670 (Apr. 2006).
Bekeredjian-Ding, et al., J Immunol ,174: 4043-50 (Apr. 1, 2005).
Besch, et al., Cell Death Differ, 14:818-29 (2007).
Blackburn, et al., J.C.S. Chem. Commun., 1188-1190 (1981).
Blumberg, et al., Cell, 23(3):837-45 (Mar. 1981).
Blumberg, et al., J Virol., 40(2):568-76 (Nov. 1981).
Bonin, et al., RNA, 6:563-570 (2000).
Bowie, et al., Trends in Immunology, 28(4):147-150 (2007).
Brownlee, et al., Nucleic Acids Research, 23(14):2641-2647 (1995).
Brzozka, et al. Journal of Virology, 80:2675-83 (Mar. 2006).
Brzozka, et al., Journal of Virology, 79:7673-81 (Jun. 2005).
Bui et al., Curr. Opin. Immunol., 19:203-8 (2007).
CA 2589406; Alnylam Pharmaceuticals, Inc.; Publ. Jun. 15, 2006.
Carroll, et al. Methods in Enzymology, 275:365-382 (1996).
Cazenave, et al., Proc. Natl. Acad. Sci. USA, 91:6672-6976 (1994).
Chang et al., Microbes and Infection 8, 157 (2006).
Chaperot, et al., The Journal of Immunology, 176:248-255 (2006).
Chawla-Sarkar, et al., Cell Death and Differentiation, 11:915-923 (2004).
Chemicool, "Definition of Homogeneous," in Chemicool (2014). Retrieved on Jan. 25, 2015 from www.chemicool.com/definition/homogeneous.html.
Chen, et al., J Virol., 81(2):964-76 (2007).
Cheong, et al., Nucleic Acids Res, 24(21):4197-4201 (D35) (1996).
Chien, et al., Cancer Gene Therapy, 12(3):321-328 (2005).
Chiocca, Nat Rev Cancer, 2:938-950 (2002).
Coe, et al., J. Chem. Soc., Chem. Commun., 312-314 (1991).
Coffey, et al., Science, 282:1332-1334 (1998).

(56) References Cited

OTHER PUBLICATIONS

Colonno, et al., *Cell*, 15:93-101 (1978).
Cuesta, *J Immunol.*, 178(6):3602-11 (2007).
Cui, et al. *Molecular Cell*, 29:169-179 (2008).
Cullen, *Mol Cell*, 16:861-5 (Dec. 22, 2004).
Curiel, *J. Clin. Invest.*, 117:1167-74 (2007).
Danial, et al., *Cell*, 116:205-19 (2004).
Davis, et al., *PNAS*, 101(29):10697-10702 (Jul. 20, 2004).
De Fougerolles, et al., *J. Nat.Rev.Drug Discov.*, 6:443-53 (2007).
De Jonge, et al., *Gene Therapy*, 13:400-411 (2006)).
Decatur, et al., *J. Biol. Chem.*, 278:695-8 (Jan. 3, 2003).
Delale, et al., *J Immunol*, 175:6723-32 (Nov. 15, 2005).
Der, et al, *Proc Natl Acad Sci USA*, 92:8841-5 (Sep. 12, 1995).
Diebold, et al., *Nature*, 424:324-8 (Jul. 17, 2003).
Diebold, et al., *Science*, 303:1529-31 (Mar. 5, 2004).
Duan, et al., *Antiviral Therapy*, 13(1):109-114 (2008).
Dunn, et al., *J Mol Biol*, 166:477-535 (Jun. 5, 1983).
Elbashir, et al., *Nature*, 411:494-498 (May 24, 2001).
Elbashir, et al., *The EMBO Journal*, 20(23):6877-6888 (2001).
Entry "influenca A virus" in Wikipedia.
Entry "Oligonucleotide synthesis" in Wikipedia.
Fromont-Racine, et al., *Gene*, 313:17-42 (Aug. 14, 2003).
Furuichi, et al., *Adv Virus Res*, 55:135-84 (2000).
Gaur, et al., *Tetrahedron Letters*, 33:3301-3304 (1992).
GenBank Acc No. AF389115.1 (Sep. 19, 2002) Influenza A virus (A/Puerto Rico/8/34/Mount Sinai (H1N1», segment 1, complete sequence (see first nucleotide, Pos. 1) (D15).
GenBank Acc No. AF389116.1 (Sep. 19, 2002) Influenza A virus (A/Puerto Rico/8/34/Mount Sinai (H1N1)), segment 2, complete sequence (see first nucleotide, Pos. 1) (D16).
GenBank Acc No. AF389117.1 (Sep. 19, 2002) Influenza A virus (A/Puerto Rico/8/34/Mount Sinai (H1N1)), segment 3, complete sequence (see first nucleotide, Pos. 1) (D17).
GenBank Acc No. AF389118.1 (Sep. 19, 2002) Influenza A virus (A/Puerto Rico/8/34/Mount Sinai (H1N1)), segment 4, complete sequence (see first nucleotide, Pos. 1) (D18).
GenBank Acc No. AF389119.1 (Sep. 19, 2002) Influenza A virus (A/Puerto Rico/8/34/Mount Sinai (H1N1)), segment 5, complete sequence (see first nucleotide, Pos. 1) (D19).
GenBank Acc No. AF389120.1 (Sep. 19, 2002) Influenza A virus (A/Puerto Rico/8/34/Mount Sinai (H1N1)), segment 6, complete sequence (see first nucleotide, Pos. 1) (D20).
GenBank Acc No. AF389121.1 (Sep. 19, 2002) Influenza A virus (A/Puerto Rico/8/34/Mount Sinai (H1N1)), segment 7, complete sequence (see first nucleotide, Pos. 1) (D21).
GenBank Acc No. AF389122.1 (Sep. 19, 2002) Influenza A virus (A/Puerto Rico/8/34/Mount Sinai (H1N1)), segment 8, complete sequence (see first nucleotide, Pos. 1) (D22).
GenBank Acc. No. AF221499.1 (Mar. 9, 2001) Japanese encephalitis virus, isolate CH2195LA, complete genome (see first nucleotide, Pos. 1) (D14).
GenBank Acc. No. J02428.1 (Oct. 21, 2002) Vesicular stomatitis Indiana virus, complete genome (see first nucleotide, Pos. 1) (D13).
Gerber, et al., *Trends Biochem Sci*, 26(6):376-84 (2001).
Gerrits, digital dissertation, FU Berlin, 2001, English Abstract.
Gitlin, et al., *Proc Natl Acad Sci USA*, 103(22):8459-64 (2006).
Goldeck, et al., *Angew. Chem.*, 126(4):782-786 (2014).
Gondai, et al., *Nucleic Acids Res*, 36(3):e18 (2008).
Grzelinski, et al., *Hum Gene Ther.*, 17(7):751-66 (2005).
Haas, et al., *Immunity*,28:315-232 (2008).
Hanahan, et al., *Cell*, 100:57-70 (2000).
Hartmann, et al., *Handbook of RNA Biochemistry*, pp. 6, 39, 43 (2005).
Heil, et al., *Science*, 303:526-9 (Mar. 5, 2004).
Helm, et al., *RNA*, 1999, vol. 5, p. 618-621.
Hemmi, et al., *Nat Immunol*, 3:196 (Feb. 2002).
Hemmi, et al., *Nature*, 408:740-5 (Dec. 7, 2000).
Henry, et al., *J Exp Med* 204(5):987-94 (2007).
Hofacker, et al., *Bioinformatics*, 20:1495-1499 (2004).
Holý, et al., *Collect. Czech. Commun.*, 47:3447-3463 (1982).
Honda, et al., *Virus Res*, 55: 199-206 (Jun. 1998).
Hornung, et al., *J Immunol*, 168:4531-7 (May 1, 2002).
Hornung, et al, *Nat Med*, 11(3):263-70 (Mar. 2005).
Hornung, et al. *Science*, 314:994-7 (2006).
Hsu, et al., *Croc.Natl.Acad.Sci.U.S.A.*, 84:8140-8141 (1987).
Huang, et al., *Biochemistry*, 39 (50):15548-15555 (2000).
Ishii, et al., *Nat Immunol*, 7:40-8 (Jan. 2006).
Jiang, et al., *Genes & Dev*, 17:832-837 (2003).
Judge, et al., *Nat Biotechnol*, 23:457-462 (2005).
Kamphuis, et al., *Blood*, 108:3253-61 (2006).
Kanneganti, et al. *Nature*, 440 (7081):233-6 (2006).
Kao, et al., *Virology*, 287:251-260 (2001).
Kariko, et al., *Biochem. Biophys. Res. Commun.*, 128(2):695-698 (1985).
Kariko, et al., *Immunity*, 23:165-75 (Aug. 2005).
Kato, et al., *Immunity*, 23(1):19-28 (Jul. 2005).
Kato, et al., *Nature*, 441 (7089):101-105 (Apr. 9, 2006).
Kawai, et al., *Nat Immunol*, 6(10):981-988 (Oct. 2005).
Kawai, et al., *Nat Immunol*, 7(2):131-7 (2006).
Kennedy, et al., *J.Mol.Biol.*, 370:256-268 (2007).
Khan, et al., *J Drug Target*, 12(6):393-404 (2004).
Kim, et al., *Nat Biotechnol*, 22:321-325 (Mar. 2004).
Knorre, et al., *FEBS Letters*, 70(1):105-108 (1976).
Koh, et al., *J. Med. Chem.*, 48:2867-2875 (2005).
Kossen, et al. *Chemistry and Biology*, 11:807-815 (2004).
Krieg, *Annu Rev Immunol*, 20:709-60 (2002).
Krieg, et al., *Nature*, 374:546-9 (Apr. 6, 1995).
Krug, et al., *Eur J Immunol*, 31:2154-63 (Jul. 2001).
Krug, et al., *Immunity*, 21:107-19 (Jul. 2004).
Krupp, *Gene*, 72:75-89 (1988).
Kuzmine, et al., *The Journal of Biol. Chem.*, 278(5):2819-2823 (2003).
Latz, et al., *Nat Immunol*, 5 (2):190-8 (2004).
Latz, et al., *Nat. Immunol*, 8:772-779 (2007).
Lau, et al. *J Exp Med*, 202 (9):1171-7 (2005).
Lebedev, et al., *Nucleosides, Nucleotides and Nucleic Acids*, 20(4-7):1403-1409 (2001).
Lee, et al., *Proc Natl Acad Sci USA*, 74:59-63 (Jan. 1977).
Limbach, et al., *Nucleic Acids Res*, 22:2183-2196 (1994).
Loo, et al., *J Virol*, 82:335-345 (2008).
Lu, et al., *Nucleic Acids Res*, 39(4):1565-1575 (Mar. 2011).
Ludwig, *Acta Biochim Biophys Acad Sci Hung*, 16:131-3 (1981).
Ludwig, et al., *J. Org Chem.*, 54:631-635 (1989).
Ludwig, et al., *J. Org. Chem.*, 56:1777-1783-D9 (1991).
Ma, et al., *Molecular Therapy—Nucleic Acids*, 3(e161):1-11 (2014).
Maitra, et al., *PNAS*, 77(7):3908-3911 (1980).
Marques, et al., *Nat Biotechnol*, 24(5):559-565 (May 2006).
Matsumoto, et al., *J Immunol*, 171(6):3154-62 (2003).
McGill, et al., *Cell*, 109:707-18 (2002).
Meister, et al., *Mol Cell*, 15:185 (Jul. 23, 2004).
Melchjorsen, et al., *J Virol*, 79:12944-51 (2005).
Meyer, et al., *Methods in Molecular Biol*, 1086:21-40 (2014).
Meylan, et al., *Nature*, 437(7062):1167-72 (Oct. 20, 2005).
Miller, et al., *N.Engl.J.Med*. 355:51-65 (2006).
Milligan, et al., *Dep.of Chem. And Biochem.*, 15(21):8783-98 (1987).
Milligan, et al., *Methods in Enzymology, RNA Processing*, Part A General Methods, p. 51-62 (1987).
Minakuchi, et al., *Nucleic Acids Research*, 32(13):e109 (2004).
Mocikat, et al., *Immunity*, 19:516-569 (Oct. 2003).
Muller, et al., *Science*, 264:1918-21 (1994).
Neumann, et al., *Curr. Topics in-Microbiol. and Immunol.*, 283:121-43 (2004).
Nishiya, et al, *J Biol Chem*, 279(18):19008-17 (2004).
Obeid, et al., *Nat.Med.*, 13:54-61 (2007).
Olsen, et al., *Journal of Biological Chemistry*, 271(13):7435-7439 (1996).
Palladino, et al., *Cell*, 102(4):437-49 (2000).
Paul, et al. *Chemistry and Biology*, 13:329-338 (2006).
Pearse, et al., *Adv Drug Deliv Rev*, 57(3):465-474 (Jan. 10, 2005).
Pei et al., *Nat. Methods*, 3:670-6 (2006).
Peterli, et al., *Helvetica Chimica Acta*, 75:696-706 (1992).
Phuangsab, et al., *Cancer Lett*, 172:27-36 (2001).

(56) References Cited

OTHER PUBLICATIONS

Pichelmair, et al., *Science*, 314:997-1001 (2006).
Plumet, et al., *PLoS One*, 3(e279):1-10 (2007).
Poeck, et al., *Blood*, 103(8):3058-3064 (Apr. 2004) (www.bloodjournal.org/cgi/content/full/103/8/3058#REF4).
Poeck, et al., *Nature Medicine*, 14(11):1256-1262 (2008).
Portela, et al., *J. Gen. Virol.*, 2992(83):723-734 (2002).
Radecke, et al., *EMBO J*, 14:5773-84 (Dec. 1, 1995).
Ranjith-Kumar, et al., *J. Virol.*, 76(24):12526-12536 (2002).
Ranjith-Kumar, et al., *RNA*, 12:303-312 (2006).
Reynolds, et al., *Nat Biotechnol*, 22:326-30 (2004).
Roempp, Sequenzhomologie, Georg Thieme Verlag KG, https://roempp.thieme.de/roempp4.0/do/data/RD-19.01964.
Rohayem, et al., *Journal of Virology*, 80(14):7060-7069 (2006).
Rosa, et al., *Molecular and Cellular Biology*, 1(9):785-796 (Sep. 1981).
Rossi, *Gene Therapy* 13:583-584 (2006).
Rothenfusser, et al., *J•Immunol*, 175:5260-8 (Oct. 15, 2005).
Rozenski, et al., *Nucleic acids research*, 27:196-97 (Jan. 1, 1999).
Rubin, et al, *Lancet*, 369:1731-41 (2007).
Rudd, et al., *J Immunol*, 176:1937-42 (Feb. 1, 2006).
Russell, *Cancer Gene Ther*, 9:961-966 (2002).
Samanta, et al., *The EMBO Journal*, 25:4207-4214 ( Aug. 2006).
Schlee, et al., *Immunity*, 31:25-34 (2009).
Schlee, et al., *CTMI*, 316:207-230 (2007).
Schlee, et al., *Mol Ther*, 18(7):1254-1262 (2010).
Schlee, et al., *Molecular Therapy*, 14(4):463-470 (2006).
Schmidt, et al., *PNAS*, 106(29):12067-12072 (2009).
Schnell, et al., *EMBO J*, 13(18):4195-4203 (1994).
Schoatzau, et al., *Chem. Commun.*, 3:387-388 (1996).
Selisko, et al., *Virology*, 351(1):145-158 (2006).
Seth, et al., *Cell*, 122(5):669-82 (Sep. 9, 2005).
Shatkin, et al., *Nat Struct Biol*, 7(10):838-42 (Oct. 2000).
Singh, et al., *PNAS USA*, 86:8280-3 (Nov. 1989).
Sioud, *Advanced Drug Delivery Reviews*, 59(2-3):153-163 (2007).
Sioud, et al., *Biochem Biophys Res Commun*, 312(4):1220-1225 (2003).
Sioud, et al., *J Mol Biol*, 348:1079-1090 (2005).
Sioud, *Eur J Immunol*, 36(5):1222-30 (2006).
Soutschek, et al., *Nature*, 432(7014):173-178 (Nov. 2004).
Sproat, et al., *Nucleic acids research*, 27(8):1950-1955 (1999).
Stetson, et al., *J.Exp.Med.* 203:1837-41 (2006).
Stojdl, et al., *Nat Med*, 6:821-825 (2000).
Strahle, et al., *Virology*, 351(1):101-11 (2006).
Stump, et al., *Nucleic Acids Research*, 21(23):5480-5484 (1993).
Sugiyama, et al., *J Immunol*, 174:2273-2279 (2005).
Sumpter, Jr., et al., *J Virol* 79, 2689 (Mar. 2005).
Tabeta, et al., *Proc Natl Acad Sci USA*, 101:3516-21 (Mar. 9, 2004).
Takahasi, et al., *Molecular Cell*, 29:428-440 (Feb. 29, 2008).
Tormo, et al., *Am J Pathol*, 169:665-72 (2006).
Tormo, et al., *Cancer Res.*, 66:5427-35 (2006).
Tschoep, et al., *J Mol Med*, 79:306-13 (2001).
Tschopp, et al., *Nature Reviews*, 4:95-104 (Feb. 2003).
Uno, et al., *Nat. Med.*, 12:693-8 (2006).
Urban-Klein, et al., *Gene Therapy*, 12(5):461-466 (2005).
Van Dijk, et al., *J. Gen. Virol.*, 85:1077-1093 (2004).
Van Dijk, et al., *Virology*, 211:320-323 (1995).
Van Holten, et al., *Arthritis Research*, 4:346-352 (2002).
Vollmer, et al., *Antisense Nucleic Acid Drug Dev*, 12:165-75 (Jun. 2002).
Wagner, et al., ROEMPP Online, Version 3.36, catchword "Lipofektion" (= engl. "lipofection").
Walther, et al., *Drugs*, 60(2):249-271 (Aug. 2000).
Wang, et al., *J Med Chem.* 47:6902-6913 (2004).
Wang, et al., *Nat Struct & Mol Biol*, 17(7):781-787 (Jul. 2010).
Weber, et al., *J Virol*, 80(10):5059-64 (May 2006).
Whelan, et al., *Curr. Topics in Microbial. and Immunol.*, 283:61-119 (2004).
Wu, et al., *Brain Research*, 1008(2):284-287 (May 22, 2004).
Xiao, et al., *Annual review of biochemistry*, 71:165-89 (2002).
Xu, et al., *Mol Cell*. 19(6):727-40 (Sep. 16, 2005).
Yang, et al., *Embo J*, 14(24):6095-6106 (Dec. 15, 1995).
Yang, et al., *Immunity*, 23(5):465-78 (Nov. 2005).
Yoneyama, et al., *Nat. Immunol.*, 5(7):730-737 (Jul. 2004).
Yoneyama, et al., *J. Biol.Chem.*, 282:15315-8 (2007).
Yoneyama, et al., *Journal of Immunlogy*, 175:2851-2858 (2005).
Yount, et al., *Archives of Biochemistry and Biophysics*, 113:288-295 (1966).
Zeh, et al., *Cancer Gene Ther*, 9:1001-1012 (2002).
Zimmermann, et al., *Nature*, 441(7089):111-114 (May 2006).
Zlatev, et a., *Org Lett*, 12(10):2190-2193 (2010).
EP 1 920 775.
Chawla-Sarkar et al., "Apoptosis and interferons:Role of interferon-stimulated genes as mediators of apoptosis", Apoptosis, 2003, 8(3), pp. 237-249.
Beller et al., "Noncovalent Attachment of Nucleotides by Fluorous-Fluorous Interactions: Application to a Simple Purification Principle for Synthetic DNA Fragments", Helvetica Chimica Acta, 2005, 88(1), p. 171-179.
Rehwinkel et al. "RIG-I Detects Viral Genomic RNA during Negative-Strand RNA Virus Infection", Cell 2010, 140, p. 397-408.
Behlke & Devor, "Chemical Synthesis of Oligonucleotides", Integrated DNA Technologies (2005), p. 1-12.
Fruscoloni et al., "Exonucleolytic degradation of double-stranded RNA by an activity in Xenopus laevis germinal vesicles", PNAS, (Feb. 2003), 100(4), p. 1639-1644.
Fullerton et al., "Structural and Functional Characterization of Sapovirus RNA-Dependent RNA Polymerase", J. Viral. (Nov. 2006) 81(4), p. 1858-1871.
Gantier et al., "The response of mammalian cells to double-stranded RNA", Cytokine and Growth Factor Reviews, 2007, 18(5-6), p. 363-371.
Habjan et al., "Processing of Genome 5' Termini as a Strategy of Negative-Strand RNA Viruses to Avoid RIG-I-Dependent Interferon Induction", PLoS One (Apr. 2008) vol. 3(4), p. 1-8.
Kim & Rossi, "Strategies for silencing human disease using RNA interference", Nature Reviews Genetics (Mar. 2007), vol. 8, p. 173-184.
Pleiss et al., "T7 RNA polymerase produces 5' end heterogeneity during in vitro transcription from certain templates", RNA (1998), 4: p. 1313-1317.
Rohayem et al.,"Characterization of norovirus 3Dpol RNA-dependent RNA polymerase activity and initiation of RNA synthesis", J. Gen Virol. (2006) 87, p. 2621-2630.
Saito et al., "Regulation of innate antiviral defenses through a shared repressor domain in RIG-1 and LGP2", PNAS (Jan. 2007), vo. 104(2), p. 582-587.
Straehle et al., "Activation of the Beta Interferon Promoter by Unnatural Sendai Virus Infection Requires RIG-I and is inhibited by Viral C Proteins", Journ.of Virol. (Nov. 2007), vol. 81(22), p. 12227-12237.
Soukup & Breaker, "Relationship between internucleotide linkage geometry and the stability of RNA", RNA (1999) 5, p. 1308-1325.
Vilfan et al., "An RNA toolbox for single-molecule force spectroscopy studies", Nucleic Acids Res. (2007) 35(19), p. 3625-6639.
Ivan Zlatev et al: "Efficient Solid-Phase Chemical Synthesis of 5'-Triphosphates of DNA, RNA, and their Analogues", Organic Letters, vol. 12, No. 10, May 21, 2010 (May 21, 2010), pp. 2190-2193, XP055005331, ISSN: 1523-7060, DOI: 10.1021/o11004214 table 2.
Lebedev A V et al: "Preparation of Oligodeoxynucleotide 5'-Triphosphates Using Solid Support Approach", Nucleosides, Nucleotides and Nucleic Acids, Taylor & Francis, Philadelphia, PA, USA, vol. 20, No. 4-7, Jan. 1, 2001 (Jan. 1, 2001), pp. 1403-1409, XP009081703, ISSN: 1525-7770, DOI: 10.1081/NCN-100002565 p. 1405.
Martin Schlee et al: "Recognition of 5' Triphosphate by RIG-I Helicase Requires Short Blunt Double-Stranded RNA as Contained in Panhandle of Negative-Strand Virus", Immunity, vol. 31, No. 1, Jul. 1, 2009 (Jul. 1, 2009), pp. 25-34, XP055032801, ISSN: 1074-7613, DOI: 10.1016/j.immuni.2009.05.008 cited in the application the whole document.

(56) References Cited

OTHER PUBLICATIONS

International Search Report cited in PCT/EP2013/070117 dated Nov. 14, 2013, 12 pages.

A

B

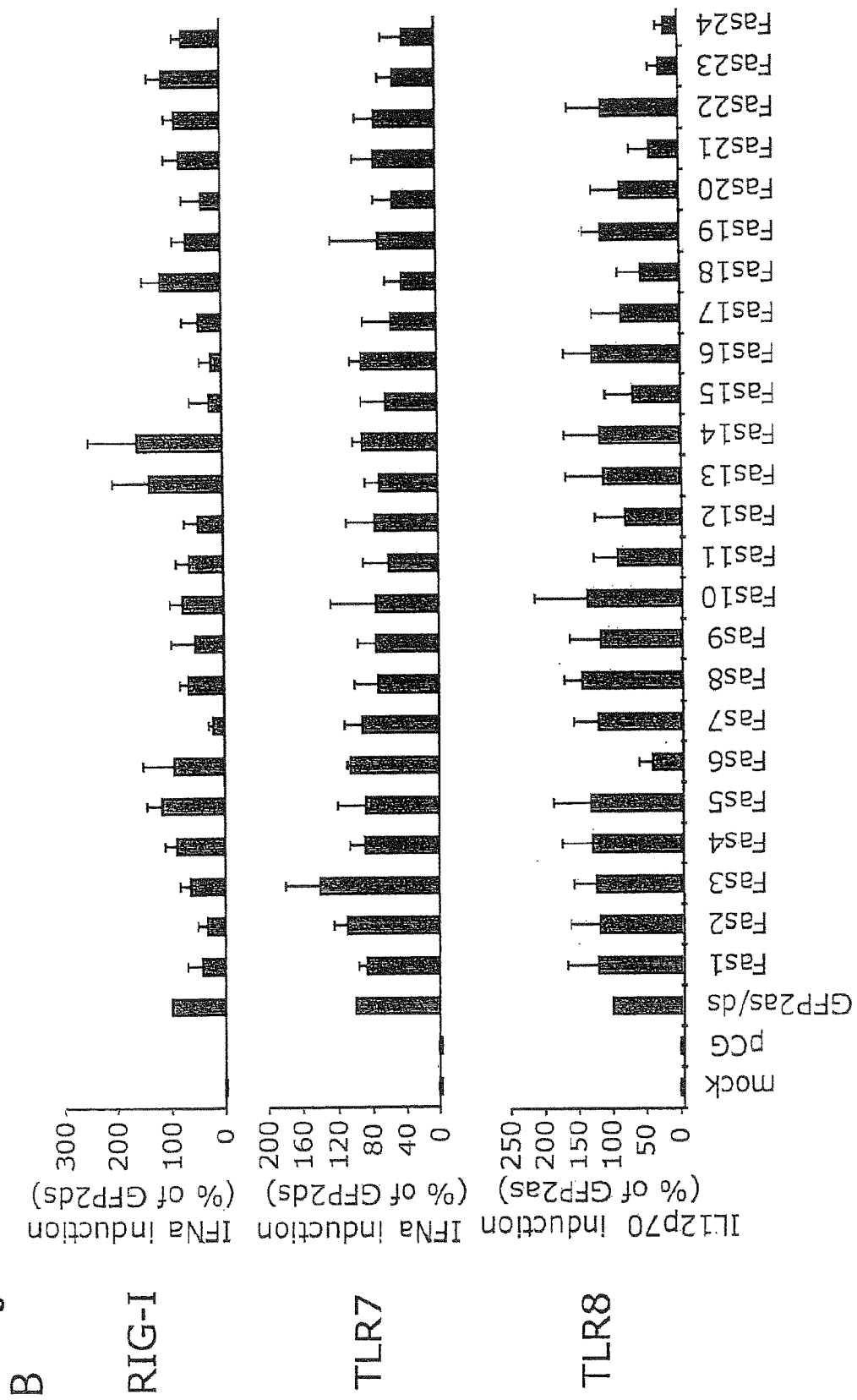

B

SEQUENCE LISTING

<160> NUMBER OF SEQ ID NOS: 77

<210> SEQ ID NO 1
<211> LENGTH: 24
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: nucleotide bearing decyl-O-ppp

<400> SEQUENCE: 1
gacgcugacc cugaaguuca ucuu                                              24

<210> SEQ ID NO 2
<211> LENGTH: 24
<212> TYPE: RNA
<213> ORGANISM: Artificial
<220> FEATURE:
<223> OTHER INFORMATION: Synthetic

<400> SEQUENCE: 2
gacgcugacc cugaaguuca ucuu                                              24

<210> SEQ ID NO 3
<211> LENGTH: 24
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: nucleotide bearing cholesteryl-ppp

<400> SEQUENCE: 3
gacgcugacc cugaaguuca ucuu                                              24

<210> SEQ ID NO 4
<211> LENGTH: 24
<212> TYPE: RNA
<213> ORGANISM: Artificial
<220> FEATURE:
<223> OTHER INFORMATION: synthetic
<220> FEATURE:
<221> NAME/KEY: misc_feature
<222> LOCATION: (1)..(1)
<223> OTHER INFORMATION: nucleotide being 2'-O-Me modified

<400> SEQUENCE: 4
gacgcugacc cugaaguuca ucuu                                              24

<210> SEQ ID NO 5
<211> LENGTH: 24
<212> TYPE: RNA
<213> ORGANISM: Artificial
<220> FEATURE:
<223> OTHER INFORMATION: Synthetic

<400> SEQUENCE: 5
aagaugaacu ucagggucag cguc                                              24

<210> SEQ ID NO 6
<211> LENGTH: 24
<212> TYPE: RNA
<213> ORGANISM: Artificial

```
<220> FEATURE:
<223> OTHER INFORMATION: Synthetic
<220> FEATURE:
<221> NAME/KEY: misc_feature
<222> LOCATION: (2)..(2)
<223> OTHER INFORMATION: nucleotide being 2'-O-Me modified

<400> SEQUENCE: 6
gacgcugacc cugaaguuca ucuu                                            24

<210> SEQ ID NO 7
<211> LENGTH: 24
<212> TYPE: RNA
<213> ORGANISM: Artificial
<220> FEATURE:
<223> OTHER INFORMATION: Synthetic

<400> SEQUENCE: 7
aagaugaacu ucagggucag cguc                                            24

<210> SEQ ID NO 8
<211> LENGTH: 24
<212> TYPE: RNA
<213> ORGANISM: Artificial
<220> FEATURE:
<223> OTHER INFORMATION: synthetic
<220> FEATURE:
<221> NAME/KEY: misc_feature
<222> LOCATION: (23)..(23)
<223> OTHER INFORMATION: nucleotide being 2'-O-Me modified

<400> SEQUENCE: 8
gacgcugacc cugaaguuca ucuu                                            24

<210> SEQ ID NO 9
<211> LENGTH: 24
<212> TYPE: RNA
<213> ORGANISM: Artificial
<220> FEATURE:
<223> OTHER INFORMATION: synthetic

<400> SEQUENCE: 9
aagaugaacu ucagggucag cguc                                            24

<210> SEQ ID NO 10
<211> LENGTH: 24
<212> TYPE: RNA
<213> ORGANISM: Artificial
<220> FEATURE:
<223> OTHER INFORMATION: synthetic
<220> FEATURE:
<221> NAME/KEY: misc_feature
<222> LOCATION: (24)..(24)
<223> OTHER INFORMATION: nucleotide being 2'-O-Me modified

<400> SEQUENCE: 10
gacgcugacc cugaaguuca ucuu                                            24

<210> SEQ ID NO 11
<211> LENGTH: 24
<212> TYPE: RNA
<213> ORGANISM: Artificial
<220> FEATURE:
<223> OTHER INFORMATION: synthetic

<400> SEQUENCE: 11
aagaugaacu ucagggucag cguc                                            24
```

```
<210> SEQ ID NO 12
<211> LENGTH: 24
<212> TYPE: RNA
<213> ORGANISM: Artificial
<220> FEATURE:
<223> OTHER INFORMATION: synthetic

<400> SEQUENCE: 12
gacgcugacc cugaaguuca ucuu                                            24

<210> SEQ ID NO 13
<211> LENGTH: 24
<212> TYPE: RNA
<213> ORGANISM: Artificial
<220> FEATURE:
<223> OTHER INFORMATION: synthetic
<220> FEATURE:
<221> NAME/KEY: misc_feature
<222> LOCATION: (24)..(24)
<223> OTHER INFORMATION: nucleotide being 2'-O-Me modified

<400> SEQUENCE: 13
aagaugaacu ucagggucag cguc                                            24

<210> SEQ ID NO 14
<211> LENGTH: 24
<212> TYPE: RNA
<213> ORGANISM: Artificial
<220> FEATURE:
<223> OTHER INFORMATION: synthetic

<400> SEQUENCE: 14
gacgcugacc cugaaguuca ucuu                                            24

<210> SEQ ID NO 15
<211> LENGTH: 24
<212> TYPE: RNA
<213> ORGANISM: Artificial
<220> FEATURE:
<223> OTHER INFORMATION: synthetic
<220> FEATURE:
<221> NAME/KEY: misc_feature
<222> LOCATION: (23)..(23)
<223> OTHER INFORMATION: nucleotide being 2'-O-Me modified

<400> SEQUENCE: 15
aagaugaacu ucagggucag cguc                                            24

<210> SEQ ID NO 16
<211> LENGTH: 24
<212> TYPE: RNA
<213> ORGANISM: Artificial
<220> FEATURE:
<223> OTHER INFORMATION: synthetic

<400> SEQUENCE: 16
gacgcugacc cugaaguuca ucuu                                            24

<210> SEQ ID NO 17
<211> LENGTH: 24
<212> TYPE: RNA
<213> ORGANISM: Artificial
<220> FEATURE:
<223> OTHER INFORMATION: synthetic
<220> FEATURE:
<221> NAME/KEY: misc_feature
<222> LOCATION: (2)..(2)
<223> OTHER INFORMATION: nucleotide being 2'-O-Me modified
```

```
<400> SEQUENCE: 17
aagaugaacu ucagggucag cguc                                              24

<210> SEQ ID NO 18
<211> LENGTH: 24
<212> TYPE: RNA
<213> ORGANISM: Artificial
<220> FEATURE:
<223> OTHER INFORMATION: synthetic

<400> SEQUENCE: 18
gacgcugacc cugaaguuca ucuu                                              24

<210> SEQ ID NO 19
<211> LENGTH: 24
<212> TYPE: RNA
<213> ORGANISM: Artificial
<220> FEATURE:
<223> OTHER INFORMATION: synthetic
<220> FEATURE:
<221> NAME/KEY: misc_feature
<222> LOCATION: (1)..(1)
<223> OTHER INFORMATION: nucleotide being 2'-O-Me modified

<400> SEQUENCE: 19
aagaugaacu ucagggucag cguc                                              24

<210> SEQ ID NO 20
<211> LENGTH: 24
<212> TYPE: RNA
<213> ORGANISM: Artificial
<220> FEATURE:
<223> OTHER INFORMATION: synthetic

<400> SEQUENCE: 20
gacgcugacc cugaaguuca ucuu                                              24

<210> SEQ ID NO 21
<211> LENGTH: 24
<212> TYPE: RNA
<213> ORGANISM: Artificial
<220> FEATURE:
<223> OTHER INFORMATION: synthetic
<220> FEATURE:
<221> NAME/KEY: misc_feature
<222> LOCATION: (1)..(1)
<223> OTHER INFORMATION: nucleotide being 2'-O-Me modified
<220> FEATURE:
<221> NAME/KEY: misc_feature
<222> LOCATION: (5)..(5)
<223> OTHER INFORMATION: nucleotide being 2'-O-Me modified
<220> FEATURE:
<221> NAME/KEY: misc_feature
<222> LOCATION: (13)..(13)
<223> OTHER INFORMATION: nucleotide being 2'-O-Me modified
<220> FEATURE:
<221> NAME/KEY: misc_feature
<222> LOCATION: (14)..(14)
<223> OTHER INFORMATION: nucleotide being 2'-O-Me modified
<220> FEATURE:
<221> NAME/KEY: misc_feature
<222> LOCATION: (15)..(15)
<223> OTHER INFORMATION: nucleotide being 2'-O-Me modified
<220> FEATURE:
<221> NAME/KEY: misc_feature
<222> LOCATION: (16)..(16)
<223> OTHER INFORMATION: nucleotide being 2'-O-Me modified
<220> FEATURE:
<221> NAME/KEY: misc_feature
<222> LOCATION: (21)..(21)
```

```
<223> OTHER INFORMATION: nucleotide being 2'-O-Me modified
<220> FEATURE:
<221> NAME/KEY: misc_feature
<222> LOCATION: (22)..(22)
<223> OTHER INFORMATION: nucleotide being 2'-O-Me modified
<220> FEATURE:
<221> NAME/KEY: misc_feature
<222> LOCATION: (24)..(24)
<223> OTHER INFORMATION: nucleotide being 2'-O-Me modified

<400> SEQUENCE: 21
aagaugaacu ucaggucag cguc                                            24

<210> SEQ ID NO 22
<211> LENGTH: 24
<212> TYPE: RNA
<213> ORGANISM: Artificial
<220> FEATURE:
<223> OTHER INFORMATION: synthetic
<220> FEATURE:
<221> NAME/KEY: misc_feature
<222> LOCATION: (20)..(20)
<223> OTHER INFORMATION: nucleotide being 2'-O-Me modified

<400> SEQUENCE: 22
gacgcugacc cugaaguuca ucuu                                           24

<210> SEQ ID NO 23
<211> LENGTH: 24
<212> TYPE: RNA
<213> ORGANISM: Artificial
<220> FEATURE:
<223> OTHER INFORMATION: synthetic
<220> FEATURE:
<221> NAME/KEY: misc_feature
<222> LOCATION: (13)..(13)
<223> OTHER INFORMATION: nucleotide being 2'-O-Me modified

<400> SEQUENCE: 23
aagaugaacu ucaggucag cguc                                            24

<210> SEQ ID NO 24
<211> LENGTH: 24
<212> TYPE: RNA
<213> ORGANISM: Artificial
<220> FEATURE:
<223> OTHER INFORMATION: synthetic
<220> FEATURE:
<221> NAME/KEY: misc_feature
<222> LOCATION: (20)..(20)
<223> OTHER INFORMATION: nucleotide being 2'-O-Me modified

<400> SEQUENCE: 24
gacgcugacc cugaaguuca ucuu                                           24

<210> SEQ ID NO 25
<211> LENGTH: 24
<212> TYPE: RNA
<213> ORGANISM: Artificial
<220> FEATURE:
<223> OTHER INFORMATION: synthetic
<220> FEATURE:
<221> NAME/KEY: misc_feature
<222> LOCATION: (6)..(6)
<223> OTHER INFORMATION: nucleotide being 2'-O-Me modified

<400> SEQUENCE: 25
aagaugaacu ucaggucag cguc                                            24
```

```
<210> SEQ ID NO 26
<211> LENGTH: 24
<212> TYPE: RNA
<213> ORGANISM: Artificial
<220> FEATURE:
<223> OTHER INFORMATION: synthetic
<220> FEATURE:
<221> NAME/KEY: misc_feature
<222> LOCATION: (15)..(15)
<223> OTHER INFORMATION: nucleotide being 2'-O-Me modified

<400> SEQUENCE: 26
gacgcugacc cugaaguuca ucuu                                              24

<210> SEQ ID NO 27
<211> LENGTH: 24
<212> TYPE: RNA
<213> ORGANISM: Artificial
<220> FEATURE:
<223> OTHER INFORMATION: synthetic
<220> FEATURE:
<221> NAME/KEY: misc_feature
<222> LOCATION: (13)..(13)
<223> OTHER INFORMATION: nucleotide being 2'-O-Me modified

<400> SEQUENCE: 27
aagaugaacu ucaggucag cguc                                               24

<210> SEQ ID NO 28
<211> LENGTH: 24
<212> TYPE: RNA
<213> ORGANISM: Artificial
<220> FEATURE:
<223> OTHER INFORMATION: synthetic
<220> FEATURE:
<221> NAME/KEY: misc_feature
<222> LOCATION: (15)..(15)
<223> OTHER INFORMATION: nucleotide being 2'-O-Me modified

<400> SEQUENCE: 28
gacgcugacc cugaaguuca ucuu                                              24

<210> SEQ ID NO 29
<211> LENGTH: 24
<212> TYPE: RNA
<213> ORGANISM: Artificial
<220> FEATURE:
<223> OTHER INFORMATION: synthetic
<220> FEATURE:
<221> NAME/KEY: misc_feature
<222> LOCATION: (6)..(6)
<223> OTHER INFORMATION: nucleotide being 2'-O-Me modified

<400> SEQUENCE: 29
aagaugaacu ucaggucag cguc                                               24

<210> SEQ ID NO 30
<211> LENGTH: 24
<212> TYPE: RNA
<213> ORGANISM: Artificial
<220> FEATURE:
<223> OTHER INFORMATION: synthetic
<220> FEATURE:
<221> NAME/KEY: misc_feature
<222> LOCATION: (20)..(20)
<223> OTHER INFORMATION: nucleotide being 2'-O-Me modified

<400> SEQUENCE: 30
gacgcugacc cugaaguuca ucuu                                              24
```

```
<210> SEQ ID NO 31
<211> LENGTH: 24
<212> TYPE: RNA
<213> ORGANISM: Artificial
<220> FEATURE:
<223> OTHER INFORMATION: synthetic
<220> FEATURE:
<221> NAME/KEY: misc_feature
<222> LOCATION: (22)..(22)
<223> OTHER INFORMATION: nucleotide being 2'-O-Me modified

<400> SEQUENCE: 31
aagaugaacu ucagggucag cguc                                          24

<210> SEQ ID NO 32
<211> LENGTH: 24
<212> TYPE: RNA
<213> ORGANISM: Artificial
<220> FEATURE:
<223> OTHER INFORMATION: synthetic
<220> FEATURE:
<221> NAME/KEY: misc_feature
<222> LOCATION: (15)..(15)
<223> OTHER INFORMATION: nucleotide being 2'-O-Me modified

<400> SEQUENCE: 32
gacgcugacc cugaaguuca ucuu                                          24

<210> SEQ ID NO 33
<211> LENGTH: 24
<212> TYPE: RNA
<213> ORGANISM: Artificial
<220> FEATURE:
<223> OTHER INFORMATION: synthetic
<220> FEATURE:
<221> NAME/KEY: misc_feature
<222> LOCATION: (22)..(22)
<223> OTHER INFORMATION: nucleotide being 2'-O-Me modified

<400> SEQUENCE: 33
aagaugaacu ucagggucag cguc                                          24

<210> SEQ ID NO 34
<211> LENGTH: 24
<212> TYPE: RNA
<213> ORGANISM: Artificial
<220> FEATURE:
<223> OTHER INFORMATION: synthetic
<220> FEATURE:
<221> NAME/KEY: misc_feature
<222> LOCATION: (3)..(3)
<223> OTHER INFORMATION: nucleotide being 2'-O-Me modified

<400> SEQUENCE: 34
gacgcugacc cugaaguuca ucuu                                          24

<210> SEQ ID NO 35
<211> LENGTH: 24
<212> TYPE: RNA
<213> ORGANISM: Artificial
<220> FEATURE:
<223> OTHER INFORMATION: synthetic
<220> FEATURE:
<221> NAME/KEY: misc_feature
<222> LOCATION: (13)..(13)
<223> OTHER INFORMATION: nucleotide being 2'-O-Me modified

<400> SEQUENCE: 35
aagaugaacu ucagggucag cguc                                          24
```

```
<210> SEQ ID NO 36
<211> LENGTH: 24
<212> TYPE: RNA
<213> ORGANISM: Artificial
<220> FEATURE:
<223> OTHER INFORMATION: synthetic
<220> FEATURE:
<221> NAME/KEY: misc_feature
<222> LOCATION: (3)..(3)
<223> OTHER INFORMATION: nucleotide being 2'-O-Me modified

<400> SEQUENCE: 36
gacgcugacc cugaaguuca ucuu                                              24

<210> SEQ ID NO 37
<211> LENGTH: 24
<212> TYPE: RNA
<213> ORGANISM: Artificial
<220> FEATURE:
<223> OTHER INFORMATION: synthetic
<220> FEATURE:
<221> NAME/KEY: misc_feature
<222> LOCATION: (6)..(6)
<223> OTHER INFORMATION: nucleotide being 2'-O-Me modified

<400> SEQUENCE: 37
aagaugaacu ucaggucag cguc                                               24

<210> SEQ ID NO 38
<211> LENGTH: 24
<212> TYPE: RNA
<213> ORGANISM: Artificial
<220> FEATURE:
<223> OTHER INFORMATION: synthetic
<220> FEATURE:
<221> NAME/KEY: misc_feature
<222> LOCATION: (1)..(1)
<223> OTHER INFORMATION: nucleotide being 2'-F modified

<400> SEQUENCE: 38
gacgcugacc cugaaguuca ucuu                                              24

<210> SEQ ID NO 39
<211> LENGTH: 24
<212> TYPE: RNA
<213> ORGANISM: Artificial
<220> FEATURE:
<223> OTHER INFORMATION: synthetic

<400> SEQUENCE: 39
aagaugaacu ucaggucag cguc                                               24

<210> SEQ ID NO 40
<211> LENGTH: 24
<212> TYPE: RNA
<213> ORGANISM: Artificial
<220> FEATURE:
<223> OTHER INFORMATION: synthetic
<220> FEATURE:
<221> NAME/KEY: misc_feature
<222> LOCATION: (2)..(2)
<223> OTHER INFORMATION: nucleotide being 2'-F modified

<400> SEQUENCE: 40
gacgcugacc cugaaguuca ucuu                                              24

<210> SEQ ID NO 41
```

```
<211> LENGTH: 24
<212> TYPE: RNA
<213> ORGANISM: Artificial
<220> FEATURE:
<223> OTHER INFORMATION: synthetic

<400> SEQUENCE: 41
aagaugaacu ucagggucag cguc                                              24

<210> SEQ ID NO 42
<211> LENGTH: 24
<212> TYPE: RNA
<213> ORGANISM: Artificial
<220> FEATURE:
<223> OTHER INFORMATION: synthetic
<220> FEATURE:
<221> NAME/KEY: misc_feature
<222> LOCATION: (23)..(23)
<223> OTHER INFORMATION: nucleotide being 2'-F modified

<400> SEQUENCE: 42
gacgcugacc cugaaguuca ucuu                                              24

<210> SEQ ID NO 43
<211> LENGTH: 24
<212> TYPE: RNA
<213> ORGANISM: Artificial
<220> FEATURE:
<223> OTHER INFORMATION: synthetic

<400> SEQUENCE: 43
aagaugaacu ucagggucag cguc                                              24

<210> SEQ ID NO 44
<211> LENGTH: 24
<212> TYPE: RNA
<213> ORGANISM: Artificial
<220> FEATURE:
<223> OTHER INFORMATION: synthetic
<220> FEATURE:
<221> NAME/KEY: misc_feature
<222> LOCATION: (24)..(24)
<223> OTHER INFORMATION: nucleotide being 2'-F modified

<400> SEQUENCE: 44
gacgcugacc cugaaguuca ucuu                                              24

<210> SEQ ID NO 45
<211> LENGTH: 24
<212> TYPE: RNA
<213> ORGANISM: Artificial
<220> FEATURE:
<223> OTHER INFORMATION: synthetic

<400> SEQUENCE: 45
aagaugaacu ucagggucag cguc                                              24

<210> SEQ ID NO 46
<211> LENGTH: 24
<212> TYPE: RNA
<213> ORGANISM: Artificial
<220> FEATURE:
<223> OTHER INFORMATION: synthetic

<400> SEQUENCE: 46
gacgcugacc cugaaguuca ucuu                                              24
```

```
<210> SEQ ID NO 47
<211> LENGTH: 24
<212> TYPE: RNA
<213> ORGANISM: Artificial
<220> FEATURE:
<223> OTHER INFORMATION: synthetic
<220> FEATURE:
<221> NAME/KEY: misc_feature
<222> LOCATION: (24)..(24)
<223> OTHER INFORMATION: nucleotide being 2'-F modified

<400> SEQUENCE: 47
aagaugaacu ucaggucag cguc                                              24

<210> SEQ ID NO 48
<211> LENGTH: 24
<212> TYPE: RNA
<213> ORGANISM: Artificial
<220> FEATURE:
<223> OTHER INFORMATION: synthetic

<400> SEQUENCE: 48
gacgcugacc cugaaguuca ucuu                                             24

<210> SEQ ID NO 49
<211> LENGTH: 24
<212> TYPE: RNA
<213> ORGANISM: Artificial
<220> FEATURE:
<223> OTHER INFORMATION: synthetic
<220> FEATURE:
<221> NAME/KEY: misc_feature
<222> LOCATION: (23)..(23)
<223> OTHER INFORMATION: nucleotide being 2'-F modified

<400> SEQUENCE: 49
aagaugaacu ucaggucag cguc                                              24

<210> SEQ ID NO 50
<211> LENGTH: 24
<212> TYPE: RNA
<213> ORGANISM: Artificial
<220> FEATURE:
<223> OTHER INFORMATION: synthetic

<400> SEQUENCE: 50
gacgcugacc cugaaguuca ucuu                                             24

<210> SEQ ID NO 51
<211> LENGTH: 24
<212> TYPE: RNA
<213> ORGANISM: Artificial
<220> FEATURE:
<223> OTHER INFORMATION: synthetic
<220> FEATURE:
<221> NAME/KEY: misc_feature
<222> LOCATION: (2)..(2)
<223> OTHER INFORMATION: nucleotide being 2'-F modified

<400> SEQUENCE: 51
aagaugaacu ucaggucag cguc                                              24

<210> SEQ ID NO 52
<211> LENGTH: 24
<212> TYPE: RNA
<213> ORGANISM: Artificial
<220> FEATURE:
<223> OTHER INFORMATION: synthetic
```

```
<400> SEQUENCE: 52
gacgcugacc cugaaguuca ucuu                                              24

<210> SEQ ID NO 53
<211> LENGTH: 24
<212> TYPE: RNA
<213> ORGANISM: Artificial
<220> FEATURE:
<223> OTHER INFORMATION: synthetic
<220> FEATURE:
<221> NAME/KEY: misc_feature
<222> LOCATION: (1)..(1)
<223> OTHER INFORMATION: nucleotide being 2'-F modified

<400> SEQUENCE: 53
aagaugaacu ucaggucag cguc                                               24

<210> SEQ ID NO 54
<211> LENGTH: 24
<212> TYPE: RNA
<213> ORGANISM: Artificial
<220> FEATURE:
<223> OTHER INFORMATION: synthetic
<220> FEATURE:
<221> NAME/KEY: misc_feature
<222> LOCATION: (1)..(1)
<223> OTHER INFORMATION: nucleotide bearing triphosphate

<400> SEQUENCE: 54
gacgcugacc cugaaguuca ucuu                                              24

<210> SEQ ID NO 55
<211> LENGTH: 24
<212> TYPE: RNA
<213> ORGANISM: Artificial
<220> FEATURE:
<223> OTHER INFORMATION: synthetic

<400> SEQUENCE: 55
aagaugaacu ucaggucag cguc                                               24

<210> SEQ ID NO 56
<211> LENGTH: 24
<212> TYPE: RNA
<213> ORGANISM: Artificial
<220> FEATURE:
<223> OTHER INFORMATION: synthetic
<220> FEATURE:
<221> NAME/KEY: misc_feature
<222> LOCATION: (15)..(15)
<223> OTHER INFORMATION: nucleotide being 2'-O-Me modified

<400> SEQUENCE: 56
gacgcugacc cugaaguuca ucuu                                              24

<210> SEQ ID NO 57
<211> LENGTH: 24
<212> TYPE: RNA
<213> ORGANISM: Artificial
<220> FEATURE:
<223> OTHER INFORMATION: synthetic
<220> FEATURE:
<221> NAME/KEY: misc_feature
<222> LOCATION: (1)..(2)
<223> OTHER INFORMATION: nucleotides linked by phosphothioate
<220> FEATURE:
<221> NAME/KEY: misc_feature
<222> LOCATION: (2)..(3)
<223> OTHER INFORMATION: nucleotides linked by phosphothioate
```

-continued

```
<220> FEATURE:
<221> NAME/KEY: misc_feature
<222> LOCATION: (22)..(22)
<223> OTHER INFORMATION: nucleotide being 2'-O-Me modified

<400> SEQUENCE: 57
aagaugaacu ucagggucag cguc                                              24

<210> SEQ ID NO 58
<211> LENGTH: 24
<212> TYPE: RNA
<213> ORGANISM: Artificial
<220> FEATURE:
<223> OTHER INFORMATION: synthetic
<220> FEATURE:
<221> NAME/KEY: misc_feature
<222> LOCATION: (1)..(2)
<223> OTHER INFORMATION: nucleotides linked by phosphothioate
<220> FEATURE:
<221> NAME/KEY: misc_feature
<222> LOCATION: (2)..(3)
<223> OTHER INFORMATION: nucleotides linked by phosphothioate
<220> FEATURE:
<221> NAME/KEY: misc_feature
<222> LOCATION: (15)..(15)
<223> OTHER INFORMATION: nucleotide being 2'-O-Me modified

<400> SEQUENCE: 58
gacgcugacc cugaaguuca ucuu                                              24

<210> SEQ ID NO 59
<211> LENGTH: 24
<212> TYPE: RNA
<213> ORGANISM: Artificial
<220> FEATURE:
<223> OTHER INFORMATION: synthetic
<220> FEATURE:
<221> NAME/KEY: misc_feature
<222> LOCATION: (22)..(22)
<223> OTHER INFORMATION: nucleotide being 2'-O-Me modified

<400> SEQUENCE: 59
aagaugaacu ucagggucag cguc                                              24

<210> SEQ ID NO 60
<211> LENGTH: 24
<212> TYPE: RNA
<213> ORGANISM: Artificial
<220> FEATURE:
<223> OTHER INFORMATION: synthetic
<220> FEATURE:
<221> NAME/KEY: misc_feature
<222> LOCATION: (1)..(2)
<223> OTHER INFORMATION: nucleotides linked by phosphothioate
<220> FEATURE:
<221> NAME/KEY: misc_feature
<222> LOCATION: (2)..(3)
<223> OTHER INFORMATION: nucleotides linked by phosphothioate
<220> FEATURE:
<221> NAME/KEY: misc_feature
<222> LOCATION: (15)..(15)
<223> OTHER INFORMATION: nucleotide being 2'-O-Me modified

<400> SEQUENCE: 60
gacgcugacc cugaaguuca ucuu                                              24

<210> SEQ ID NO 61
<211> LENGTH: 24
<212> TYPE: RNA
<213> ORGANISM: Artificial
<220> FEATURE:
```

```
<223> OTHER INFORMATION: synthetic
<220> FEATURE:
<221> NAME/KEY: misc_feature
<222> LOCATION: (1)..(2)
<223> OTHER INFORMATION: nucleotides linked by phosphothioate
<220> FEATURE:
<221> NAME/KEY: misc_feature
<222> LOCATION: (2)..(3)
<223> OTHER INFORMATION: nucleotides linked by phosphothioate
<220> FEATURE:
<221> NAME/KEY: misc_feature
<222> LOCATION: (22)..(22)
<223> OTHER INFORMATION: nucleotide being 2'-O-Me modified

<400> SEQUENCE: 61
aagaugaacu ucagggucag cguc                                          24

<210> SEQ ID NO 62
<211> LENGTH: 24
<212> TYPE: RNA
<213> ORGANISM: Artificial
<220> FEATURE:
<223> OTHER INFORMATION: synthetic
<220> FEATURE:
<221> NAME/KEY: misc_feature
<222> LOCATION: (1)..(2)
<223> OTHER INFORMATION: nucleotides linked by phosphothioate
<220> FEATURE:
<221> NAME/KEY: misc_feature
<222> LOCATION: (2)..(3)
<223> OTHER INFORMATION: nucleotides linked by phosphothioate

<400> SEQUENCE: 62
gacgcugacc cugaaguuca ucuu                                          24

<210> SEQ ID NO 63
<211> LENGTH: 24
<212> TYPE: RNA
<213> ORGANISM: Artificial
<220> FEATURE:
<223> OTHER INFORMATION: synthetic
<220> FEATURE:
<221> NAME/KEY: misc_feature
<222> LOCATION: (1)..(2)
<223> OTHER INFORMATION: nucleotides linked by phosphothioate
<220> FEATURE:
<221> NAME/KEY: misc_feature
<222> LOCATION: (2)..(3)
<223> OTHER INFORMATION: nucleotides linked by phosphothioate

<400> SEQUENCE: 63
aagaugaacu ucagggucag cguc                                          24

<210> SEQ ID NO 64
<211> LENGTH: 24
<212> TYPE: RNA
<213> ORGANISM: Artificial
<220> FEATURE:
<223> OTHER INFORMATION: synthetic
<220> FEATURE:
<221> NAME/KEY: misc_feature
<222> LOCATION: (1)..(2)
<223> OTHER INFORMATION: nucleotides linked by phosphothioate
<220> FEATURE:
<221> NAME/KEY: misc_feature
<222> LOCATION: (2)..(3)
<223> OTHER INFORMATION: nucleotides linked by phosphothioate
<220> FEATURE:
<221> NAME/KEY: misc_feature
<222> LOCATION: (15)..(15)
<223> OTHER INFORMATION: nucleotide being 2'-O-Me modified

<400> SEQUENCE: 64
```

```
gacgcugacc cugaaguuca ucuu                                          24
```

<210> SEQ ID NO 65
<211> LENGTH: 24
<212> TYPE: RNA
<213> ORGANISM: Artificial
<220> FEATURE:
<223> OTHER INFORMATION: synthetic
<220> FEATURE:
<221> NAME/KEY: misc_feature
<222> LOCATION: (1)..(2)
<223> OTHER INFORMATION: nucleotides linked by phosphothioate
<220> FEATURE:
<221> NAME/KEY: misc_feature
<222> LOCATION: (2)..(3)
<223> OTHER INFORMATION: nucleotides linked by phosphothioate
<220> FEATURE:
<221> NAME/KEY: misc_feature
<222> LOCATION: (22)..(22)
<223> OTHER INFORMATION: nucleotide being 2'-O-Me modified

<400> SEQUENCE: 65

```
aagaugaacu ucagggucag cguc                                          24
```

<210> SEQ ID NO 66
<211> LENGTH: 24
<212> TYPE: RNA
<213> ORGANISM: Artificial
<220> FEATURE:
<223> OTHER INFORMATION: synthetic
<220> FEATURE:
<221> NAME/KEY: misc_feature
<222> LOCATION: (23)..(23)
<223> OTHER INFORMATION: nucleotide being 2'-F modified

<400> SEQUENCE: 66

```
gacgcugacc cugaaguuca ucuu                                          24
```

<210> SEQ ID NO 67
<211> LENGTH: 24
<212> TYPE: RNA
<213> ORGANISM: Artificial
<220> FEATURE:
<223> OTHER INFORMATION: synthetic
<220> FEATURE:
<221> NAME/KEY: misc_feature
<222> LOCATION: (12)..(12)
<223> OTHER INFORMATION: nucleotide being 2'-F modified

<400> SEQUENCE: 67

```
aagaugaacu ucagggucag cguc                                          24
```

<210> SEQ ID NO 68
<211> LENGTH: 24
<212> TYPE: RNA
<213> ORGANISM: Artificial
<220> FEATURE:
<223> OTHER INFORMATION: synthetic
<220> FEATURE:
<221> NAME/KEY: misc_feature
<222> LOCATION: (1)..(2)
<223> OTHER INFORMATION: nucleotides linked by phosphothioate
<220> FEATURE:
<221> NAME/KEY: misc_feature
<222> LOCATION: (2)..(3)
<223> OTHER INFORMATION: nucleotides linked by phosphothioate
<220> FEATURE:
<221> NAME/KEY: misc_feature
<222> LOCATION: (7)..(7)
<223> OTHER INFORMATION: nucleotide being 2'-F modified
<220> FEATURE:

```
<221> NAME/KEY: misc_feature
<222> LOCATION: (15)..(15)
<223> OTHER INFORMATION: nucleotide being 2'-O-Me modified
<220> FEATURE:
<221> NAME/KEY: misc_feature
<222> LOCATION: (23)..(23)
<223> OTHER INFORMATION: nucleotide being 2'-F modified

<400> SEQUENCE: 68
gacgcugacc cugaaguuca ucuu                                              24

<210> SEQ ID NO 69
<211> LENGTH: 24
<212> TYPE: RNA
<213> ORGANISM: Artificial
<220> FEATURE:
<223> OTHER INFORMATION: synthetic
<220> FEATURE:
<221> NAME/KEY: misc_feature
<222> LOCATION: (1)..(2)
<223> OTHER INFORMATION: nucleotides linked by phosphothioate
<220> FEATURE:
<221> NAME/KEY: misc_feature
<222> LOCATION: (2)..(3)
<223> OTHER INFORMATION: nucleotides linked by phosphothioate
<220> FEATURE:
<221> NAME/KEY: misc_feature
<222> LOCATION: (12)..(12)
<223> OTHER INFORMATION: nucleotide being 2'-F modified
<220> FEATURE:
<221> NAME/KEY: misc_feature
<222> LOCATION: (22)..(22)
<223> OTHER INFORMATION: nucleotide being 2'-O-Me modified

<400> SEQUENCE: 69
aagaugaacu ucaggucag cguc                                               24

<210> SEQ ID NO 70
<211> LENGTH: 24
<212> TYPE: RNA
<213> ORGANISM: Artificial
<220> FEATURE:
<223> OTHER INFORMATION: synthetic
<220> FEATURE:
<221> NAME/KEY: misc_feature
<222> LOCATION: (1)..(1)
<223> OTHER INFORMATION: nucleotide bearing triphosphate
<220> FEATURE:
<221> NAME/KEY: misc_feature
<222> LOCATION: (7)..(7)
<223> OTHER INFORMATION: nucleotide being 2'-F modified
<220> FEATURE:
<221> NAME/KEY: misc_feature
<222> LOCATION: (15)..(15)
<223> OTHER INFORMATION: nucleotide being 2'-O-Me modified
<220> FEATURE:
<221> NAME/KEY: misc_feature
<222> LOCATION: (22)..(23)
<223> OTHER INFORMATION: nucleotides linked by phosphothioate
<220> FEATURE:
<221> NAME/KEY: misc_feature
<222> LOCATION: (23)..(24)
<223> OTHER INFORMATION: nucleotides linked by phosphothioate
<220> FEATURE:
<221> NAME/KEY: misc_feature
<222> LOCATION: (23)..(23)
<223> OTHER INFORMATION: nucleotide being 2'-F modified

<400> SEQUENCE: 70
gacgcugacc cugaaguuca ucuu                                              24

<210> SEQ ID NO 71
<211> LENGTH: 24
```

```
<212> TYPE: RNA
<213> ORGANISM: Artificial
<220> FEATURE:
<223> OTHER INFORMATION: synthetic
<220> FEATURE:
<221> NAME/KEY: misc_feature
<222> LOCATION: (1)..(2)
<223> OTHER INFORMATION: nucleotides linked by phosphothioate
<220> FEATURE:
<221> NAME/KEY: misc_feature
<222> LOCATION: (2)..(3)
<223> OTHER INFORMATION: nucleotides linked by phosphothioate
<220> FEATURE:
<221> NAME/KEY: misc_feature
<222> LOCATION: (12)..(12)
<223> OTHER INFORMATION: nucleotide being 2'-F modified
<220> FEATURE:
<221> NAME/KEY: misc_feature
<222> LOCATION: (22)..(22)
<223> OTHER INFORMATION: nucleotide being 2'-O-Me modified

<400> SEQUENCE: 71
aagaugaacu ucagggucag cguc                                            24

<210> SEQ ID NO 72
<211> LENGTH: 24
<212> TYPE: RNA
<213> ORGANISM: Artificial
<220> FEATURE:
<223> OTHER INFORMATION: synthetic
<220> FEATURE:
<221> NAME/KEY: misc_feature
<222> LOCATION: (7)..(7)
<223> OTHER INFORMATION: nucleotide being 2'-F modified
<220> FEATURE:
<221> NAME/KEY: misc_feature
<222> LOCATION: (15)..(15)
<223> OTHER INFORMATION: nucleotide being 2'-O-Me modified
<220> FEATURE:
<221> NAME/KEY: misc_feature
<222> LOCATION: (22)..(23)
<223> OTHER INFORMATION: nucleotides linked by phosphothioate
<220> FEATURE:
<221> NAME/KEY: misc_feature
<222> LOCATION: (23)..(24)
<223> OTHER INFORMATION: nucleotides linked by phosphothioate
<220> FEATURE:
<221> NAME/KEY: misc_feature
<222> LOCATION: (23)..(23)
<223> OTHER INFORMATION: nucleotide being 2'-F modified

<400> SEQUENCE: 72
gacgcugacc cugaaguuca ucuu                                            24

<210> SEQ ID NO 73
<211> LENGTH: 24
<212> TYPE: RNA
<213> ORGANISM: Artificial
<220> FEATURE:
<223> OTHER INFORMATION: synthetic
<220> FEATURE:
<221> NAME/KEY: misc_feature
<222> LOCATION: (1)..(2)
<223> OTHER INFORMATION: nucleotides linked by phosphothioate
<220> FEATURE:
<221> NAME/KEY: misc_feature
<222> LOCATION: (2)..(3)
<223> OTHER INFORMATION: nucleotides linked by phosphothioate
<220> FEATURE:
<221> NAME/KEY: misc_feature
<222> LOCATION: (12)..(12)
<223> OTHER INFORMATION: nucleotide being 2'-F modified
<220> FEATURE:
<221> NAME/KEY: misc_feature
<222> LOCATION: (22)..(22)
```

<223> OTHER INFORMATION: nucleotide being 2'-O-Me modified

<400> SEQUENCE: 73
aagaugaacu ucagggucag cguc                                         24

<210> SEQ ID NO 74
<211> LENGTH: 24
<212> TYPE: RNA
<213> ORGANISM: Artificial
<220> FEATURE:
<223> OTHER INFORMATION: synthetic
<220> FEATURE:
<221> NAME/KEY: misc_feature
<222> LOCATION: (1)..(1)
<223> OTHER INFORMATION: nucleotide bearing triphosphate
<220> FEATURE:
<221> NAME/KEY: misc_feature
<222> LOCATION: (1)..(2)
<223> OTHER INFORMATION: nucleotides linked by phosphothioate
<220> FEATURE:
<221> NAME/KEY: misc_feature
<222> LOCATION: (2)..(3)
<223> OTHER INFORMATION: nucleotides linked by phosphothioate
<220> FEATURE:
<221> NAME/KEY: misc_feature
<222> LOCATION: (7)..(7)
<223> OTHER INFORMATION: nucleotide being 2'-F modified
<220> FEATURE:
<221> NAME/KEY: misc_feature
<222> LOCATION: (15)..(15)
<223> OTHER INFORMATION: nucleotide being 2'-O-Me modified
<220> FEATURE:
<221> NAME/KEY: misc_feature
<222> LOCATION: (22)..(23)
<223> OTHER INFORMATION: nucleotides linked by phosphothioate
<220> FEATURE:
<221> NAME/KEY: misc_feature
<222> LOCATION: (23)..(24)
<223> OTHER INFORMATION: nucleotides linked by phosphothioate
<220> FEATURE:
<221> NAME/KEY: misc_feature
<222> LOCATION: (23)..(23)
<223> OTHER INFORMATION: nucleotide being 2'-F modified

<400> SEQUENCE: 74
gacgcugacc cugaaguuca ucuu                                         24

<210> SEQ ID NO 75
<211> LENGTH: 24
<212> TYPE: RNA
<213> ORGANISM: Artificial
<220> FEATURE:
<223> OTHER INFORMATION: synthetic
<220> FEATURE:
<221> NAME/KEY: misc_feature
<222> LOCATION: (1)..(2)
<223> OTHER INFORMATION: nucleotides linked by phosphothioate
<220> FEATURE:
<221> NAME/KEY: misc_feature
<222> LOCATION: (2)..(3)
<223> OTHER INFORMATION: nucleotides linked by phosphothioate
<220> FEATURE:
<221> NAME/KEY: misc_feature
<222> LOCATION: (12)..(12)
<223> OTHER INFORMATION: nucleotide being 2'-F modified
<220> FEATURE:
<221> NAME/KEY: misc_feature
<222> LOCATION: (22)..(22)
<223> OTHER INFORMATION: nucleotide being 2'-O-Me modified

<400> SEQUENCE: 75
aagaugaacu ucagggucag cguc                                         24

```
<210> SEQ ID NO 76
<211> LENGTH: 24
<212> TYPE: RNA
<213> ORGANISM: Artificial
<220> FEATURE:
<223> OTHER INFORMATION: synthetic
<220> FEATURE:
<221> NAME/KEY: misc_feature
<222> LOCATION: (1)..(2)
<223> OTHER INFORMATION: nucleotides linked by phosphothioate
<220> FEATURE:
<221> NAME/KEY: misc_feature
<222> LOCATION: (2)..(3)
<223> OTHER INFORMATION: nucleotides linked by phosphothioate
<220> FEATURE:
<221> NAME/KEY: misc_feature
<222> LOCATION: (7)..(7)
<223> OTHER INFORMATION: nucleotide being 2'-F modified
<220> FEATURE:
<221> NAME/KEY: misc_feature
<222> LOCATION: (15)..(15)
<223> OTHER INFORMATION: nucleotide being 2'-O-Me modified
<220> FEATURE:
<221> NAME/KEY: misc_feature
<222> LOCATION: (22)..(23)
<223> OTHER INFORMATION: nucleotides linked by phosphothioate
<220> FEATURE:
<221> NAME/KEY: misc_feature
<222> LOCATION: (23)..(24)
<223> OTHER INFORMATION: nucleotides linked by phosphothioate
<220> FEATURE:
<221> NAME/KEY: misc_feature
<222> LOCATION: (23)..(23)
<223> OTHER INFORMATION: nucleotide being 2'-F modified

<400> SEQUENCE: 76
gacgcugacc cugaaguuca ucuu                                         24

<210> SEQ ID NO 77
<211> LENGTH: 24
<212> TYPE: RNA
<213> ORGANISM: Artificial
<220> FEATURE:
<223> OTHER INFORMATION: synthetic
<220> FEATURE:
<221> NAME/KEY: misc_feature
<222> LOCATION: (1)..(2)
<223> OTHER INFORMATION: nucleotides linked by phosphothioate
<220> FEATURE:
<221> NAME/KEY: misc_feature
<222> LOCATION: (2)..(3)
<223> OTHER INFORMATION: nucleotides linked by phosphothioate
<220> FEATURE:
<221> NAME/KEY: misc_feature
<222> LOCATION: (12)..(12)
<223> OTHER INFORMATION: nucleotide being 2'-F modified
<220> FEATURE:
<221> NAME/KEY: misc_feature
<222> LOCATION: (22)..(22)
<223> OTHER INFORMATION: nucleotide being 2'-O-Me modified

<400> SEQUENCE: 77
aagaugaacu ucagggucag cguc                                         24
```

RIG-I LIGANDS AND METHODS FOR PRODUCING THEM

CROSS REFERENCE TO RELATED APPLICATION

This application is a 35 U.S.C. 371 National Phase Entry Application from PCT/EP2013/070117, filed Sep. 26, 2013, which claims the benefit of European Patent Application No. 12186444.1 filed on Sep. 27, 2012, the disclosure of which is incorporated herein in its entirety by reference.

The present invention relates to new triphosphate-modified oligonucleotides which may act as RIG-I ligands as well as a new method allowing the synthesis and purification in high yield and purity suitable for pharmaceutical applications.

BACKGROUND OF THE INVENTION

Schlee et al., *Immunity*, 2009, 31, 25-34 describe blunt-ended double stranded RNAs carrying a 5'-O-triphosphate moiety on one of the strands that act as potent stimulators of the immune system by binding the RIG-I helicase. Thus, there is a need to provide a simple and efficient method for preparing triphosphate-modified oligonucleotides in high purity, suitable for pharmaceutical applications.

The coupling of triphosphate groups or analogues thereof to the 5'-OH group of nucleosidic compounds is well known in the art. Ludwig J. et al., *J. Org. Chem.*, 1989, 54, 631-635 disclose a solution triphosphorylation method for preparing 5'-O-triphosphates of nucleosides and analogues using 2-chloro-4H-1,3,2-benzodioxaphosphorin-4-one as the phosphitylating agent. Gaur R. K. et al., 1992, *Tetrahedron Letters*, 33, 3301-3304 describe the use of said method on solid-phase for the synthesis of 2'-O-methylribonucleoside 5'-O-triphosphates and their $P_\alpha$-thio analogues. U.S. Pat. No. 6,900,308 B2 discloses the solid-phase synthesis of modified nucleoside 5'-O-triphosphates as potential antiviral compounds and U.S. Pat. Nos. 7,285,658, 7,598,230 and 7,807,653 disclose triphosphate analogues of nucleosides with modifications in the sugar, nucleobase and in the triphosphate entity.

WO96/40159 describes a method for producing capped RNA or RNA analogue molecules, wherein an RNA or RNA analogue oligonucleotide is reacted with a phosphitylating agent such as 2-chloro-4H-1,3,2-benzodioxaphosphorin-4-one or a ring-substituted derivative thereof. The resulting intermediate is reacted with a phosphate or pyrophosphate or salt thereof, oxidized or hydrolyzed. The di- or triphosphorylated RNA or RNA analogue is capped by reacting with an activated $m^7G$ tri-, di- or monophosphate or analogue.

WO 2009/060281 describes immune stimulatory oligoribonucleotide analogues containing modified oligophosphate moieties and methods for the preparation of such compounds. This method includes the synthesis of the oligonucleotide on a solid support, reacting a nucleotide at a 5'-end of the oligonucleotide with a phosphitylating agent such as 2-chloro-4H-1,3,2-benzodioxaphosphorin-4-one in a suitable solvent and in the presence of a base, reacting the phosphitylated oligonucleotide with a pyrophosphate or pyrophosphate analogue, oxidizing the oligonucleotide with an oxidizing agent and deprotecting the oligonucleotide to give a triphosphate- or triphosphate analogue-modified oligonucleotide.

Polyacrylamide gel-electrophoresis as employed in WO 96/40159 is applicable only for small scale separations. The resolution power of ion exchange chromatography for 5'-mono-, di-, triphosphorylated products of longer oligoribonucleotides is limited. The required denaturing conditions make separation a tedious task (Sproat, 1999; Zlatev, 2010; WO 2009/060281), moreover, products are usually contaminated with n-1, n-2 sequences and their mono- and diphosphates resulting in insufficient purity. Given the sensitivity for precise terminal structures of the RIG-I ligands, these purification methods are suboptimal for pharmacological applications.

Thus, there is a high need for new triphosphorylated oligonucleotides and analogues thereof, in particular having RIG-I selectivity as well as methods for preparing such compounds.

The present invention therefor relates to novel 5'-triphosphorylated oligonucleotides and analogues thereof which can be produced in large scales for potential clinical use as well as a convenient preparation method for such oligonucleotides. Furthermore, modifications of oligonucleotides are described which establish, maintain and/or improve the RIG-I selectivity of the oligonucleotides or enhance their chemical stability.

Thus, a first aspect of the present invention relates to a modified oligonucleotide of Formula (I)

$$Z-Y-X-\overset{\overset{V_5}{\|}}{\underset{V_6}{P}}-W_3-\overset{\overset{V_3}{\|}}{\underset{V_4}{P}}-W_2-\overset{\overset{V_1}{\|}}{\underset{V_2}{P}}-W_1-ON \qquad I$$

wherein $V_1$, $V_3$ and $V_5$ are independently in each case selected from O, S and Se;

$V_2$, $V_4$ and $V_6$ are independently in each case selected from OH, $OR^1$, SH, $SR^1$, F, $NH_2$, $NHR^1$, $N(R^1)_2$ and $BH_3^-M^+$, $W_1$ is O or S, $W_2$ is O, S, NH or $NR^2$, $W_3$ is O, S, NH, $NR^2$, $CH_2$, CHHal or $C(Hal)_2$, $R^1$, $R^2$ and $R^3$ are selected from $C_{1-6}$ alkyl, $C_{2-6}$ alkenyl, $C_{2-6}$ alkynyl, $C_{2-6}$ acyl or a cyclic group, each optionally substituted, or wherein two $R^1$ may form a ring together with an N-atom bound thereto, $M^+$ is a cation, X is NH, $NR^3$, O or S, Z represents a capture tag or H, Y represents a bond or a linker connecting the capture tag to X, and ON represents an oligonucleotide comprising at least 4 nucleotide or nucleotide analogue building blocks.

The term "oligonucleotide" in the context of the present application encompasses compounds comprising a plurality, e.g. at least 4 nucleotide or nucleotide analogue building blocks. Preferably, the oligonucleotide comprises 6-100, e.g. 20-40 building blocks. The nucleotide or nucleotide analogue building blocks may comprise nucleoside or nucleoside analogue subunits connected by inter-subunit linkages. The nucleoside subunits include deoxyribonucleoside subunits, ribonucleoside subunits and/or analogues thereof, particularly sugar- and/or nucleobase-modified nucleoside analogues. Further, the oligonucleotides may comprise non-nucleotidic building blocks and/or further terminal and/or side-chain modifications.

In preferred sugar-modified subunits the 2'-OH of a ribonucleoside subunit is replaced by a group selected from OR, R, halo, SH, SR, $NH_2$, NHR, $NR_2$ or CN, wherein R is $C_{1-6}$ alkyl, $C_{2-6}$ alkenyl or $C_{2-6}$ alkynyl and halo is F, Cl, Br or I. In further preferred sugar-modified subunits, the ribose may be substituted, e.g. by another sugar, for example a pentose such as arabinose. This sugar modification may be combined with 2'-OH modifications as described above, such as in 2'-fluoroarabinonucleoside subunits. Still further preferred sugar-modified subunits include locked nucleosides (LNA) or 2',3'-seco-nucleosides (UNA). In preferred nucleobase-modified nucleosidic building blocks, a non-standard, e.g. non-naturally occurring nucleobase, is used instead of a standard nucleobase. Examples of non-standard nucleobases are uracils or cytosines modified at the 5-position, e.g. 5-(2-amino)propyl uracil or 5-bromouracil; hypoxanthine; 2,6-diaminopurine; adenines or guanines modified at the 8-position, e.g. 8-bromoguanine; deazanucleosides, e.g. 7-deazaguanine or 7-deazaadenine; or O- and N-alkylated nucleobases, e.g. $N^6$-methyladenine, or $N^6,N^6$-dimethyladenine. Further suitable nucleobase analogues may be selected from universal nucleobase analogues such as 5-nitroindole.

The inter-subunit linkage between subunits may be a phosphodiester linkage or a modified linkage, e.g. a phosphorothioate, phosphorodithioate, methylphosphonate, phosphoramidate, boranophosphate, or another modified linkage known to a skilled person in the art.

The oligonucleotide may be selected from deoxyribonucleotides, ribonucleotides and oligonucleotide analogues. The deoxyribonucleotides, ribonucleotides and/or oligonucleotide analogues may be chemically modified at the nucleoside and/or ribose subunit of the analogue, deoxyribonucleotide, ribonucleotide and/or oligonucleotide. Analogues of desoxyribonucleotides or ribonucleotides may comprise at least one desoxyribonucleoside or ribonucleoside subunit and at least one modified nucleosidic subunit and/or at least one modified inter-subunit linkage, e.g. as described above. Oligonucleotide analogues may also consist in their entirety of modified nucleosidic subunits.

The oligonucleotide may be a single-stranded molecule or a double-stranded molecule. Double-stranded oligonucleotides may comprise completely or partially complementary strands. Double-stranded molecules may be blunt-ended or comprise at least one overhang, e.g. a 5'- or 3'-overhang. Overhangs, if present, are preferably located at the distal end of the molecule (with regard to the triphosphate/triphosphate analogue group). Double-stranded oligonucleotides may also comprise a hairpin-structure, wherein the duplex is closed by a loop at the distal end thereof (with regard to the triphosphate/triphosphate analogue group). The loop may comprise nucleotide and/or non-nucleotide building blocks, for example diol-based building blocks such as ethylene glycol moieties, e.g. tri(ethylene)glycol or hexa(ethylene) glycol; propane-1,3-diol; dodecane-1,12-diol; or 3,12-dioxa-7,8-dithiatetradecane-1,14-diol.

In a preferred embodiment, double-stranded molecules are blunt-ended, particularly at the proximal end thereof (with regard to the triphosphate/triphosphate analogue group).

According to an especially preferred embodiment the oligonucleotide is double-stranded, wherein each strand of the double strand has a length of at least 19 nucleotides. A blunt-ended double-stranded oligonucleotide of such a length is especially preferred. According to a further preferred embodiment each strand of the oligonucleotide has a length of at least 19 to 50 nucleotides, 19 to 30 nucleotides, 20 to 30 nucleotides, 22 to 28 nucleotides, especially preferred 22 to 26 nucleotides.

The oligonucleotide may comprise further terminal and/or side-chain modifications, e.g. cell specific targeting entities covalently attached thereto. Those entities may promote cellular or cell-specific uptake and include, for example lipids, vitamins, hormones, peptides, oligosaccharides and analogues thereof. Targeting entities may e.g. be attached to modified nucleobases or non-nucleotidic building blocks by methods known to the skilled person.

According to a preferred embodiment modifications establish and/or enhance the selectivity of the oligonucleotide towards a given target. In a particularly preferred embodiment the RIG-I selectivity of the oligonucleotide is established or enhanced. Methods to determine the RIG-I selectivity of a given oligonucleotide are described herein in detail (cf. Examples) and/or are known to the person skilled in the art.

According to another preferred embodiment the chemical modifications maintain or enhance the chemical stability of the oligonucleotide. A person skilled in the art knows methods for determining the chemical stability of a given oligonucleotide. Such methods are also described, e.g., in the Examples.

According to a preferred embodiment the chemical modifications of the oligonucleotide are independently selected from the group comprising halogenation, in particular F-halogenation, 2'-O-alkylation, in particular 2'-O-methylation, and/or phosphorothioate modifications of internucleotide linkages. Particularly F-halogenation and phosphorothioate modifications increase the stability of the oligonucleotide, while 2'-O-methylation establishes or increases RIG-I selectivity of the oligonucleotide. 2'-O-methylations are also able to modify the immunogenicity of RNA. In a preferred embodiment an oligonucleotide, only comprises one or two 2'-O-methylations per strand, more preferably one 2'-O-methylation per strand.

The 2'-F substitution is particularly preferred. At the 2' position of the ribose the hydroxyl group is substituted for fluoro. 2'-F substitutions in RNAs particularly result in an enhanced stability against nuclease digestion. In a further embodiment, a 2'-fluoro-substitution may particularly augment a RIG-I-dependent immune stimulation.

Herein, phosphorothioate compounds in general relate to phosphorothioate modifications of internucleotide linkages.

Phosphorothioate-modified compounds having a modification at a terminal end of the oligonucleotide are especially preferred. During phosphorothioate modification the non-binding oxygen atom of the bridging phosphate is substituted for a sulfur atom in the backbone of a nucleic acid. This substitution reduces the cleavability by nucleases at this position significantly and results in a higher stability of the nucleic acid strand.

In an especially preferred embodiment an oligonucleotide according to the present invention shows F-halogenation, methylation, in particular 2'-O-methylation, as well as phosphorothioate modifications, in particular at a terminal end of the oligonucleotide.

The identification patterns of a given oligonucleotide depend on the sequence and the length of an oligonucleotide and can be determined for each given oligonucleotide. A person skilled in the art is well aware how to carry out this determination.

As explained above already, such methods for determining RIG-I selectivity and/or stability of a given oligonucleotide are described in detail in the present application.

The oligonucleotide of formula (I) or (IV) comprises a triphosphate/triphosphate analogue group. In this group, $V_1$, $V_3$ and $V_5$ are independently selected from O, S and Se.

Preferably, $V_1$, $V_3$ and $V_5$ are O. $V_2$, $V_4$ and $V_6$ are in each case independently selected from OH, $OR^1$, SH, $SR^1$, F, $NH_2$, $NHR^1$, $N(R^1)_2$ and $BH_3^-M^+$. Preferably, $V_2$, $V_4$ and $V_6$ are OH. $R^1$ may be $C_{1-6}$ alkyl, $C_{2-6}$ alkenyl, $C_{2-6}$ alkynyl, $C_{2-6}$ acyl or a cyclic group, e.g. a $C_{3-8}$ cyclo(hetero)alkyl group, a $C_{3-8}$ cyclo(hetero)alkenyl group, phenyl or $C_{5-6}$ heteroaryl group, wherein heteroatoms are selected from N, O and S. Further, two $R^1$ may form a ring, e.g. a 5- or 6-membered ring together with an N-atom bound thereto. $R^1$ may also comprise substituents such as halo, e.g. F, Cl, Br or I, $O(halo)C_{1-2}$ alkyl and—in the case of cyclic groups—$(halo)C_{1-2}$ alkyl. $M^+$ may be an inorganic or organic cation, e.g. an alkali metal cation or an ammonium or amine cation.

$W_1$ may be O or S. Preferably, $W_1$ is O. $W_2$ may be O, S, NH or $NR^2$. Preferably, $W_2$ is O. $W_3$ may be O, S, NH, $NR^2$, $CH_2$, CHHal or $C(Hal)_2$. Preferably, $W_3$ is O, $CH_2$ or $CF_2$. $R^2$ may be selected from groups as described for $R^1$ above. Hal may be F, Cl, Br or I.

According to an especially preferred embodiment $V_1$, $V_2$, $V_3$, $V_4$, $V_5$, $V_6$, $W_1$, $W_2$ and $W_3$ are O.

The triphosphate/triphosphate analogue group is preferably attached to a terminus of the oligonucleotide. Preferably, the group is attached to the 5'-terminus of the oligonucleotide, particularly to the 5'-OH-group of the 5'-terminal sugar thereof.

As defined herein, Z represents a capture tag or H. The capture tag Z can be functionally defined by a series of plausible examples as presented below. A general rule may be: Z has to allow a convenient purification and it should be removable under conditions which are compatible with pppRNA stability requirements. A person skilled in the art is able to determine without undue burden whether a given tag fulfils the functional definition or not. Thus, a person skilled in the art is aware of such capture tags, in particular with regard to the detailed examples given in the present application.

According to a preferred embodiment the capture tag Z is selected from a long-chain aliphatic residue, a partner of a non-covalent high-affinity binding pair, a reactive chemical entirety, Q or $NHC_2-C_{24}$alkyl, Q being preferably selected from H, amino acids, amino acid analogues, $C_1-C_{24}$alkyl, preferably $C_{12}-C_{24}$alkyl, peptides and lipids. However, according to an especially preferred embodiment Z is decyl, i.e. $C_{10}$ alkyl.

The capture tag Z according to the present invention is a moiety capable of non-covalently or covalently interacting with a capture reagent under conditions which allow separation for compounds comprising the capture tag, e.g. the oligonucleotide (I) from other species, which do not contain the capture tag. Preferably, the capture reagent is an immobilized reagent or a reagent capable of being immobilized.

Suitable capture tags are for instance long-chain, e.g. C8-24, preferably C13-24, more preferably C13-C14 aliphatic alkyl residues such as octadecyl or other lipidic/lipophilic residues such as e.g. cholesteryl, tocopheryl or trityl and derivatives thereof. However, according to an especially preferred embodiment Z is a decyl residue. In this case, the tagged triphosphate entity can be captured and purified on a solid phase by standard reversed phase chromatography, e.g. RP-HPLC, or by hydrophobic interaction chromatography (HIC). The capture tag may also be a perfluoroalkyl entity, e.g. a 4-(1H,1H,2H,2H-perfluorodecyl)benzyl or a 3-(perfluorooctyl)propyl residue for specific capture of the modified oligo-triphosphate on a Fluorous Affinity support such as is commercially available from Fluorous Technologies, Inc.

In another embodiment, the capture tag may be a first partner of a non-covalent high-affinity binding pair, such as biotin, or a biotin analogue such as desthiobiotin, a hapten or an antigen, which has a high affinity (e.g. binding constant of 10-6 l/mol or less) with the capture reagent, which is a second complementary partner of the high-affinity binding pair, e.g. a streptavidin, an avidin or an antibody.

In yet another embodiment, the capture tag may be a first partner of a covalent binding pair, which may form a covalent bond with the capture reagent, which is a second complementary partner of the covalent binding pair, wherein the covalent bond may be a reversible or an irreversible bond. In this embodiment, the capture tag component Z may be a reactive chemical entity such as an azide or alkynyl group enabling covalent reaction with a capture reagent that contains a complementary reactive group, e.g. an alkynyl or azido moiety, respectively, in the case of the Husigen 3+2 cycloaddition reaction (the so-called "click-reaction" that is Cu(I) catalyzed or a variant thereof that proceeds without Cu(I) ions via release of severe ring strain in e.g. cyclooctyne derivatives). A specific example for Z—Y—X in such a case would be propargylamino.

In another embodiment, the capture tag component may be a chemical entity which contains an additional nucleophilic group, for instance a second amino group in an NH2-Y—XH type reagent. A wide range of suitable electrophilic Z reagent such as cholesterol, chloroformiate or biotin N-hydroxy succinimide active esters may then be used to introduce the tagging group while the oligonucleotide is attached to the solid phase, thus significantly extending the scope of the tagging reaction.

In a preferred embodiment the capture tag is a long-chain alkyl residue, a perfluoroalkyl entity, an azide or an alkynyl group.

In a further embodiment of the present invention, the oligonucleotide may carry a second capture tag at a different position, e.g. at the 3'-terminus. The first and the second capture tags are preferably selected as to allow purification by two orthogonal methods to enable recovery of extremely high purity material. For example the first capture tag may be a lipophilic group, which interacts with a suitable chromatographic support and the second capture tag may be biotin, which interacts with streptavidin.

The second capture tag may be conveniently introduced by performing the synthesis using a modified CPG (controlled glass support) for oligoribonucleotide synthesis.

Y represents a chemical bond or a linker, e.g. an alkylene, preferably a C1-6-alkylene linker, more preferably a C2-5-alkylene linker, or aralkylene linker, optionally comprising heteroatoms or heteroatom-containing groups, such as O, S, NH, C=O or C=S, and/or optionally comprising C=C or C≡C bonds. According to an especially preferred embodiment Y is a bond.

In another preferred embodiment the linker is a polyalkylene oxide, preferably a poly-C2-C6-alkylene oxide, more preferably a poly-C2-C3-alkylene oxide. The number average molecular weight of the linker may be in the range from 30-800 g/mol, preferably from 40-450 g/mol, more preferably from 40-250 g/mol. The linker may be [—CH2CHR4-O-]n with n=1-10, preferably n=1-7, more preferably n=2-5, and even more preferably n=3. R4 may be H or C1-6-alkyl. Further preferred embodiments of Y are shown in FIG. 4. In a preferred embodiment R4 is H.

According to an especially preferred embodiment, X is NH or O, Y is —K—$((CHR_1)_m$—$CH_2$—$O)_n$—R—, or $-(O-(CHR_3)_{m3}-CH_2)_{n1}-(O-(CHR_2)_{m2}-CH_2)_{n2}-(O-(CHR_1)_{m1}-CH_2)_{n3}-$, and K is O or NH, m, $m_1$, $m_2$ and $m_3$ is independently 1 to 12, preferably 1 to 8, more preferably 1 to 5, and even more preferably 1 to 3, n, $n_1$, $n_2$ and $n_3$ is independently 0 to 20, preferably 0 to 10, more preferably 0 to 5, and even more preferably 0 to 3, and $R_1$, $R_2$ and $R_3$ is independently is H, $C_{1-6}$ alkyl, $C_{2-6}$ alkenyl, $C_{2-6}$ alkynyl, $C_2$-$C_6$-acyl or a cyclic group, each optionally substituted and R is $C_{1-6}$ alkyl, $C_{2-6}$ alkenyl, $C_{2-6}$ alkynyl, $C_2$-$C_6$-acyl or a cyclic group, each optionally substituted. Preferably, R is $CH_2CH_2$.

According to an especially preferred embodiment with Y being as defined above, $R_1$ and $R_2$ are H, $n_1$ is O and $n_2$ and $n_3$ are 1. Further preferred embodiments can be taken from FIG. 4.

According to another preferred embodiment as Y is being defined above, $R_1$, $R_2$ and $R_3$ are H and $n_1$, $n_2$ and $n_3$ are 1.

According to a preferred embodiment X is NH, K is NH and Y is $(CH_2CH_2O)_n$ with n as being defined above, wherein K is further substituted with cholesterol-C(O)—, trityl or derivatives thereof.

According to an especially preferred embodiment of the oligonucleotide according to Formula (I) X is NH or O, Y is a bond, and Z is $C_1$-$C_{12}$alkyl or H, preferably $C_{10}$, Q or $NHC_2$-$C_{24}$alkyl, wherein Q is selected from H, amino acids, amino acid analogues, $C_1$-$C_{24}$alkyl, preferably $C_{12}$-$C_{24}$alkyl, peptides and lipids, and $V_1$, $V_2$, $V_3$, $V_4$, $V_5$, $V_6$, $W_1$, $W_2$ and $W_3$ are O.

According to a further preferred embodiment of the oligonucleotide of Formula (I) X is NH or O, Y is a bond, and Z is decyl or H, and $V_1$, $V_2$, $V_3$, $V_4$, $V_5$, $V_6$, $W_1$, $W_2$ and $W_3$ are preferably O.

A further aspect of the present invention relates to a pharmaceutical composition comprising a modified oligonucleotide as defined herein.

The pharmaceutical composition according to the invention may further comprise pharmaceutically acceptable carriers, diluents, and/or adjuvants. The term "carrier" when used herein includes carriers, excipients and/or stabilisers that are non-toxic to the cell or mammal being exposed thereto at the dosages and concentrations employed. Often the physiologically acceptable carriers an aqueous pH buffered solutions or liposomes. Examples of physiologically acceptable carriers include buffers such as phosphate, citrate and other organic acids (however, with regard to the formulation of the present invention, a phosphate buffer is preferred); anti-oxidants including ascorbic acid, low molecular weight (less than about 10 residues) polypeptides; proteins such as serum albumin, gelatine or immunoglobulins; hydrophilic polymers such as polyvinyl pyrrolidone; amino acids such as glycine, glutamine, asparagine, arginine or lysine; monosaccharides, disaccharides, and other carbohydrates including glucose, mannose or dextrins, gelating agents such as EDTA, sugar, alcohols such as mannitol or sorbitol; salt-forming counterions such as sodium; and/or non-ionic surfactants such as TWEEN, polyethylene or polyethylene glycol. According to an especially preferred embodiment the compound of the invention is dissolved in sterile deionized water.

Such a composition and/or formulation according to the invention can be administered to a subject in need thereof, particularly a human patient, in a sufficient dose for the treatment of the specific conditions by suitable means. For example, the composition and/or formulation according to the invention may be formulated as a pharmaceutical composition together with pharmaceutically acceptable carriers, diluents and/or adjuvants. Therapeutic efficiency and toxicity may be determined according to standard protocols. The pharmaceutical composition may be administered systemically, e.g. intraperitoneally, intramuscularly, or intravenously or locally such as intranasally, subcutaneously, intradermally or intrathecally. The dose of the composition and/or formulation administered will, of course, be dependent on the subject to be treated and on the condition of the subject such as the subject's weight, the subject's age and the type and severity of the disease or injury to be treated, the manner of administration and the judgement of the prescribing physician.

In a preferred embodiment the pharmaceutical composition is administered intradermally. It is especially preferred that the composition is administered intradermally via tattooing, microneedling and/or microneedle patches.

The compound according to the present invention is preferably dissolved and diluted to the desired concentration in sterile, deionized water (purified water) and is then applied on the shaved, ethanol-disinfected skin using a pipetting device, and subsequently tattooed into the skin.

For tattooing, for example, the water-based pharmaceutical composition according to the invention is intradermally injected into the skin, using a (medical) tattoo device fitted with a multi-needle (single use) needle-tip (such as a 9-needle, single-use tip).

The typical tattooing procedure is as follows: After the water-based pharmaceutical composition is pipetted onto the shaved and ethanol cleaned skin, it is introduced into the tattoo machine's multi-needle tip by placing the running needle tip (running at a speed of, for example, 100-120 Hz, in particular at 100 Hz) gently on top of the droplet of water-based pharmaceutical composition. Once the droplet of water-based pharmaceutical composition is completely adsorbed in the running needle tip, and hence resides in between the running needles, the running tip is gently moved back and forth over the skin, by holding the now filled needle tip in an exact 90 degree angle to the skin. Using this method, the water-based pharmaceutical composition is completely tattooed into the skin. For 50-100 µl of water-based pharmaceutical composition this typically takes 10-15 seconds, over a skin area of 2-4 square centimeters. The benefit of this treatment over standard single intradermal bolus injection, is that the water-based pharmaceutical composition is evenly injected over a larger area of skin, and is more evenly and more precisely divided over the target tissue: By using a 9-needle tip at 100 Hz for 10 seconds, this method ensures 9000 evenly dispersed intradermal injections in the treated skin.

Of course, a person skilled in the art may deviate from and adjust the procedure, depending on the patient or part of the body to be treated. The microneedling procedure may be carried out in close analogy to the tattooing procedure. However, with microneedling the tattoo needle-tip is replaced by a microneedling tip, which ensures more superficial intradermal administration. The water-based pharmaceutical composition is in principle pipetted onto the shaved and ethanol cleaned skin and then administered intradermally using the microneedling tip, in analogy to the tattoo procedure. Microneedling does not have necessity to prior adsorption of the pharmaceutical composition in between the microneedling needles.

Additionally, it is envisioned that microneedle patches coated with, or otherwise harbouring, the pharmaceutical composition can be used for transdermal/intradermal delivery. This has the specific advantage that the intradermal delivery of the pharmaceutical composition can be carried out safely by the recipient him-/herself in without the need for a hospital visit and/or medical specialist tattooing/microneedling intervention. This can significantly add flexibility to treatment schemes, allow highly personalized treatment regimens, lower treatment-associated pain, and lower treatment cost. These patches can be constituted of, but not be limited to, dissolving- or non-dissolving microneedle patches for the time-controlled-, sustained- or bolus transdermal delivery of the pharmaceutical composition.

Another aspect of the present invention relates to a method of preparing an oligonucleotide according to any of claims 1-15, comprising the steps
(a) reacting a compound of formula (IIa)

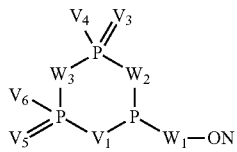

wherein V1, V3, V5, V4, V6, W1, W2, W3, and ON are as defined above, wherein ON is protected by at least one protection group, with an oxidizing agent to obtain a compound of formula (IIb)

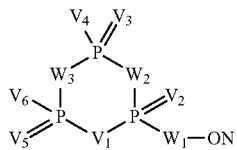

wherein V1, V3, V5, V2, V4, V6, W1, W2, W3 and ON are as defined above, wherein ON is protected by at least one protection group,
(b) reacting a compound of formula (IIb) with a capture tag agent of formula (III),

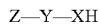 (III), wherein X, Z, and Y are as defined above, wherein X is preferably O, to obtain a reaction product comprising the oligonucleotide of formula (I), and
(c) deprotection of the at least one ON protection group, and
(d) contacting the reaction product of step (c) with a capture reagent capable of interacting with the capture tag, wherein the contacting takes place under conditions which allow separation of the oligonucleotide (I) from other species contained in said reaction product.

An embodiment, wherein X is O, is especially preferred.

During the inventive method the ON oligonucleotide comprises at least one protection group. The use of protective groups according to the present invention aims in particular at protecting the 2'-OH groups ribose subunit of the applied oligonucleotide. A person skilled in the art knows which protection groups are suitable for synthesis, especially a person working in the field of nucleotide synthesis. Protective groups at the 2'-OH position of the ribose subunit of the oligonucleotide are preferred. In a preferred embodiment of the present invention at the 2'-position of the ribose unit fluoride-labile protective groups are used.

Especially preferred are 2'-O-TBDMS or 2'-O-TOM protective groups. In a particularly preferred embodiment the TBDMS protective group is applied.

Particularly during the synthesis of compounds with X=O, which have an enhanced Z—Y—X—PPP binding stability, a broad spectrum of deprotection conditions may lead to the 2'-OH protective groups being cleaved off.

All known deprotection reagents are suitable to cleave off the TBDMS protective group. In particular, the following reagents may be applied:
(a) triethylamine-trihydrofluoride optionally in combination with a polar solvent,
(b) trialklylamine, triethylamine-trihydrofluoride and a polar solvent,
(c) pyridine-HF and other adducts of hydrofluoride of organic nitrogen bases,
(d) ammonium fluoride,
(e) tetra-n-butyl-ammonium fluoride,
(f) tetramethyl-ammonium fluoride, and other tetraalkylammonium fluorides and combinations thereof.

Step (c) is preferably carried out under conditions which do not cause degradation of the triphosphate moiety, e.g. as described in detail below.

Step (a) of the method of the invention comprises the reaction of cyclic P(V)—P(V)—P(III) species of formula (IIa) with an oxidizing agent. The compound of formula (IIa) may be obtained according to standard methods as described by Ludwig et al, 1989, supra and Gaur et al., 1992, supra, namely by reacting the 5'-terminal OH-group of an oligonucleotide with a trifunctional phosphitylating agent, e.g. 2-chloro-4H-1,3,2-benzodioxaphosphorin-4-one under suitable conditions, e.g. in the presence of base (pyridine or diisopropylmethylamine) in a suitable solvent such as dioxane or dichloromethane, and subsequent reaction with pyrophosphate ($W_3$=O) or a modified pyrophosphate ($W_3$ is different from O, e.g. $CH_2$, $CCl_2$, NH or $CF_2$). Preferably, a tri-n-butylammonium salt of the pyrophosphate or modified pyrophosphate in DMF is used. The resulting cyclic P(III)—P(V) intermediate (IIa) is then oxidized under anhydrous conditions, e.g. with a peroxide, such as t-butyl hydroperoxide, cumene hydroperoxide, (10-camphorsulfonyl)oxaziridine. Alternatively, phenylacetyldisulfide ($V_2$=S), or borane-diisopropylethylamine complex ($V_2$=$BH_3$) can also be employed respectively, to give the corresponding cyclic 5'-triphosphate/triphosphate analogue of formula (IIb). Reference in this context is also made to WO 96/40159 or WO 2009/060281, the contents of which are herein incorporated by reference.

Reaction step (a) may take place with an oligonucleotide in solution or with an oligonucleotide bound to a solid phase, e.g. an organic resin or glass, such as CPG. The oligonucleotide may further comprise protecting groups, e.g. sugar- or nucleobase protecting groups that are well known to the skilled person. Preferred examples of protecting groups are 2-cyanoethyl for the internucleoside phosphodiester or phosphorothioate, tert-butyldimethylsilyl, triisopropylsilyloxymethyl or bis(acetoxyethoxy)methyl for the ribose 2'-hydroxyl group, 4-t-butylphenoxyacetyl or phenoxyacetyl, acetyl, isobutyryl, benzoyl for the exocyclic amino groups of the nucleobases. More preferably, step (a) is carried out with a solid-phase bound oligonucleotide.

According to step (b) of the method of the invention, compound (IIb) is reacted with a capture tag agent of formula (III)

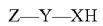 (III)

wherein X is a group selected from NH, NR³, O or and X and Y are as defined above. R³ is defined as described above for R¹.

In particular, in case for X being O an agent of limited nucleophilicity such as decanol can be used for ring opening (cf. FIG. 1, step 4). Such a step can be carried out at room temperature, e.g. for 48 h, and allows conversion of the cyclotriphosphate to the desired triphosphate γ-ester.

According to step (c) the ON protection groups are cleaved off.

During step (c), for example, the deprotective reagents (a) and (b) specified above may be followed by deprotection condition with X=O over a period of 20 min to 180 min, more preferably 60 min to about 150 min, in particular about 120 min, at 60-70° C., in particular about 65° C. If X=NH, such reactions are excluded due to different binding stability or can only be carried out under significantly worse reaction parameters, e.g. over a period of 40 h at RT.

Step (d) of the method of the present invention comprises contacting the reaction product of step (b), with a capture reagent capable of interacting with the capture tag Z under conditions which allow separation of the capture tag containing oligonucleotide (I) from other species contained in the reaction product. Before step (d), the solid phase bound oligonucleotide (I) is cleaved from the solid phase and deprotected, i.e. the protection groups are partially or completely removed. The capture reagent is preferably immobilized on a suitable support, e.g. a chromatographic support. In order to provide separation of capture tag containing oligonucleotide (I) from non-capture tag-containing species, the reaction products from step (b) are cleaved from a solid phase and deprotected, if necessary, and subjected to a separation procedure, preferably a chromatographic separation procedure based on the interaction of the capture tag Z with the capture reagent. During the separation step, the purity of the oligonucleotide (I), which is generally in the range of 25-70% for the crude material depending upon the length and complexity of the sequence, may be increased to 90%, 91%, 92%, 93%, 94%, 95% or more. For toxicity studies a purity of >85% is desirable, whereas in late stage clinical trials the purity should be in the range of at least 90-95%. Thus, the present invention provides a way to obtain a high purity pppRNA as would be required for human clinical trials.

In step (d), the capture tag and the capture reagent capable of interacting therewith are preferably selected from (i) a hydrophobic or fluorinated group and a chromatographic material with affinity for hydrophobic or fluorinated groups, e.g. a reversed phase material or a fluorous affinity support; (ii) a first partner of a non-covalent high-affinity binding pair and a second complementary partner of a non-covalent high-affinity binding pair, (iii) a first partner of a covalent binding pair and a second complementary partner of a covalent binding pair, where the first and second partner form covalent bonds.

The capture tag is functionally defined below by a series of plausible Examples. A general rule may be:

Z has to allow a convenient purification, and it should be removable under conditions which are compatible with pppRNA stability requirements.

Additionally, the method may further comprises step (e) removing the capture tag to obtain an oligonucleotide of Formula (IV). According to a preferred embodiment, for X=O a compound of Formula (IV)a or (IV)b

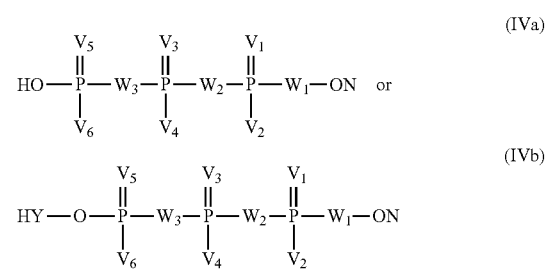

and for X=NH a compound of Formula (IV)a

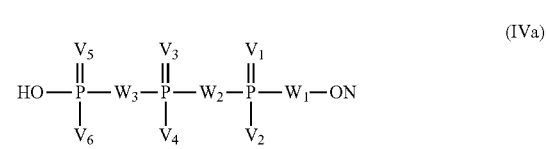

is obtained.

Step (e) has to be compatible with stability requirements of the triphosphate end product and with stability requirements of the interribonucleotide bond. It may comprise cleavage by mildly acidic conditions when X is NH, cleavage with silver ions when X is S, cleavage by a thiol such as dithiothreitol leading to elimination of thiirane when Y—X—P contains —S—S—CH₂—CH₂—O—P.

In further embodiments the capture tag Z is not or not completely removed. In these embodiments the tagged oligonucleotide as such may have utility, e.g. utility as pharmaceutical agent.

In these embodiments, the reagent Z—Y—XH has to be selected from a subgroup of Z-residues, which are functionally compatible with the structural requirements of the RIG-I sensor. For instance, the Z=decyl-octadecyl, Y=link X=NH or O combination is known to fulfill these requirements.

The triphosphate/triphosphate analogue modified oligonucleotides produced according to the present invention are particularly suitable for pharmaceutical applications due to their high purity. In an especially preferred embodiment, the oligonucleotide (I) or (IV) is an activator of RIG-I helicase. Specific examples of suitable RIG-I activators are disclosed in Schlee et al., 2009, supra, the content of which is herein incorporated by reference.

FIGURE LEGEND

(A) RP-HPLC profiles of
   a) crude reaction mixture containing 48% decyl-O-pppRNA (RT=14 min)
   b) pure decyl-O-pppRNA
      Column: Hamilton PRP-1 4.1×250, 10 μm
      Gradient: 0-100% B in 18 min, A=100 mM TEAB; B=80% methanol, 100 mM TEAB
(B) ESI-MS profile of pure decyl-O-pppRNA recorded using RP-LC/MS (MW calc.: 7987, found: 7968).

Figure 1:
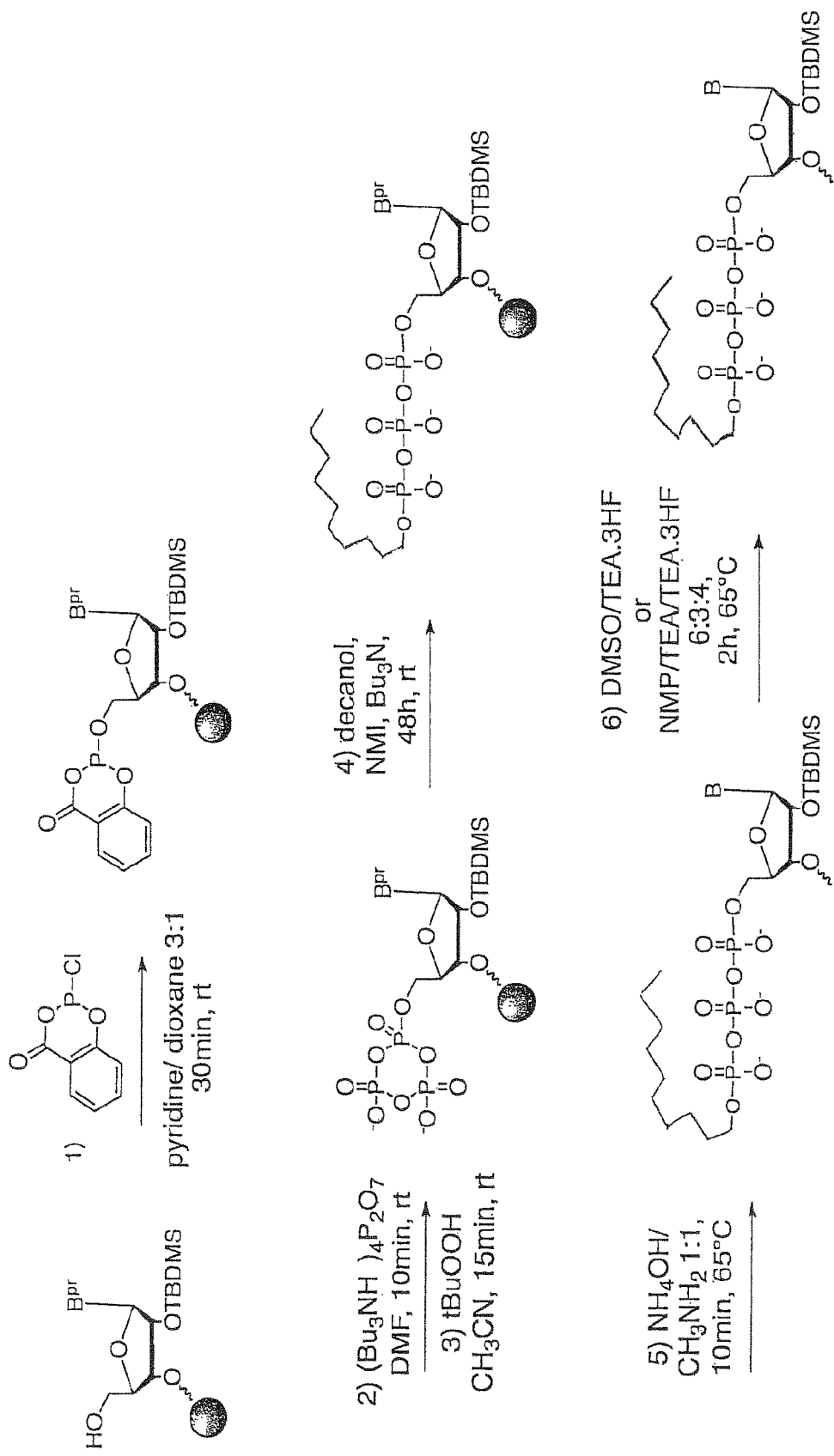
FIG. 1 shows a schematic overview of the synthesis method for oligonucleotide triphosphate ester derivatives.
Figure 2:
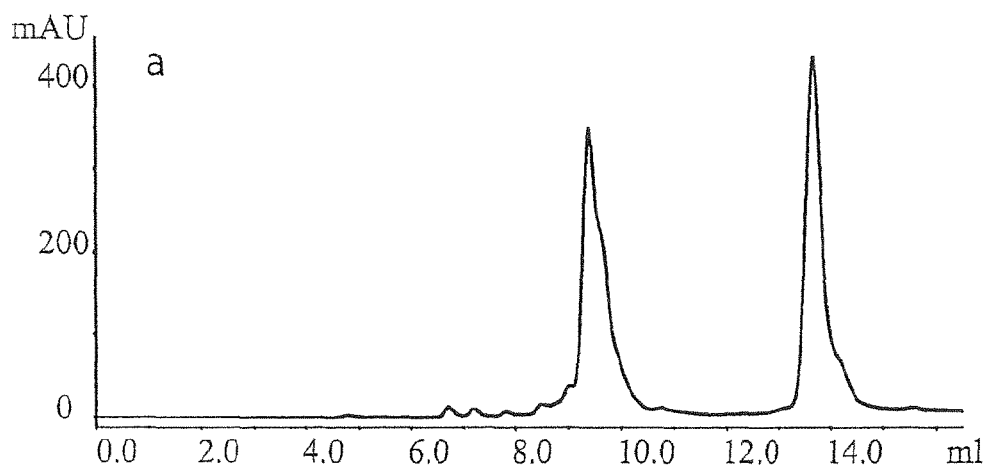
FIG. 2 shows RP-HPLC and ESI-LC/MS analysis of a decyl-O-pppRNA 24mer synthesis (RNA sequence: 5'-GACGCUGACCCUGAAGUUCAUCUU, SEQ ID NO: 1)
Figure 2:
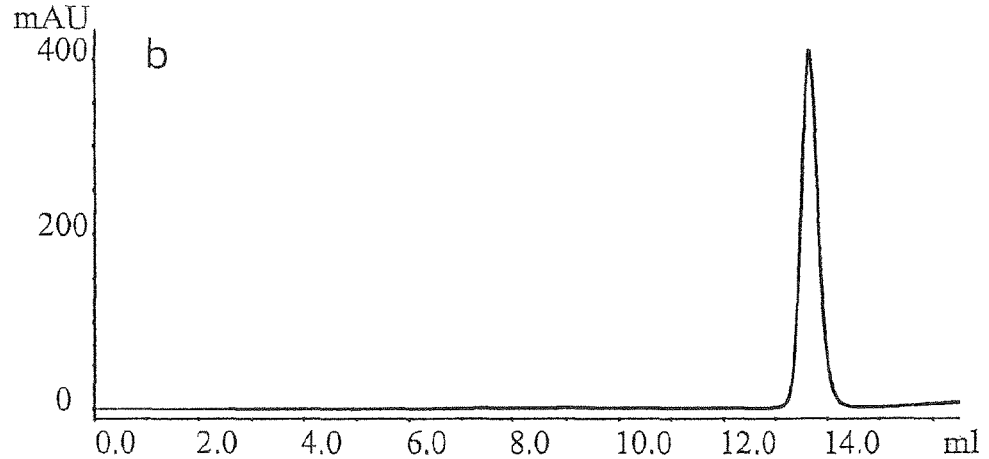
Figure 2:
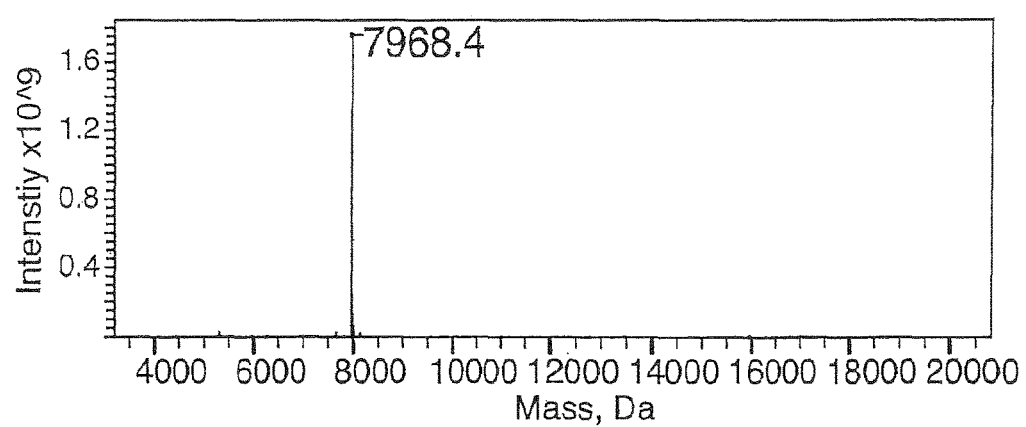
Figure 3:
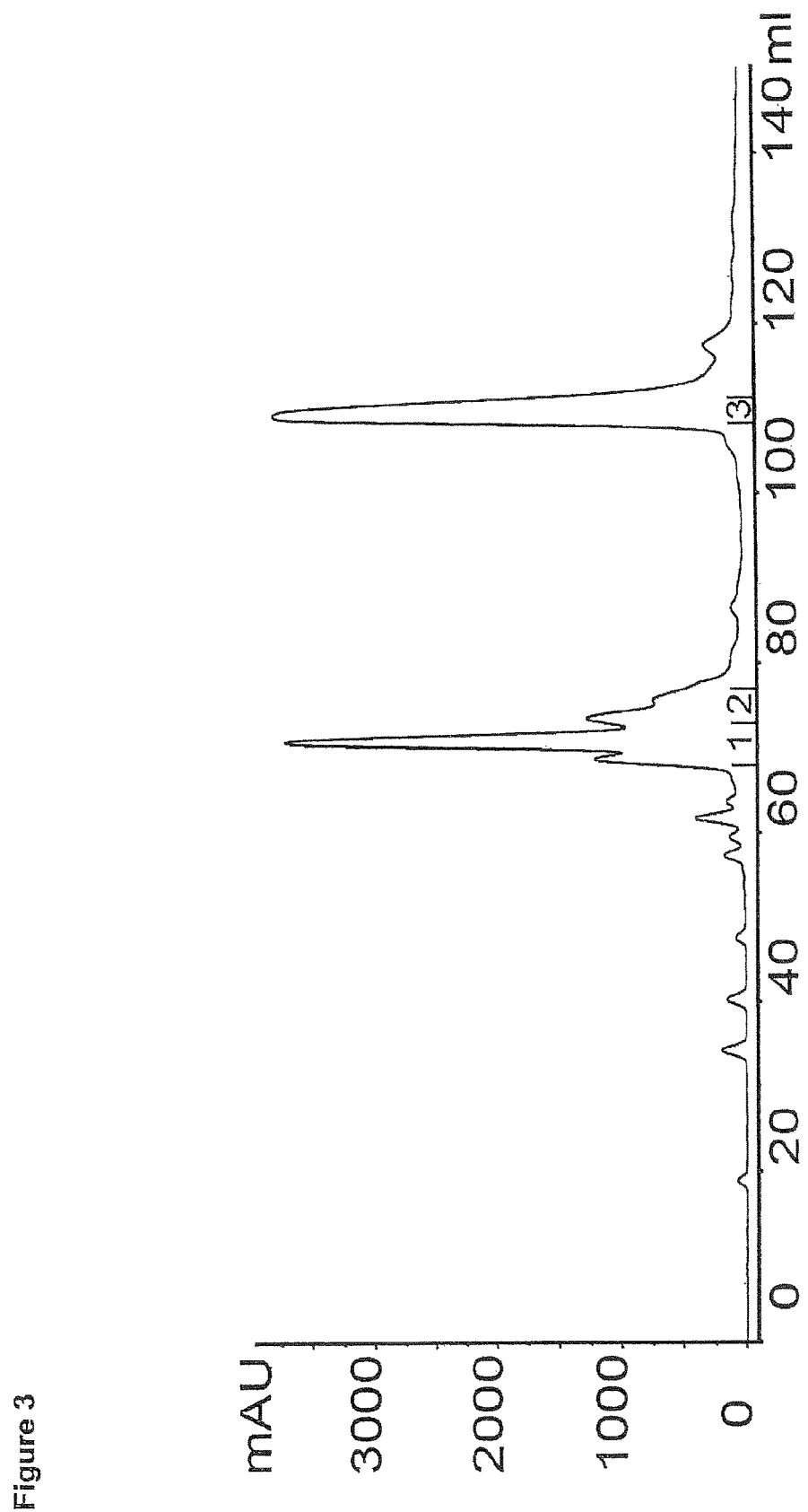

FIG. 3 shows a semipreparative scale RP-HPLC purification of a 1 μmol scale reaction of decyl-O-pppRNA:

Decyl-tagging allows efficient separation of the desired product (fraction3) from non-tagged side products including synthesis failure sequences, full-length nonphosphorylated OH-RNA and nonderivatized pppRNA.
Column: Hamilton PRP-1 7×250 mm, 10 μm
Gradient: 0-80% B in 50 min, A=100 mM TEAB; B=80% methanol, 100 mM TEAB.

Figure 4:
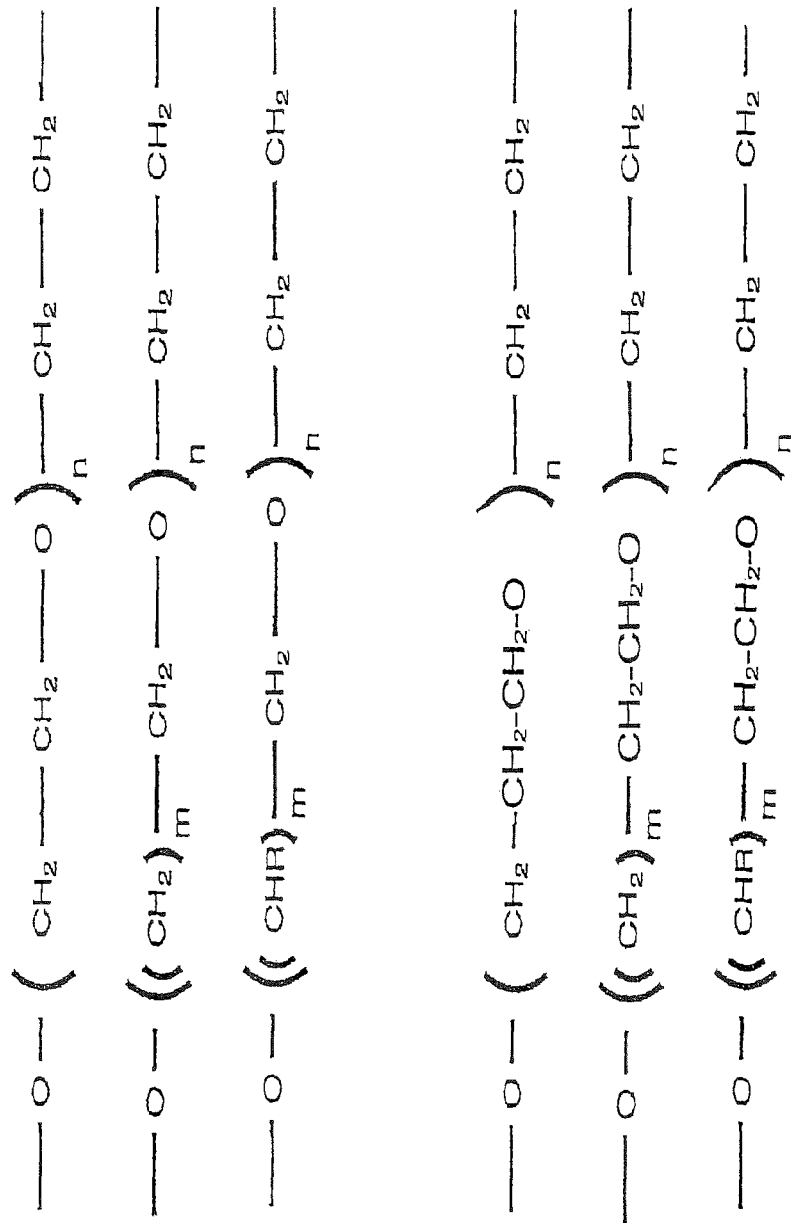

FIG. 4: Especially preferred embodiments of Y.

Figure 5:
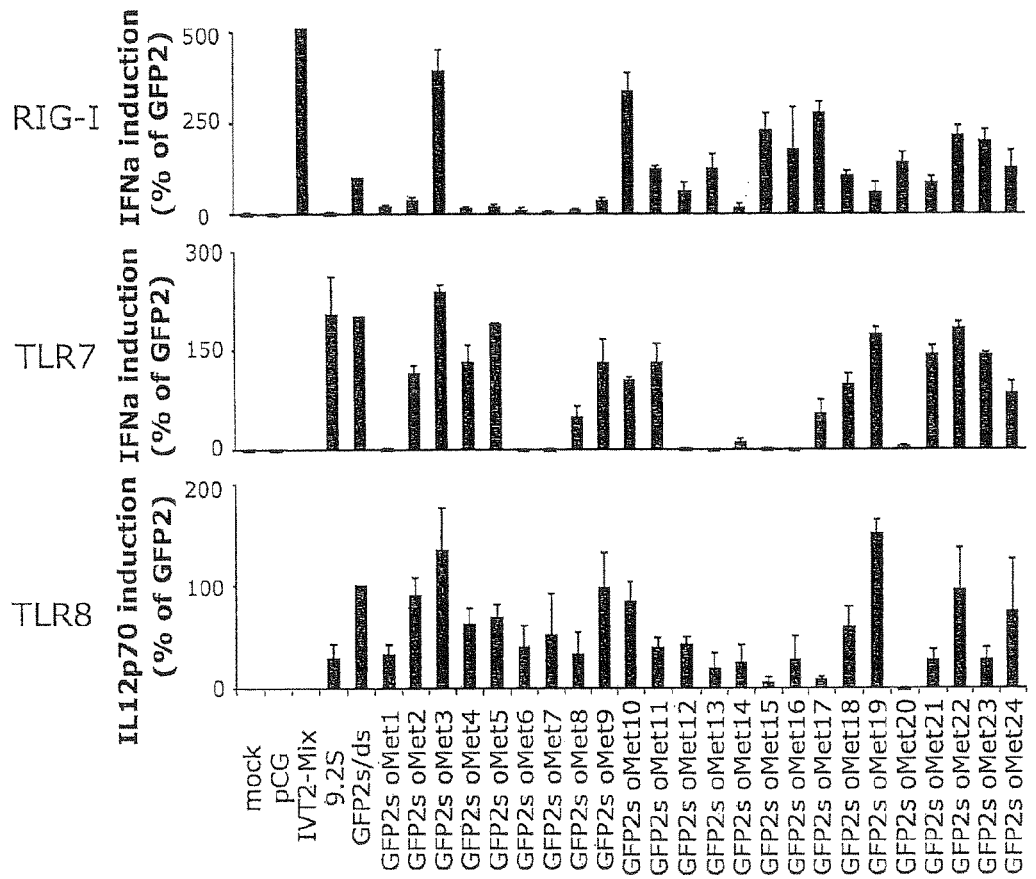
Figure 5:
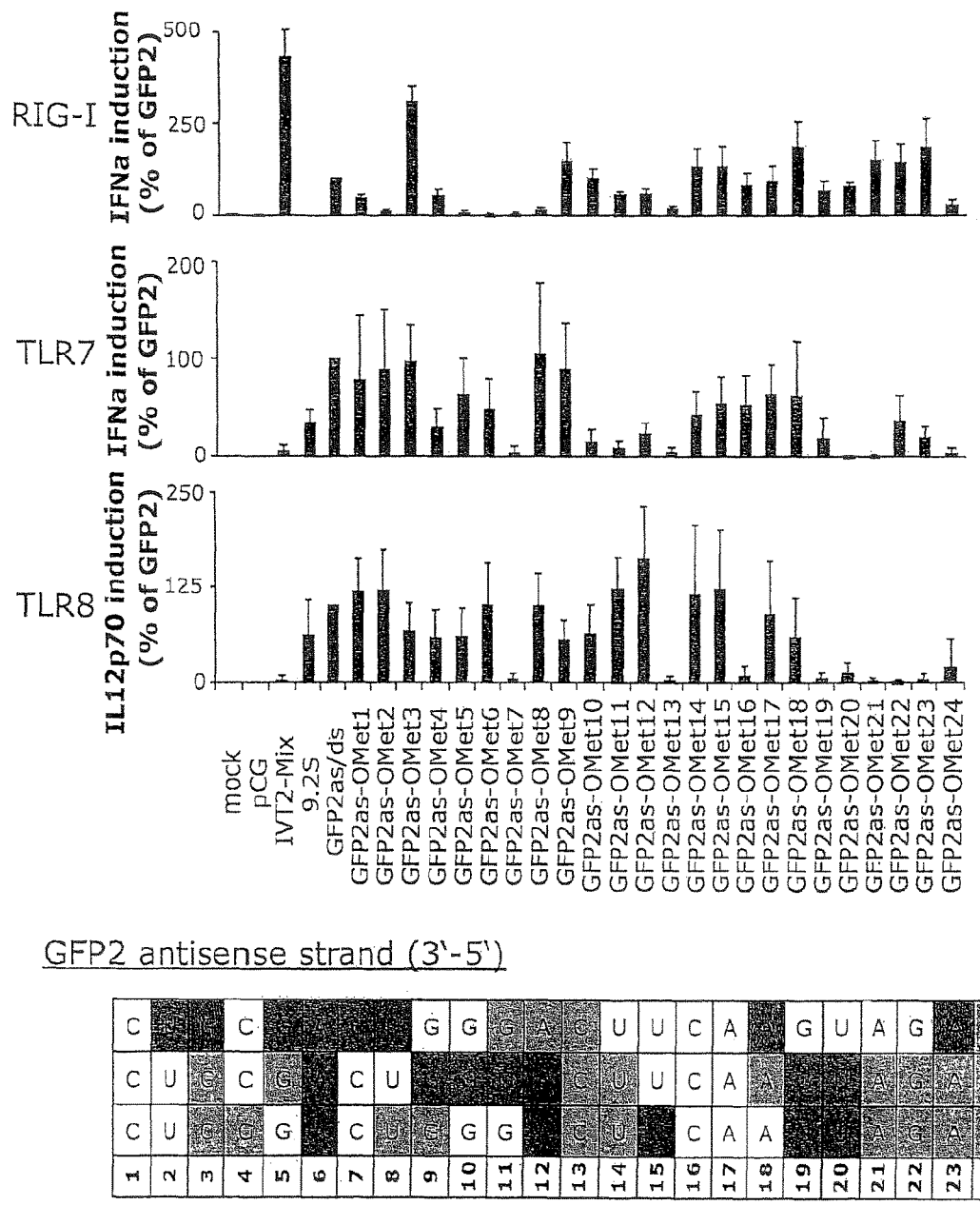

FIG. 5: A screen of 2'-O-methylations resolves positions to introduce RIG-I selectivity.

Figure 6:
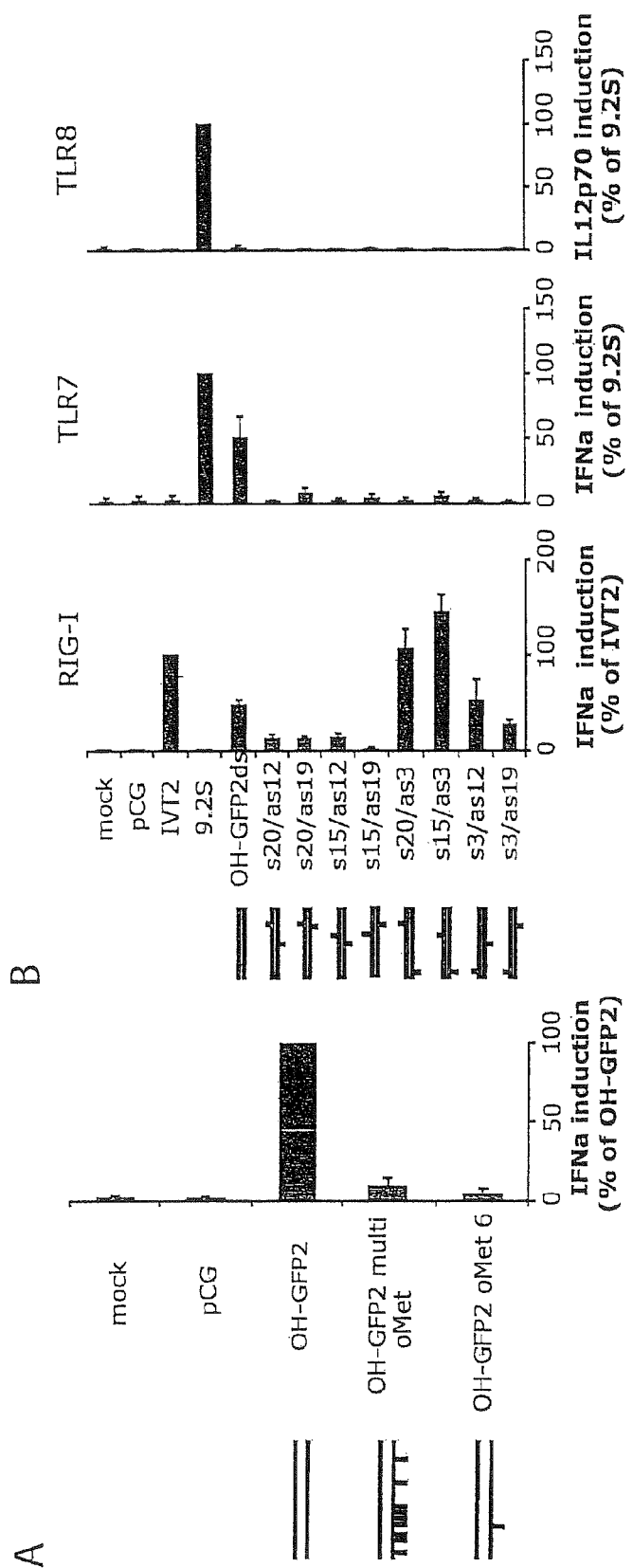

FIG. 6: Methylations render the duplex RIG-I specific and highly active.

Figure 7:
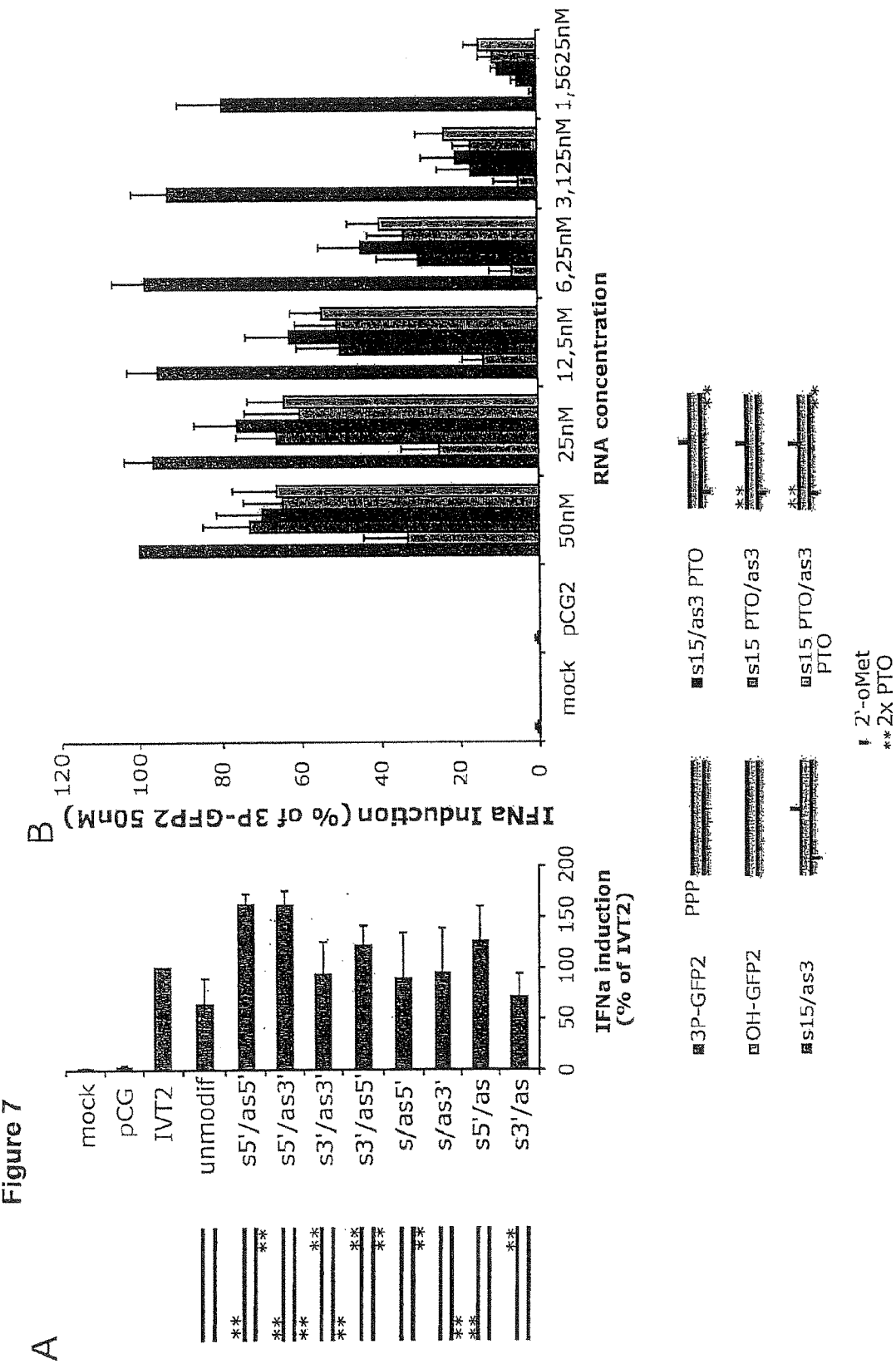

FIG. 7: Terminal phosphorothioates augment immunogenicity of the selective duplex.

FIG. 8: Selected 2'-Fluoro-substitutions augment the RIG-I activation potential of the duplex.

FIG. 9: The multiple modification pattern of OH ds-RNA OH-GFP2 leads to a strong enhancement of RIG-I activation potential.

FIG. 10: Enhancement of immunogenicity by backbone modifications is transferable to a triphosphorylated duplex.

FIG. 11: Shows a schematic overview of the method of the invention using diethylenglycolmonobutylether as an example for alkylpolyethylenglycols as nucleophilic ring opening reagent.

FIG. 12: RP-HPLC purification of C4-DEG-pppRNA crude reaction mixture containing 45% C4-DEG-pppRNA (peak at 88.4 ml gradient volume) and 50% pppRNA (peak at 77.5 ml) Column: Hamilton PRP-1 7×250 mm, 10 μm Flow rate 3 ml/min.
Gradient: 1-80% B in 50 min, A=0.1M TEAB; B=80% Methanol 0.1 M TEAB FIG. 13: MALDI-TOF spectra corresponding C4-DEG-pppRNA after HPLC purification The correct mass peak is observed at m/z 7972.6 (A).

FIG. 14 shows the synthesis scheme of pppRNA using a lipophilic polyether composite tag.

FIG. 15 shows the HPLC purification and MALDI data related to FIG. 14 (RNA sequence: 5'-GACGCUGACCCUGAAGUUCAUCUU, SEQ ID NO: 2)

(A) RP-HPLC purification of C11-CONH—$CH_2CH_2CH_2$—(O—$CH_2CH_2)_2$—O—$CH_2CH_2CH_2$—NHpppRNA
Column: Hamilton PRP-1 4.1×250 mm, 10 μm
Gradient: 0-80% B in 50 min, A=100 mM TEAB, B=80% methanol, 100 mM TEAB (B) MALDI spectrum recorded from the crude reaction mixture after desalting showing the presence of C11-CONH—$CH_2CH_2CH_2$—(O—$CH_2CH_2)_2$—O—$CH_2CH_2CH_2$NHpppRNA (Mw 8214.8)

(C) MALDI spectrum of the pH=3.8 hydrolysis product of purified C11-CONH—$CH_2CH_2CH_2$—(O—$CH_2CH_2)_2$—O—$CH_2CH_2CH_2$NHpppRNA (Mw 7832.6)

FIG. 16 shows the synthesis scheme of cholesteryl-tagged pppRNA with optional cleavage to the corresponding pppRNA.

FIG. 17 shows the purification and analysis of a cholesteryl-tagged pppRNA (RNA sequence: 5'-GACGCUGACCCUGAAGUUCAUCUU, SEQ ID NO: 3):

(A) RP-HPLC purification of Cholesteryl —CONH—$CH_2CH_2$—(O—$CH_2CH_2)_2$—NH-ppp-RNA Column: Hamilton PRP-1 4.1×250 mm, 10 μm
Gradient: 0-10% B in 5 min, 10% B for 9 min, 10-100% B in 33 min;
A=50 mM TEAB, B=95% methanol, 50 mM TEAB (B) RP-HPLC analysis of pure Cholesteryl —CONH—$CH_2CH_2$—(O—$CH_2CH_2)_2$—NH-ppp-RNA.
Column: Hamilton PRP-1 4.1×250 mm, 10 μm
Gradient: 0-100% B in 18 min, 100% B for 4 min; A=50 mM TEAB, B=95% methanol, 50 mM TEAB (C) MALDI spectrum of pure Cholesteryl —CONH—$CH_2CH_2$—(O—$CH_2CH_2)_2$—NH-ppp-RNA.
The pppRNA peak (7827.3 Da) is due to PN-cleavage during the ionisation process.

EXAMPLES

Example 1: Preparation of 5'-Decyl-O-triphosphate RNA

As outlined in the overview (FIG. 1) the decyl-O-triphosphate RNA synthesis process includes the following synthesis steps:

1-4) 5'-Decyl-O-triphosphate RNA

The support-bound, fully protected 5'OH-RNA (1 μmol) was dried for 3 h under vacuum within a synthesis column and subsequently washed with anhydrous pyridine/dioxane (1:3, v/v, 4 ml). Under argon, a freshly prepared 1M solution of 2-chloro-4H-1,3,2-benzodioxaphosphorin-4-one in dry dioxane (100 μl, 100 μmol) was injected into a flask containing 2 ml of anhydrous pyridine/dioxane (1:3, v/v). The resulting 50 mM phosphitylating solution was drawn into the synthesis column and slowly moved back and forth during a reaction time of 30 min. Next, a tetra(tri-n-butylammonium)pyrophosphate solution was prepared by mixing a 0.5M solution of bis(tri-n-butylammonium)pyrophosphate in DMF (1 ml, 0.5 mmol) and tri-n-butylamine (238 μl, 1 mmol). The pyrophosphate solution was pushed through the column and after expelling and discarding the excess phosphitylating reagent from the column the remaining pyrophosphate solution was pushed back and forth using two syringes. After 10 min the column was washed with anhydrous acetonitrile (3 ml). A 5.5M tert-butyl hydroperoxide solution in decane (300 μl) was dissolved in anhydrous acetonitrile (2 ml) and brought into contact with the synthesis support. After 15 min the column was washed with anhydrous acetonitrile (6 ml). Subsequently, a homogeneous solution of N-methylimidazole (240 μl, 3 mmol), tri-n-butylamine (250 μl, 1.1 mmol) and n-decyl alcohol (2 ml, 10.5 mmol) was repeatedly pushed to and fro through the column and was left to react for 48 h for cyclotriphosphate conversion to decyl-O-triphosphate. The column was washed with anhydrous acetonitrile (6 ml) and treated with 0.1M triethylammonium bicarbonate (TEAB, 2 ml) for 20 min for hydrolysis of unreacted cyclotriphosphate, avoiding unspecific derivatisation during the following deprotection procedure. Following a further wash step with anhydrous acetonitrile (9 ml) the synthesis support was dried in a stream of argon.

5-6) Deprotection & Purification

The 5'-decyl-O-triphosphate oligonucleotide was brought into contact with a freshly prepared solution of 40% aqueous methylamine and concentrated aqueous ammonia (AMA, 1:1, v/v, 2 ml) using two syringes. After 30 min cleavage time the solution was transferred to a clean screw cap vial and the support was rinsed with AMA (1 ml). The combined solution and washing was heated for 10 min at 65° C. After cooling on ice the solution was evaporated to dryness and the residue was dried by co-evaporation with absolute ethanol. For removal of the 2'-O-TBDMS protecting groups treatment with triethylamine trihydrofluoride (TEA.3HF) can be used without significant loss of the modified triphosphate moiety. The decyl-O-triphosphate oligonucleotide was redissolved in a freshly prepared solution of N-methylpyrrolidone/triethylamine/TEA.3HF (NMP/TEA/TEA.3HF, 6:4:3, v/v, 325 µl) and the solution was heated at 65° C. for 2 h. Alternatively, a deprotection solution of TEA.3HF in DMSO (1:1, v/v, 600 µl) could be used. The fully deprotected decyl-O-triphosphate oligonucleotide was precipitated from the deprotection solution using n-butanol and purified by HPLC. The lipophilic decyl-tag allows separation of the decyl-O-triphosphate from impurities that do not contain the tag by using reversed phase chromatography. The reaction product was applied to a 7×250 mm PRP-1 column and separated in a linear gradient from 0 to 100% buffer B in 50 min at a flow rate of 3 ml/min. Buffer A was 100 mM TEAB and buffer B 100 mM TEAB in 80% methanol. The product fractions were collected, evaporated and desalted by repeated co-evaporation with methanol. The residue was dissolved in water and transferred to the sodium form by ethanol precipitation in the presence of 0.3 M sodium chloride.

Example 2: Preparation of a 5'-pppRNA gamma 2-(2-Butoxyethoxy)ethyl-ester (C4-DEG-pppRNA)

Figure 11:
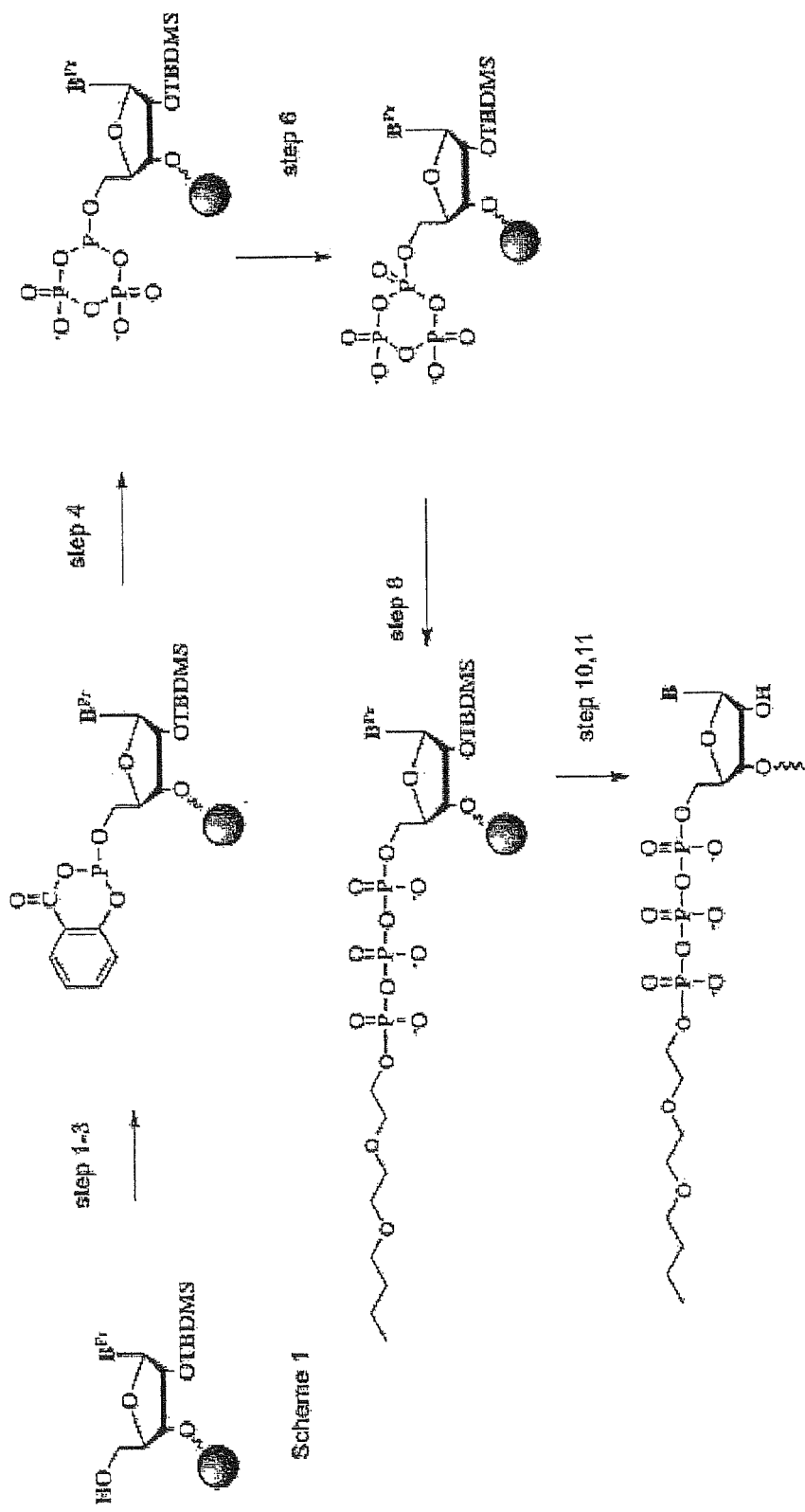
Figure 12:
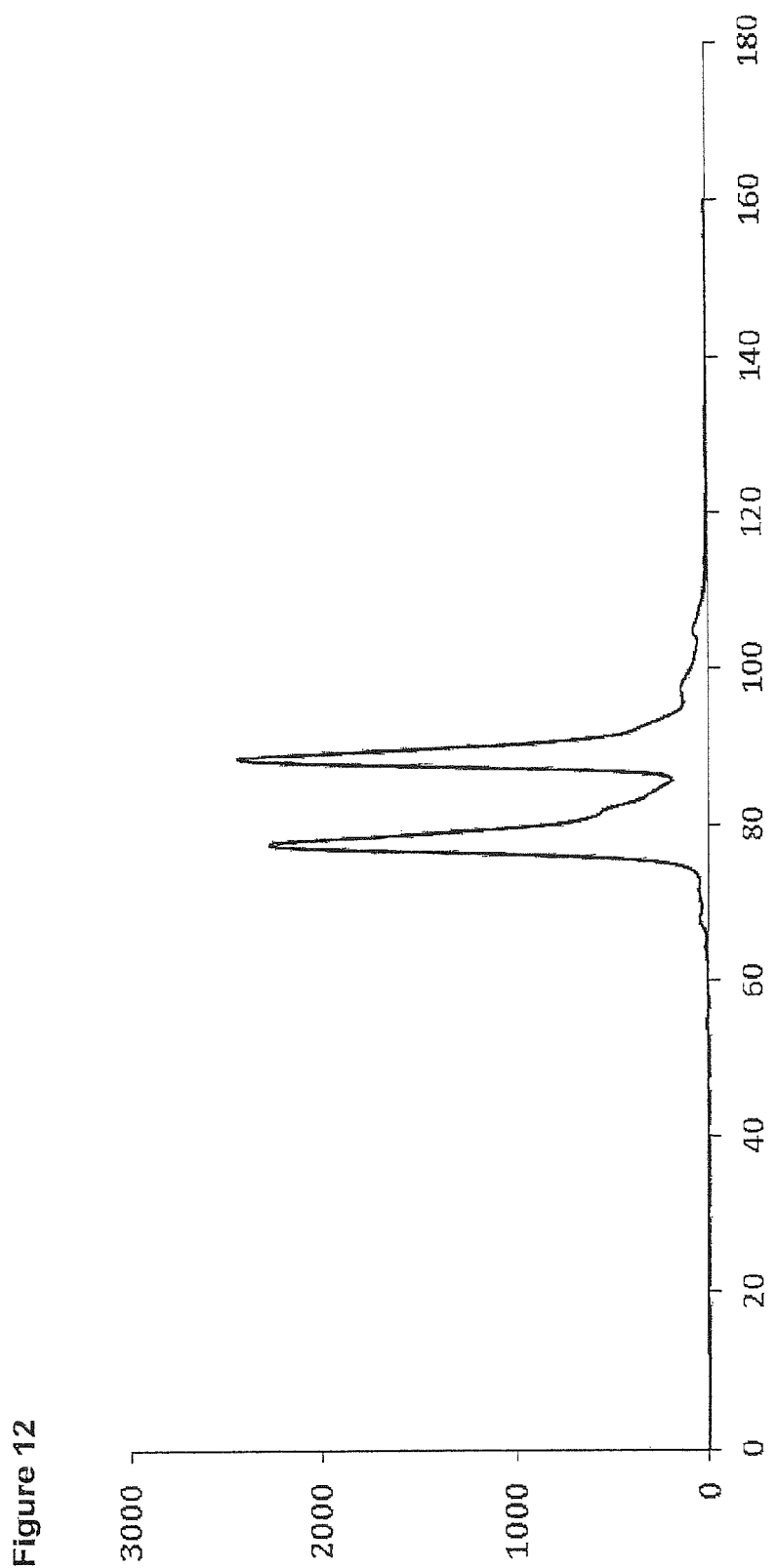
Figure 13:
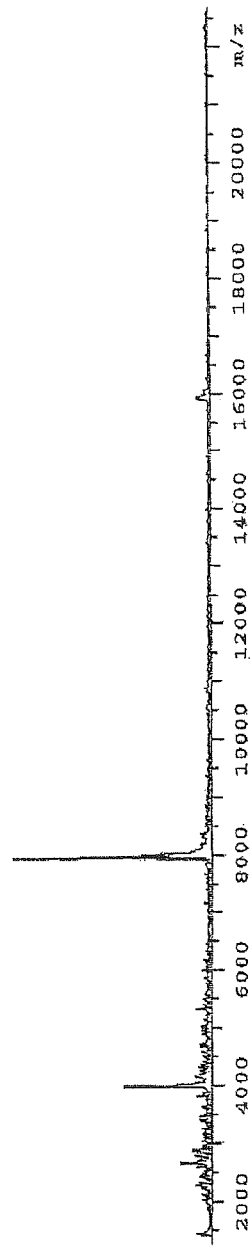

An overview of the reaction scheme described in Example 2 is shown in FIG. 11.

Step 1:
Dissolve 203 mg (1 mmol) of 2-chloro-4H-1,3,2-benzodioxaphosphorin-4-one in 1 mL of dry dioxane in a 10 mL septum vial under argon.

Step 2:
Dry the synthesis column containing the fully protected RNA that has been detitrylated and thoroughly washed with acetonitrile, in vacuum for 12 h. Wash the column contents thoroughly by repeatedly drawing in and expelling 2 mL of anhydrous dioxane/pyridine solution, 3:1 (v/v) in an argon atmosphere.

Step 3:
Add into a vial first 2 mL of pyridine/dioxane, 3:1 v/v followed by 100 µL of 1 M 2-chloro-4H-1,3,2-benzodioxaphosphorin-4-one solution in dry dioxane to give a 50 mM solution of the phosphitylating reagent, e.g. 2-chloro-4H-1,3,2-benzodioxaphosphorin-2-one, in dioxane/pyridine, 3:1 (v/v). Homogenize the solution by gently shaking. Start the reaction by drawing the 2-chloro-4H-1,3,2-benzodioxaphosphorin-4-one solution through the synthesis column from the vial.

During the reaction, repeatedly draw in and expel the 2-chloro-4H-1,3,2-benzodioxaphosphorin-4-one containing solution from the synthesis column, in order to allow thorough contact and good mixing with the solid phase supported RNA. A 30 min reaction time usually gives near quantitative reaction of the free 5'-OH group of the support bound oligomer in the 20-40 nt range.

Step 4:
After a 30 min reaction time expel the dioxane/pyridine solution containing the excess phosphitylating agent into a waste container, fill a new syringe with a vortexed mixture of 1 mL of 0.5 M (Bu3NH)2 pyrophosphate in dry DMF and 238 µL (1 mmol) of dry Bu3N to give a 0.5 M (Bu3N)4 pyrophosphate solution. Push this solution through the column thereby replacing the dioxane/pyridine solution. The large excess of the pyrophosphate ensures a quantitative conversion of the intermediate to the P(III)—P(V) cyclic anhydride IIa.

Step 5:
Wash the column with 3 mL of CH3CN to remove the DMF and excess PPi, and to fill the column reactor with dry CH3CN.

Step 6:
Dissolve 300 µL of t-BuOOH (5.5 M solution in decane, Sigma-Aldrich) in 2 mL of anhydrous CH3CN to give an approximately 0.7 M homogeneous solution. Contact the synthesis support with this solution for 15 min in order to obtain the oxidized P(V) cyclic anhydride IIb.

Step 7:
Wash the column with 3 mL of dry CH3CN to remove the excess peroxide and fill it with dry CH3CN.

Step 8:
Contact 2 ml dry 2-(2-Butoxyethoxy)ethanol (Diethylene glycol monobutyl ether) containing 0.1 M N-methylimidazole and 0.1 M tri-n-butylamine with the support in the column. Contact time of the CPG with the alcohol should be at least 48 hrs at room temperature.

Step 9:
Wash the column thoroughly with 9 mL acetonitrile, then contact the column with 2 ml 0.1 M TEAB (triethylammonium bicarbonate), solution in water for 1 hr in order to hydrolyse unreacted cyclotriphosphate.

Step 10—First Stage of the Deprotection:
Pass 1 mL of deprotection solution (40% aq. methylamine/conc. aq. ammonia 1:1 v/v. AMA reagent) through the support for 2-3 times. After a contact of 30 min transfer the solution into a new vial. Wash the support with same volume of AMA deprotection solution and combine the washings. Heat the combined solution and washings for 10 min at 65° C. After cooling on ice, concentrate the solution to a volume of 300-500 µL, then evaporate to dryness.

Step 11—Removal of the 2'-O-TBDMS Protecting Groups:
Dry the residue by addition and coevaporation of 300 µL of dry EtOH, add 1 mL of dry 1 M TBAF (tetra-n-butylammonium fluoride) in THF, seal tightly and put on a shaker for 16 h. Quench the reaction with 1 mL of sterile aqueous 1 M TEAB (triethylammonium bicarbonate), and desalt it on a NAPTM-25 (Nucleic Acid Purification) column using sterile water as eluent. Filtration through a sterile 2 µm filter may be necessary at this step. Combine and evaporate the UV-absorbing fractions to a volume of 150 µL, add 100 mL of 1 M TEAB pH8 and store the solution frozen at −20° C. until the HPLC purification can be performed.

Step 12—HPLC Purification:
The reaction product from an 1 µmol scale reaction mixture from step 11 was loaded into a 7×25 mm PRP-1 column (Hamilton). Purification was performed using a linear gradient buffer B from 0 to 80% in 50 min at a flow rate of 3 mL/min. Buffer A is 100 mM TEAB and buffer B is 100 mM TEAB in methanol/water 8:2 v/v. A typical example of a 24-mer purification is shown in FIG. 3. A combination of a 4 atom alkyl tag and diethyleneglycol residue is sufficient for near base line separation from pppRNA. Fraction corresponding to the peak at 88.4 ml were combined, evaporated on a rotary evaporator and desalted by several coevaporations with dry methanol.

Example 3: Derivatisation of pppRNA Using Lipophilic Polyether Composite Tags with Preformed Lipophilic Polyether Amines Example 3 employs lipophilic polyether amines of the structure ZY—H to generate ZYNHpppRNA Part A: Economical Large Scale Preparation of the Lipophilic Polyether Amine This procedure can be performed without flash column chromatography and is generally applicable for the synthesis of monoamides from water-soluble diamines and methyl esters of lipophilic carboxylic acids.

Figure 14:
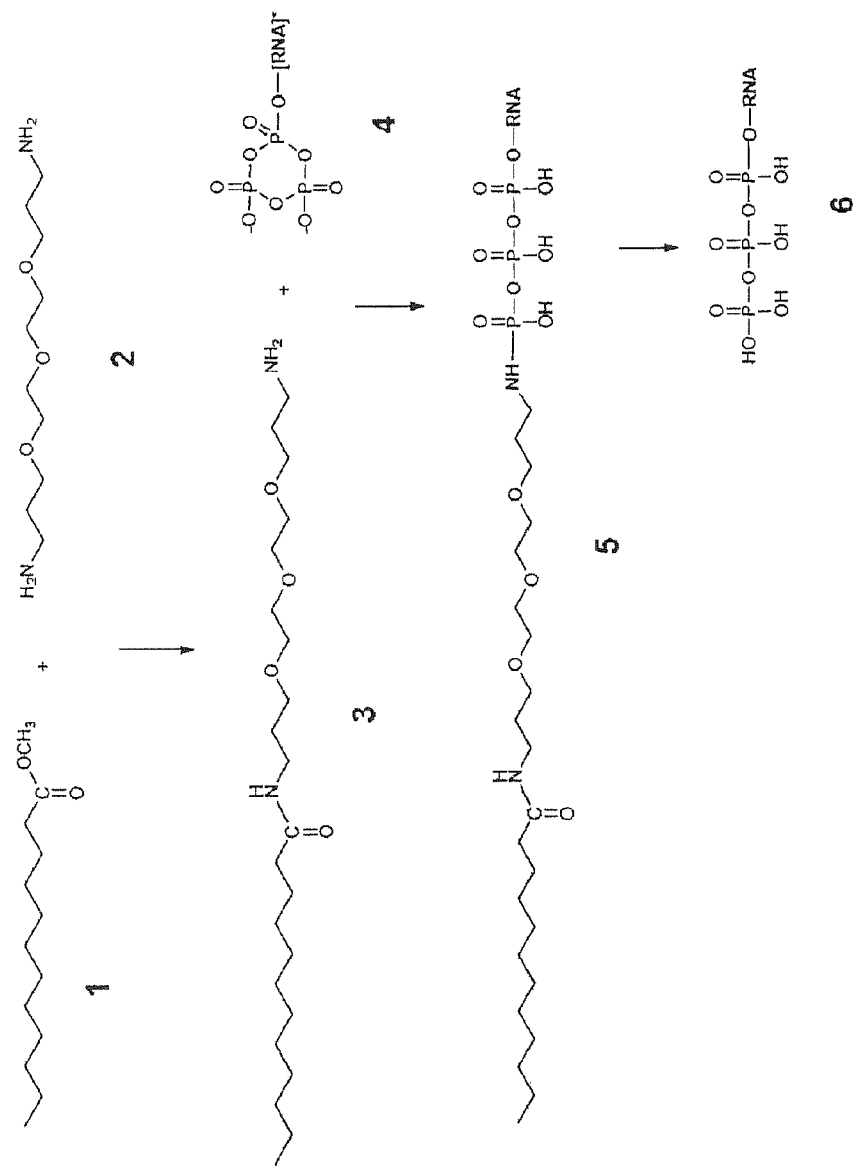

Synthesis of N-Lauryl-4,7,10-trioxa-1,13-tridecanediamine (compound 3, FIG. 14): 4,7,10-trioxa-1,13-tridecanediamine (43.8 ml, 200 mmol) was dissolved in 32.5 ml Methanol. Lauric acid methyl ester (4.92 ml, 20 mmol) was added slowly with stirring and the closed flask was kept at room temperature for 5 days. Methanol was removed from the reaction mixture on a rotary evaporator and the residue was dissolved in 100 ml Ethylacetate.

The excess of the diamine was removed by extraction with water (2*120 ml) followed by concentrated sodium chloride (2*100 ml). The ethylacetate phase was evaporated and the residual oil was crystallized upon standing at −20° C. to give 6.8 g (17 mmol) of pure N-Lauryl 4,7,10-trioxa-1,13-tridecanediamine.

Figure 15:
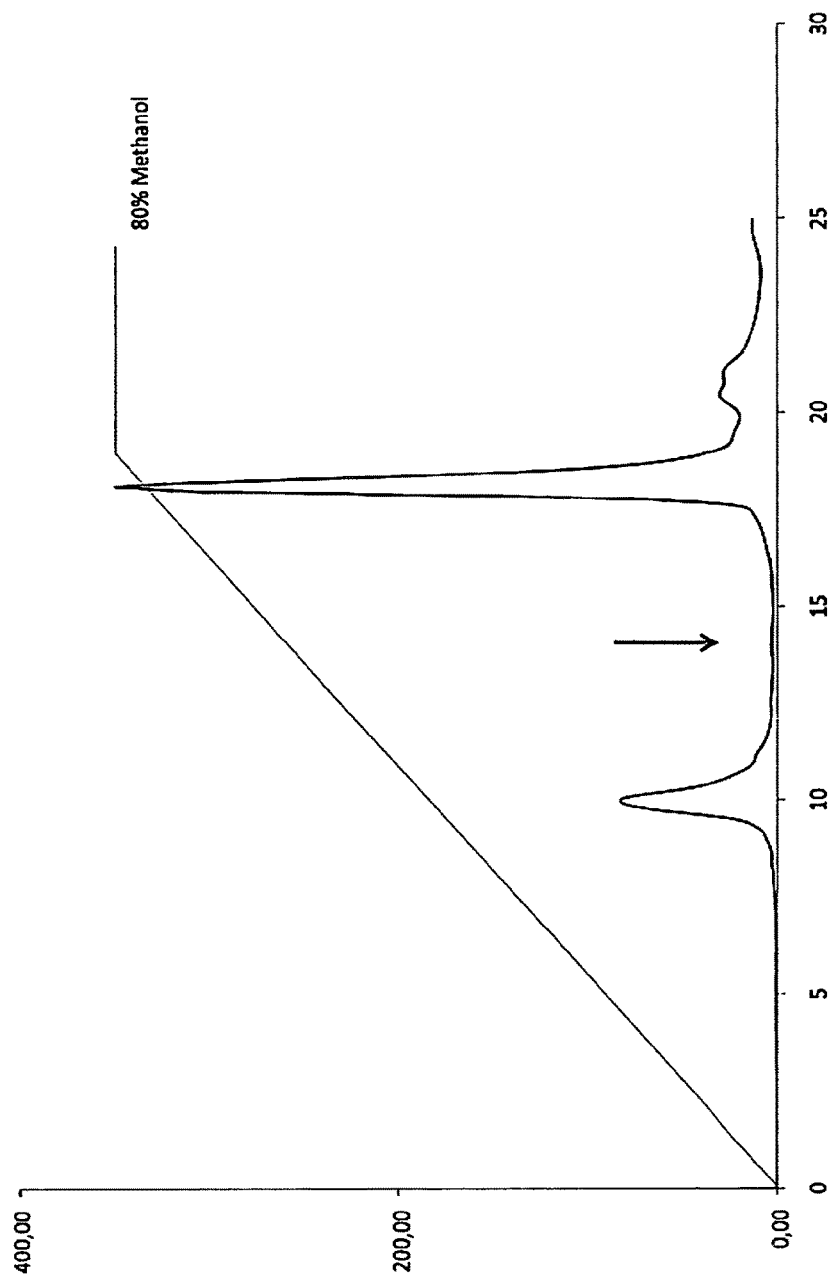
Figure 15:
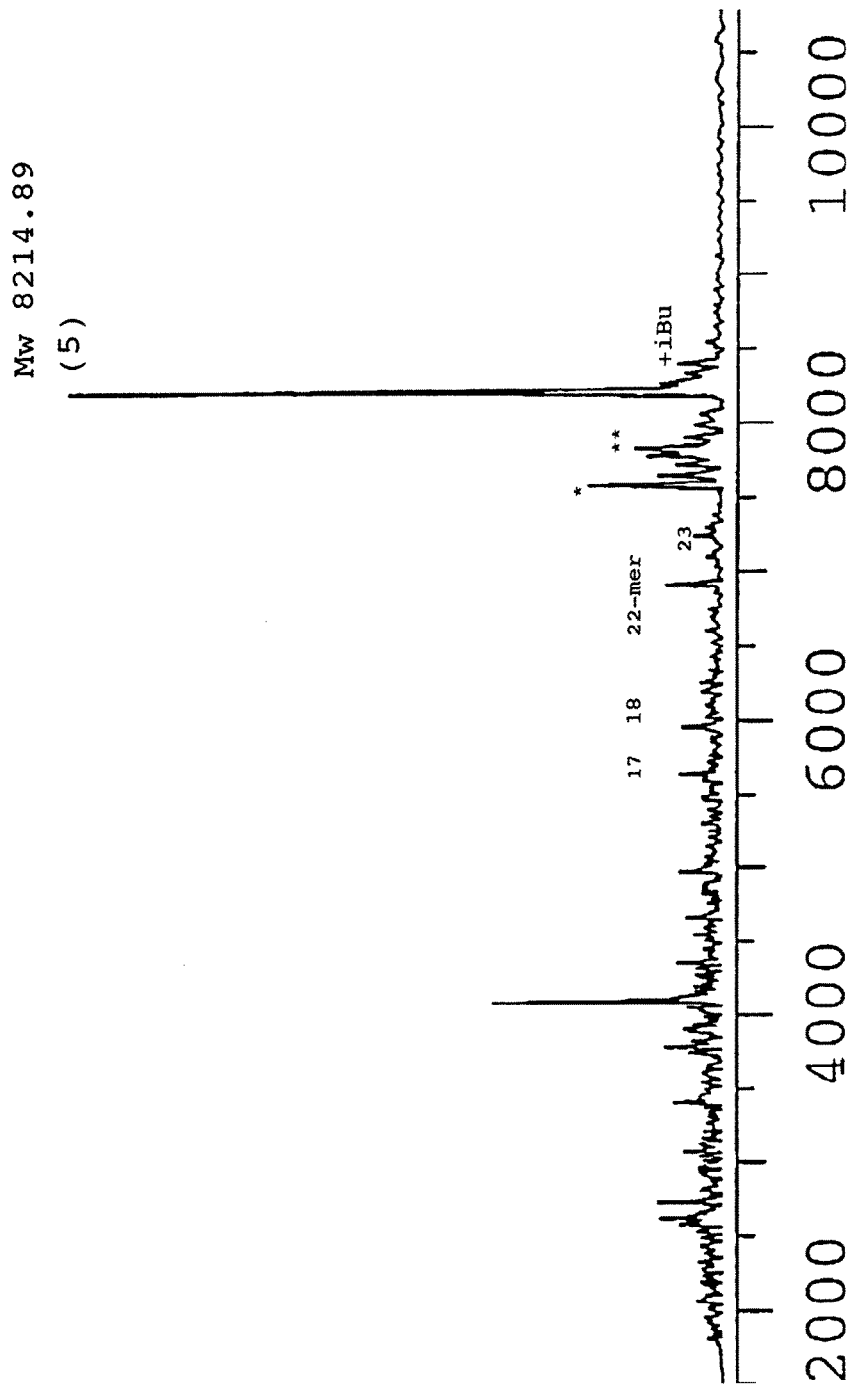
Figure 15:
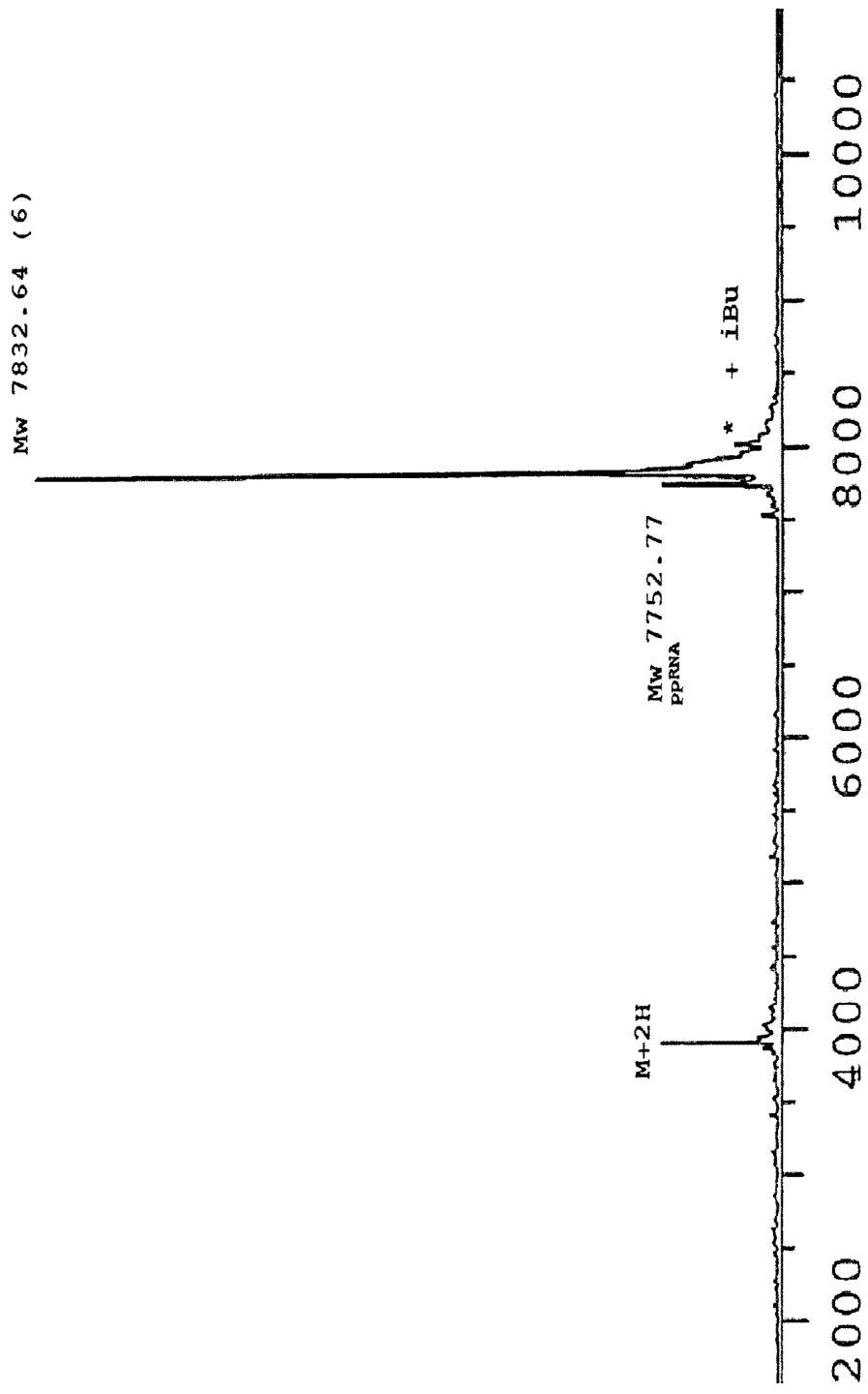

Part B: Ring Opening Reactions on the CPG Bound RNA Cyclotriphosphate with N-Lauryl-4,7,10-trioxa-1,13-tridecanediamine CPG bound RNA cyclotriphosphate (compound 4, FIG. 14) was synthesized according to steps 1-7 in the previous example 2. The ring opening reaction of solid phase immobilized RNA cyclotriphosphate was performed with 0.08 M solution of N-Lauryl-4,7,10-trioxa-1,13-tridecanediamine in acetonitrile. The acetonitrile solution was contacted with the CPG for 3 hrs a at room temperature, the support was then washed with 10 ml dry acetonitrile and flushed dry with argon. Cleavage from the support, deprotection and further HPLC processing was performed exactly according to steps 10-12 of example 2. Product 5 was eluted at 75% Methanol concentration (FIG. 15A). MALDI spectral analysis of the reaction mixture confirms the structure of compound 5 (Mw 8214.8 Da, FIG. 15B).

Optionally, the purification tag may be removed to obtain the corresponding triphosphate oligonucleotide: 100 nmol n-lauryl substituted gamma amid (compound 5, FIG. 14) was dissolved in 400 µl of pH 3.8 deprotection buffer in a 2 ml Eppendorf tube an the sealed tube was heated at 60° C. for 70 min. These conditions result in quantitative cleavage of the phosphoramidate bond of compound 5, with no degradation of the triphosphate moiety. The reaction mixture was cooled on ice and 14 µL of sterile 5M NaCl solution and 1.2 mL of absolute ethanol was added. The precipitate was collected by centrifugation, washed with cold ethanol, dried on a Speed Vac, dissolved in sterile water and stored frozen at −20° C.

MALDI spectral analysis confirms the expected MW of the pppRNA product (Mw 7832 Da, FIG. 15C).

Example 4: On-Column Approach for the Derivatisation of pppRNA with Lipophilic Polyether Composite Tags Example 4 is a two-step procedure employing on-column derivatisation of an immobilized HYNHpppRNA oligonucleotide to generate ZYNHpppRNA Preparation of Cholesteryl-Tagged Triphosphate RNA (Chl-CONH—$CH_2CH_2$—(O—$CH_2CH_2$)$_2$—NH-ppp-RNA, Compound 4, FIG. 16)

Figure 16:
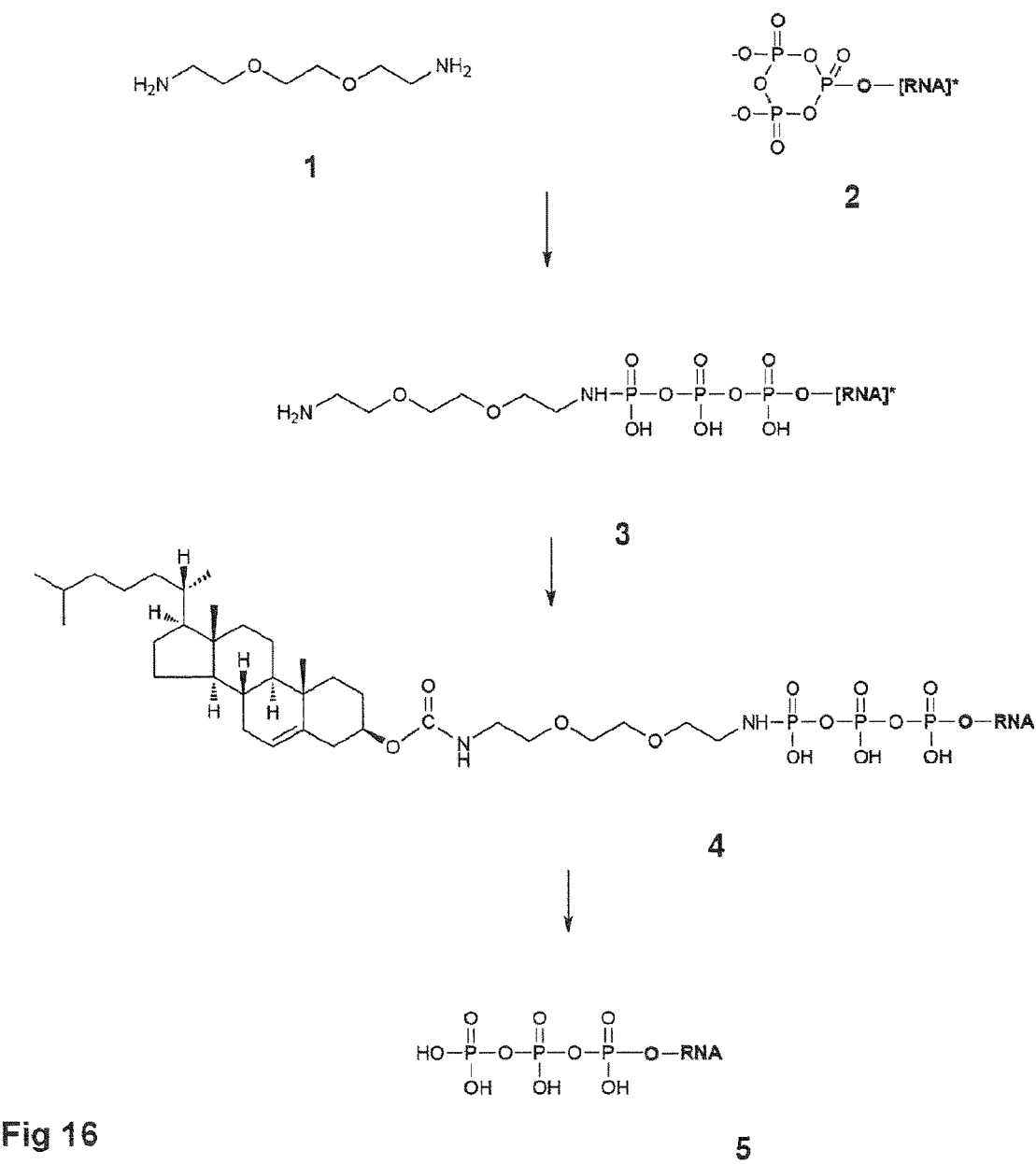

Conjugation of a lipophilic cholesteryl-tag to triphosphate RNA allows efficient separation of the tag-pppRNA product from non-tagged impurities by RP-HPLC. An overview of the reaction scheme for preparation of cholesteryl-tagged triphosphate RNA is shown in FIG. 16. In a first step the support-bound, fully protected 5'OH-RNA was converted into the cyclic triphosphate intermediate (compound 2, FIG. 16) as described in steps 1-7 of example 2. Subsequently, the column was washed with anhydrous acetonitrile (3 ml). 176 µl of 2,2'-(ethylenedioxy)diethylamine (compound 1, FIG. 16; 1.2 mmol) were dissolved in anhydrous acetonitrile (1 ml) and the solution was brought into contact with the support in the column. After 3 min the column was washed with anhydrous acetonitrile (3 ml) and anhydrous dichloromethane (6 ml).

Figure 17:
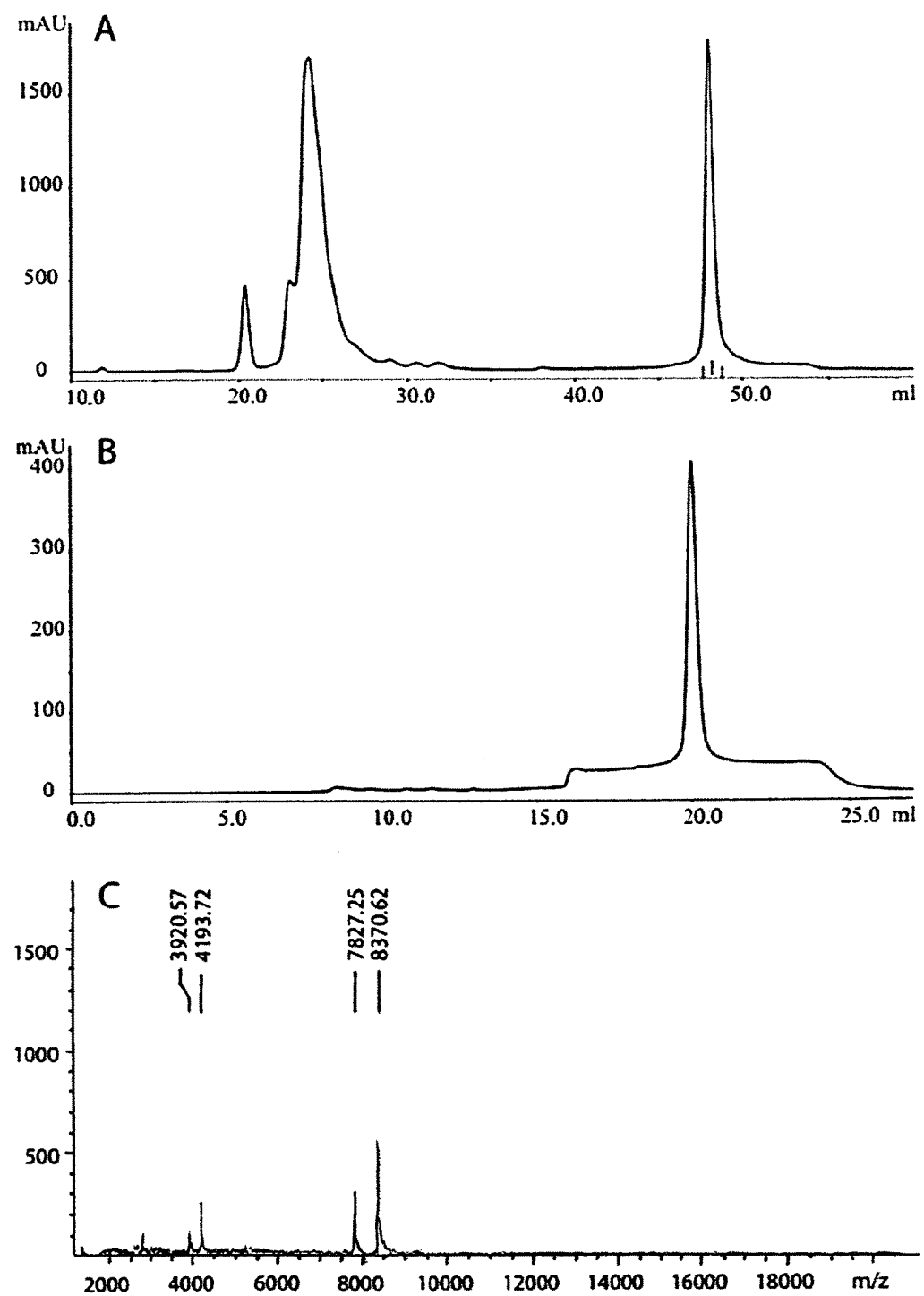

Subsequently, the amino-modified triphosphate (i.e. compound 3, FIG. 16) was treated with a premixed solution of cholesteryl chloroformate (36 mg, 80 µmol), N,N-diisopropylethylamine (13.9 µl, 40 µmol) and 4-dimethylaminopyridine (4.9 mg, 40 µmol) in anhydrous dichloromethane (5 ml) for 15 min. The column was washed with anhydrous dichloromethane (3 ml) and anhydrous acetonitrile (6 ml) and dried in a stream of argon. For cleavage from the support and deprotection, the derivatized oligonucleotide was brought into contact with a freshly prepared solution of 40% aqueous methylamine and concentrated aqueous ammonia (AMA, 1:1, v/v, 2 ml) using two syringes. After 30 min cleavage time the solution was transferred to a screw cap vial, heated for 10 min at 65° C. and evaporated to dryness. The residue was dried by co-evaporation with absolute ethanol and treated with 1 M tetra-n-butylammonium fluoride in THF (1 ml, 1 mmol) with shaking for 16 h. After desalting on a NAP-25 column the fully deprotected cholesteryl-tagged triphosphate oligonucleotide was purified by HPLC using a reverse phase column (Hamilton PRP-1, 4.1×250 mm, FIG. 17A). Compound 4 eluted at 95% methanol concentration and the expected structure was confirmed by MALDI analysis (Mw 8370.6 Da, FIG. 17C).

Optionally, the cholesteryl-tag is removed by acid hydrolysis at pH 3.8 at 60° C. to obtain the corresponding triphosphate oligonucleotide (compound 5, FIG. 16) following the same procedure as described in example 3.

Example 5: The Systematic Introduction of 2'-O-methylations Results in a RIG-I Selective RNA Duplex A list of abbreviations and their meaning may be found at the end of the application text.

A body's own RNA is characterised by a plurality of modifications that may have an influence on RNA functions (tRNAs and rRNAs). 2'-O-methylations are thus able to modify the immunogenicity of the RNA. A selective RIG-I ligand should therefore not comprise more than one 2'-O-methylation per strand. These properties are included in the RNA duplex by combination of suitably methylated sense and antisense strands.

A screen of 2'-O-methylations resolved positions to introduce RIG-I selectivity (FIG. 5). For the sense (A) and antisense (B) strand of OH-GFP2 a full 2'-O-methylation screen was performed. Each position was modified individually by 2'-O-methylation and used for stimulation of RIG-I, TLR7 or TLR8. For stimulation of RIG-I, peripheral blood mononuclear cells (PBMCs) were blocked with Chloroquine and stimulated by lipofection of the duplex. IFNa was measured 20 h post stimulation by ELISA. For TLR7 and TLR8 only the relevant single-strand was screened for stimulatory capacity and checked on unblocked PBMCs. The single-strands were transfected by complexation with poly-L-Arginine and 20 h post transfection for TLR7 activation IFNa, for TLR8 activation IL12p70 was measured by ELISA. 100% induction with GFP2 for the sense strand corresponds to 3085 pg/ml IFNa for RIG-I, 2758 pg/ml IFNa for TLR7 and 1206 pg/ml IL12p70 for TLR8. For the antisense 100% of GFP2 corresponds to 2342 pg/ml IFNa for RIG-I, 1831 pg/ml IFNa for TLR7 and 3018 pg/ml IL12p70 for TLR8. An overview of the impact of position dependent introduction of 2'-O-methylation is given in table form (FIG. 5). Effects are normalized to the unmodified strand as a reference. White=no change, yellow=reduction of immune stimulation, red=no immune stimulation, green=augmented immune stimulation.

Furthermore, it could be shown that certain methylations render the duplex RIG-I specific and highly active.

FIG. 6: (A) Methylations inert for RIG-I activation were combined in the antisense strand and the resulting duplex was used for stimulation of chloroquine-blocked PBMCs at a concentration of 0.8 µg/ml. IFNa was measured by ELISA at 20 h post stimulation. 100% of OH-GFP2 resembles 2729 µg/ml IFNa. (B) Different combinations of 2'-O-methylations in sense and antisense strand were hybridized and used for stimulation of PBMCs. For the stimulation of RIG-I they were blocked with Chloroquine and transfected with Lipofectamine, for TLR7 and TLR8 unblocked PBMCs were used and transfected with duplexes complexed with poly-L-Arginine. 100% for IVT-2 correspond to 4861 pg/ml IFNa for RIG-I 100% at 9.2 S correspond to 1975 pg/ml IFNa for TLR7 and 771 pg/ml IL12p70 for TLR8. (A) and (B) show mean±SEM of 3 donors.

Example 6: Increase of RIG-I Activation by Insertion of RNA-Stabilising Modifications During siRNA therapy short dsRNA fragments are inserted in a body, where they inhibit the formation of a specific protein in the target cells. The problem with this form of therapy is the enormous instability of the siRNA duplexes. RNA may easily be degraded by exonucleases and endonucleases in the serum during transport to the target cell.

It seems probable that a significant part of exogenous RNA used for therapeutic purposes is degenerated in serum and cytosol of the subject to which it is administered.

It could be shown that each 5'-PTO modification has a positive effect on duplex immune activity and that the combination of 5'PTO in the sense and antisense strand leads to a maximum increase in activity (s15/as3 against s15 PTO/as3 PTO; FIG. 7 B). The use such modifications of the RNA backbone in RIG-I selective ligands can thus be regarded as beneficial.

In particular, it could be shown that 5'-phosphorothioates augment immunogenicity of a selective duplex.

FIG. 7: (A) PBMCs were blocked with Chloroquine and stimulated with duplexes at a concentration of 0.8 µg/ml. 20 h post stimulation IFNa was measured by ELISA. 100% of IVT2 corresponds to 6138 pg/ml IFNa. (B) Indicated duplexes were titrated and used for stimulation of RIG-I. PBMCs were blocked with Chloroquine and duplexes were transfected using Lipofectamine. 20 h post stimulation IFNa was determined in the supernatant by ELISA. 100% of 50 nM 3P-GFP2 corresponds to 16044 pg/ml IFNa. Results show mean±SEM of 4 donors.

In the development on therapeutic siRNAs the problem of serum stability was solved by another kind of modification: if the 2'-fluoro substitutions were incorporated in the RNA, the resulting RNAs were more stable with regard to nuclease digestion. However, it was observed that in case of RIG-I dependent immune stimulation a 2'-fluoro substitution could activate immune stimulation.

In particular, it could be shown that 5'-phosphorothioates augment immunogenicity of a selective duplex.

However, according to the present invention it was found that selected 2'-fluoro substitutions augment the RIG-I activation potential of the duplex.

Figure 8:
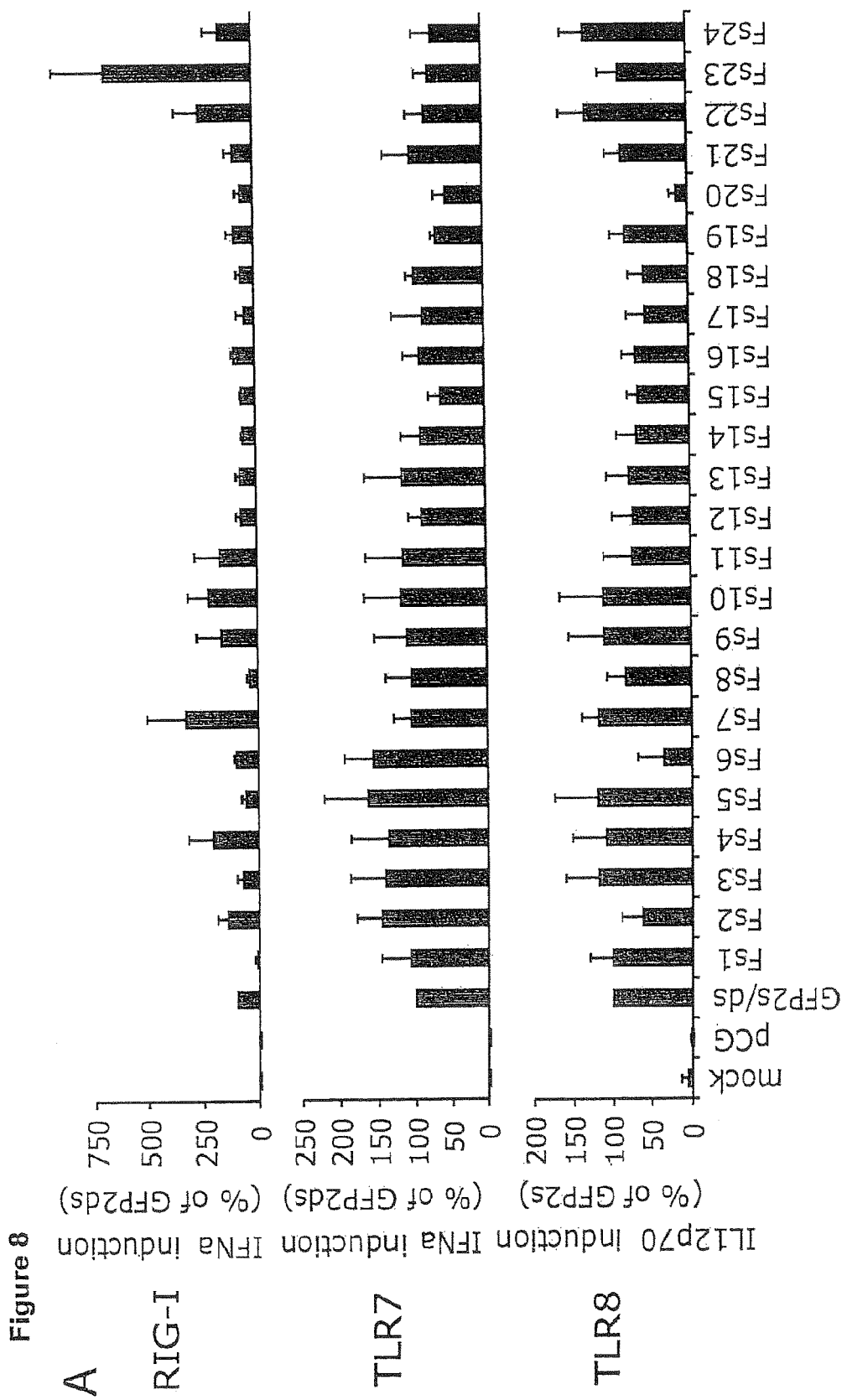

For the sense (A) and antisense (B) strand of the duplex each position was modified by a 2'-Fluoro-substitution individually (FIG. 8). Resulting duplexes were used for stimulation of PBMCs at a concentration of 0.8 µg/ml. For the assessment of RIG-I activation PBMCs were blocked and transfected by Lipofectamine, for stimulation of TLR7 and TLR8 PBMCs were used unblocked and transfected with duplexes complexed with poly-L-Arginine. 20 h post stimulation cytokines was measured by ELISA. 100% for GFP2 in the sense strand resembles 2407 pg/ml IFNa for RIG-I, 3281 pg/ml fir TLR7 and 1990 pg/ml for TLR8. For the antisense strand 100% GFP2 corresponds to 4512 pg/ml IFNa for RIG-I, 4691 pg/ml IFNa for TLR7 and 1997 pg/ml IL12p70 for TLR8. Shown is mean±SEM of 4 donors.

Thus, it was very important to establish a duplex as active as possible which can compensate the loss of RNA by its strong activity. In the previous passage it was described how RNA modifications could be identified by selective PTO bindings and 2'-fluoro substitutions, which led to an increase in the activity of a duplex.

Example 7: The Combination of all Modifications Leads to a Strongly Immunogenic RIG-I Ligand In order to test if PTO bindings or 2'-fluoro substitutions can be combined with 2'-O-methylations to increase selectivity, they were combined in a duplex step-by-step.

Figure 9:
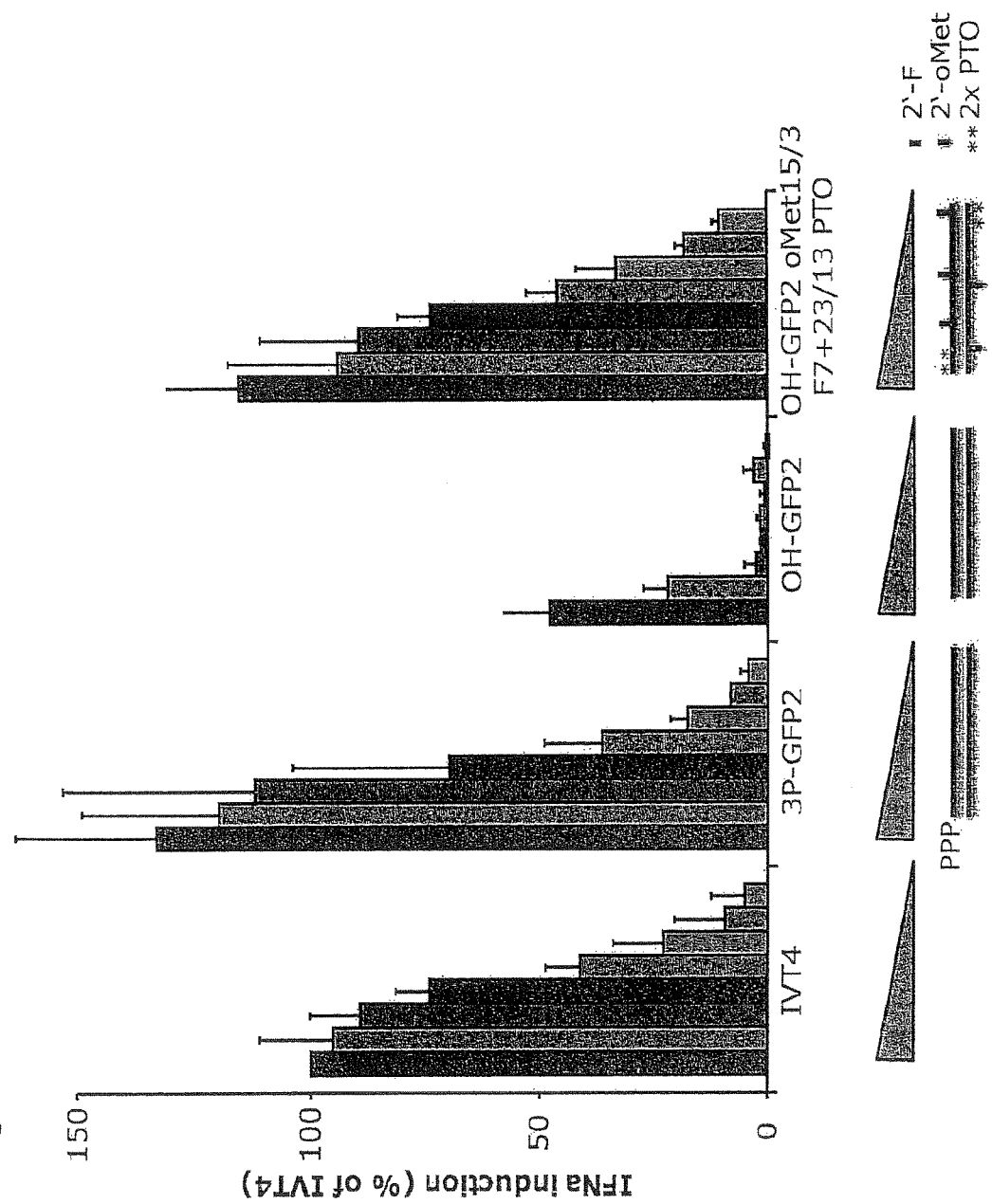
Figure 9:
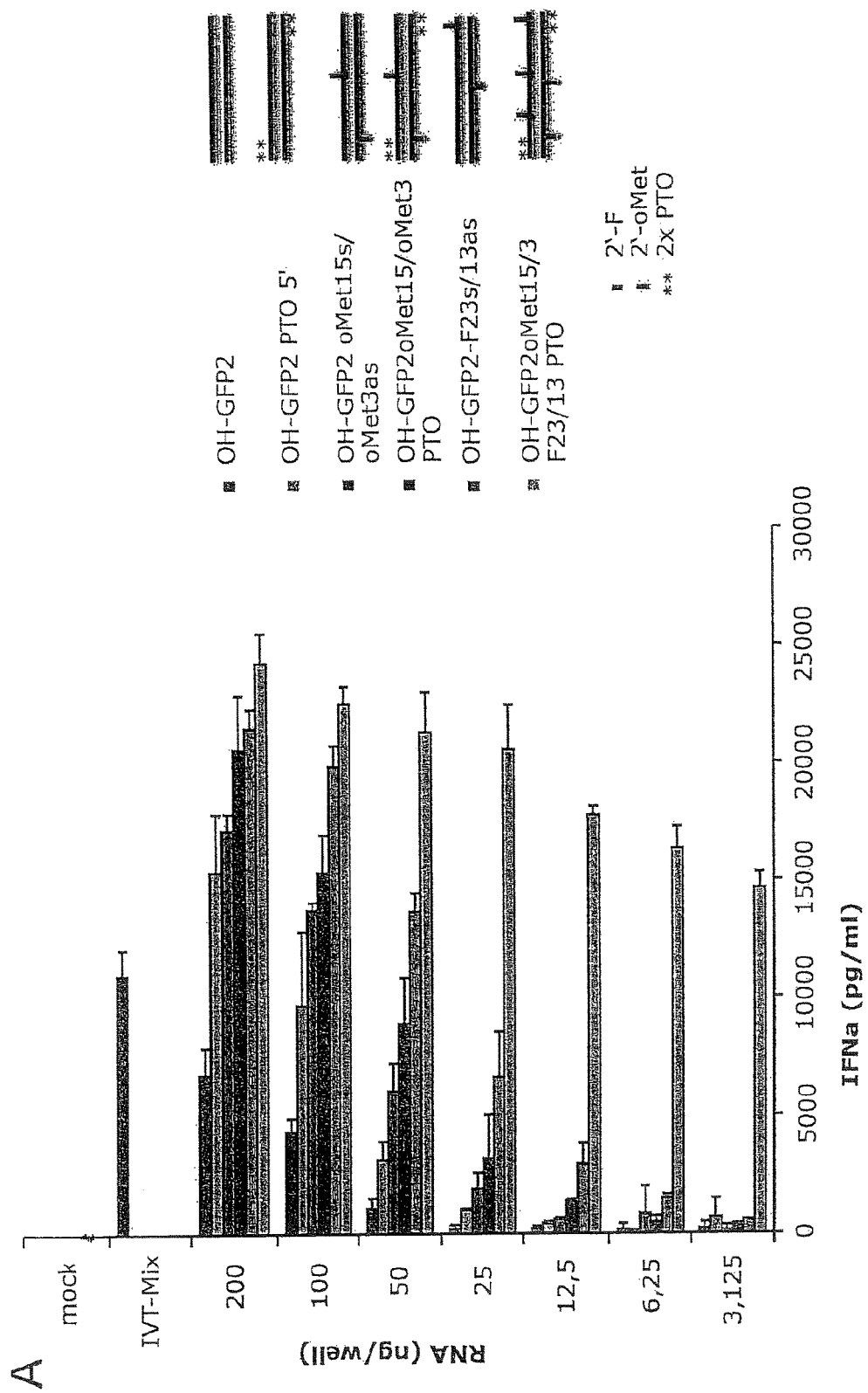

PBMCs were blocked with Chloroquine and used for stimulation of RIG-I. Differentially modified duplexes based on OH-GFP2 were used and RIG-I activation was measured at 20 h post stimulation by ELISA on IFNa (FIG. 9). Multiply modified duplexes were either compared to OH-GFP2 (A) or triphosphorylated 3P-GFP2 (B). 100% of IVT 4 corresponds to 21305 pg/ml of INFa. Shown is mean±SEM of 2 donors.

The 2'-O methylations s15/as3 were added to the starting RNA OH-GFP2 first (OH-GFP2 oMet15s/oMet3as, FIG. 9 A) and then compared to the 5'-PTO modification in sense and antisense (OH-GFP2 PTO 5', FIG. 9 A). Subsequently, both types of modification were combined with a duplex (OH-GFP2oMet15/oMet3 PTO, FIG. 9 A). Finally, a duplex was generated that additionally comprised three 2'-fluoro substitutions at positions 7 & 23 in sense and at position 13 in antisense (OH-GFP2oMet15/3-F23/13-PTO, FIG. 9 A). The comparative titration of these RNA double-strands showed that the multi-modified oligo OH-GFP2oMet15/3-F23/13-PTO surpassed other duplexes in activity by far. To better evaluate its activity, the duplex was titred and compared to its unmodified triphosphate duplex (FIG. 9 B). It was found that the insertion of a modification made it possible to change the oligonucleotide so that its immune activity compared to that of its triphosphate equivalent (3P-GFP2, FIG. 9 B).

Example 8: The Elements are Transferable to the 3P-dsRNA System

The whole development of the RIG-I selective ligand was carried out on the OH level of the sequence GFP2. Although the activity could be increased immensely by suitable modifications, a triphosphorylation of a ligand would increase its activity additionally.

So far it was not clear whether the modifications and their respective positioning could just be transferred to the 3P-GFP2 system.

Figure 10:
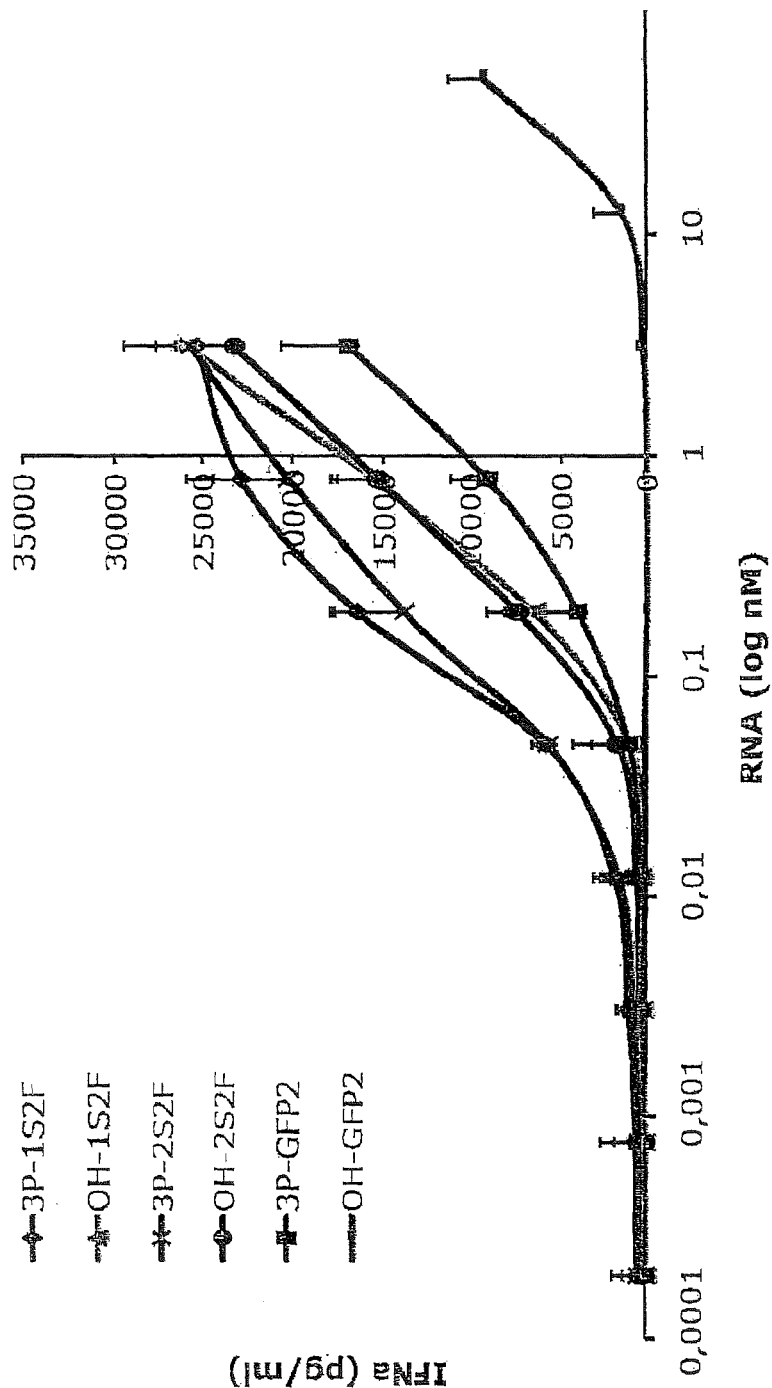
Figure 10:
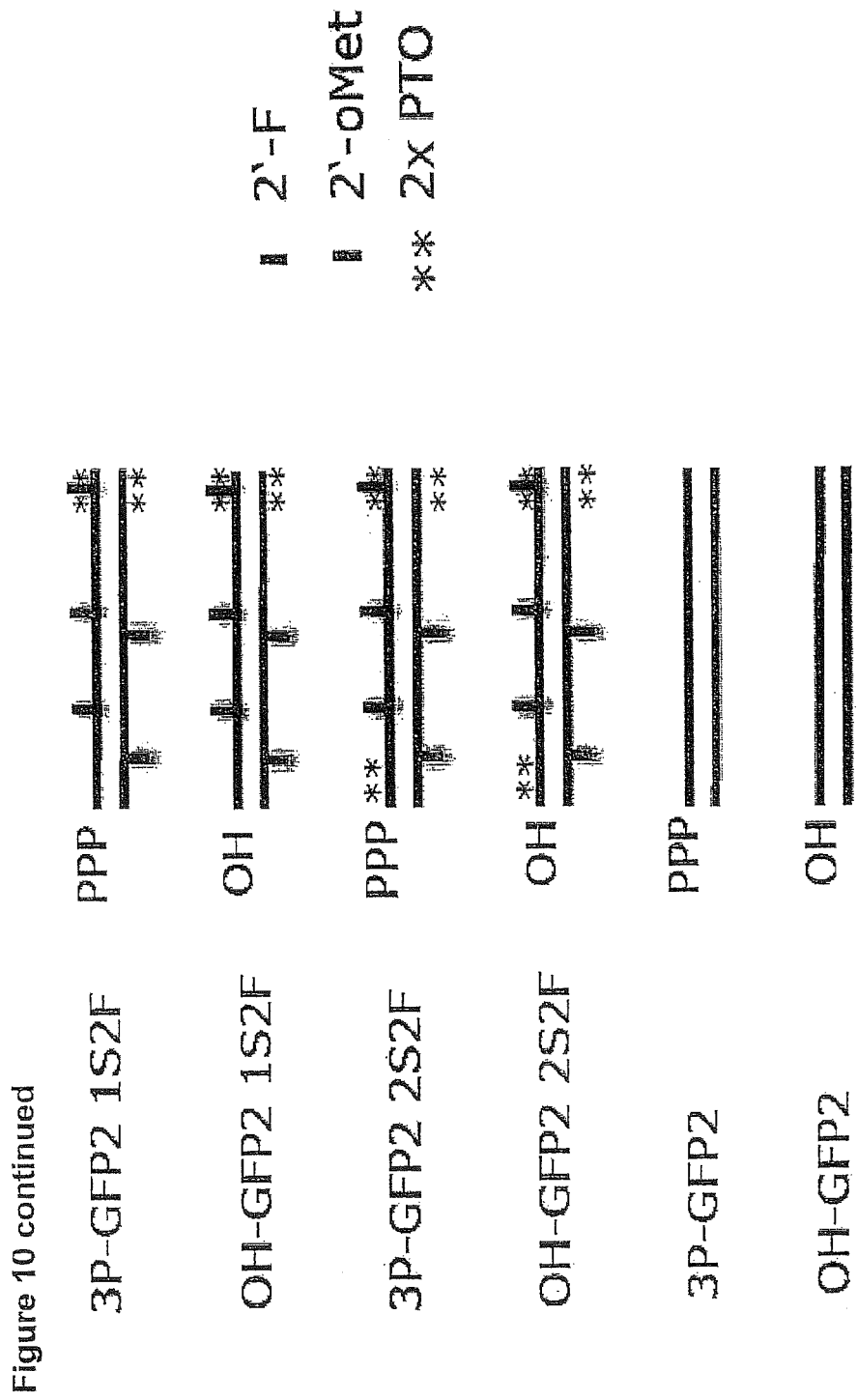
Figure 10:
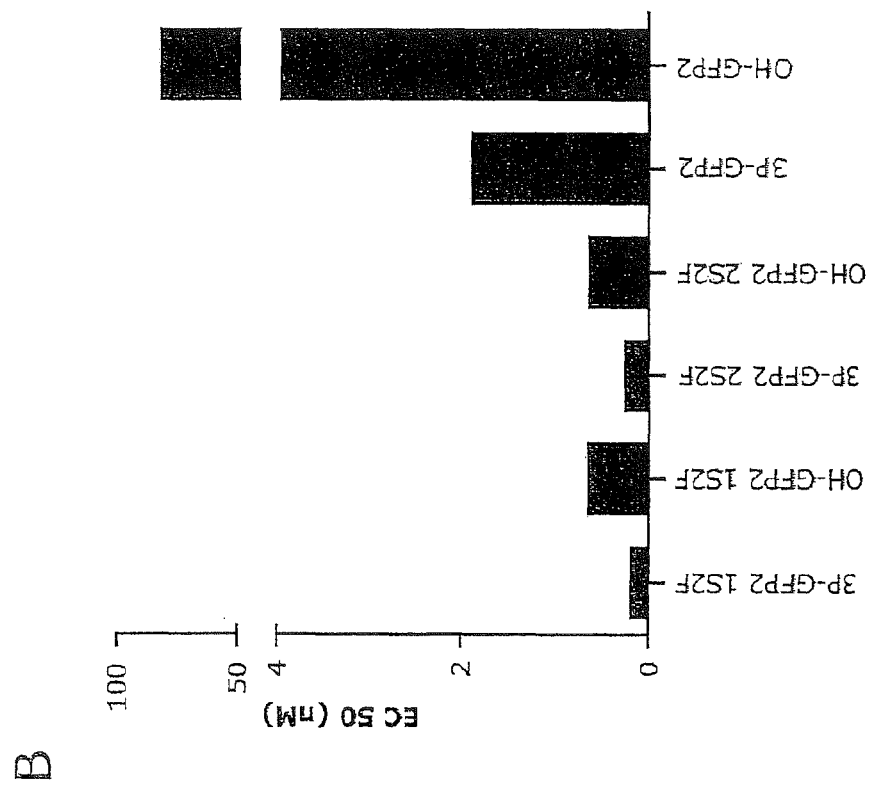

In order to find an answer to this question duplexes were produced, which all had the modification that increased the activity: 2'-O methylation at base 15 in the sense strand, 2'-fluoro substitution at base 7 and 23 and two PTO bindings at the 5' and the 3' end (2S2F, FIG. 10). In the antisense strand a 2'-O methylation at base 3, a 2'-fluoro substitution at base 13 and two 5'-PTO binding were combined. To avoid that the two 5'-PTO bindings at the sense strand intermit by their proximity to the triphosphate, a multi-modified sense strand without 5'-PTOs was produced additionally (1S2F, FIG. 10).

In order to be able to estimate the gain in activity by triphosphorylation, the duplexes were each produced with 5'-hydroxyl and 5'-triphosphate (OH vs 3P, FIG. 10) and compared to each other by stimulation titration on PBMCs.

FIG. 10: (A) Multimodified duplexes were synthesized with and without triphosphate. A dose titration was performed on Chloroquine blocked PBMCs. 20 h post stimulation immune activation was measured by ELISA on IFNa. Shown is mean±SEM of 4 donors. (B) Based on the titration curves the biological EC50 values were calculated.

It was found that the multi-modified OH duplexes, irrespective of the presence of one or two PTO ends, could reach the activity limits of the unmodified form of OH-GFP2 (OH Multi 1S2F, OH Multi 2S2F, OH-GFP2, FIG. 10). The additional addition of 5'-triphosphate at the sense strand resulted in an additional increase in activity by factor 5 compared to the hydroxyl complexes (3P-Multi 1S2F, 3P-Multi 2S2F, FIG. 10).

As a result it was observed that the activity-increasing effects of various modifications can be combined with the triphosphorylation of the oligonucleotide and that they also show their positive influence there.

By the progressive increase of the original duplex OH-GFP2 on the level of selectivity (2'-O methylation), the increase in activity by stabilising modifications (PTO bindings and 2'-fluoro substitutions) and the affinity to the binding pocket (triphosphate), it became possible to define a potent, selective RIG-I ligand (3P-Multi 1S2F).

Finally, a 3P-dsRNA could be developed in which the immune-stimulating activity was increased to a maximum by the specific insertion of modifications. This increase in immunogenicity makes it possible to keep the dosage of a medicament on a low level, and to compensate losses in RNA that occur in the period from the application of a medicament until the entry into a cell.

RNA Oligonucleotides

| Name | Sequence (above 5'-3', below 3'-5') | Internal modifications |
|---|---|---|
| GFP2s oMet1 | $G_m$ACGCUGACCCUGAAGUUCAUCUU (SEQ ID NO: 4)<br>C UGCGACUGGGACUUCAAGUAGAA (SEQ ID NO: 5) | $N_m$ = 2'-OCH$_3$ |
| GFP2s oMet2 | GA$_m$CGCUGACCCUGAAGUUCAUCUU (SEQ ID NO: 6)<br>CU GCGACUGGGACUUCAAGUAGAA (SEQ ID NO: 7) | |
| GFP2s oMet23 | GACGCUGACCCUGAAGUUCAUCU$_m$U (SEQ ID NO: 8)<br>CUGCGACUGGGACUUCAAGUAGA A (SEQ ID NO: 9) | |
| GFP2s oMet24 | GACGCUGACCCUGAAGUUCAUCUU$_m$ (SEQ ID NO: 10)<br>CUGCGACUGGGACUUCAAGUAGAA (SEQ ID NO: 11) | |
| GFP2as oMet1 | G ACGCUGACCCUGAAGUUCAUCUU (SEQ ID NO: 12)<br>C$_m$UGCGACUGGGACUUCAAGUAGAA (SEQ ID NO: 13) | $N_m$ = 2'-OCH$_3$ |
| GFP2as oMet2 | GA CGCUGACCCUGAAGUUCAUCUU (SEQ ID NO: 14)<br>CU$_m$GCGACUGGGACUUCAAGUAGAA (SEQ ID NO: 15) | |
| GFP2as oMet23 | GACGCUGACCCUGAAGUUCAUCU U (SEQ ID NO: 16)<br>CUGCGACUGGGACUUCAAGUAGA$_m$A (SEQ ID NO: 17) | |
| GFP2as oMet24 | GACGCUGACCCUGAAGUUCAUCUU (SEQ ID NO: 18)<br>CUGCGACUGGGACUUCAAGUAGAA$_m$ (SEQ ID NO: 19) | |
| OH-GFP2 multi oMet | GACGCUGACCCUGAAGUUCAUCUU (SEQ ID NO: 20)<br>CUGCGACUGGGACUUCAAGUAGAA (SEQ ID NO: 21) | $N_m$ = 2'-OCH$_3$ |
| s20/as12 | GACGCUGACCCU GAAGUUCA$_m$UCUU (SEQ ID NO: 22)<br>CUGCGACUGGGA$_m$CUUCAAGU AGAA (SEQ ID NO: 23) | $N_m$ = 2'-OCH$_3$ |
| s20/as19 | GACGCUGACCCUGAAGUUC A$_m$UCUU (SEQ ID NO: 24)<br>CUGCGACUGGGACUUCAAG$_m$U AGAA (SEQ ID NO: 25) | $N_m$ = 2'-OCH$_3$ |
| s15/as12 | AGCGCUGACCCU GAA$_m$GUUCAUCUU (SEQ ID NO: 26)<br>CUGCGACUGGGA$_m$CUU CAAGUAGAA (SEQ ID NO: 27) | $N_m$ = 2'-OCH$_3$ |
| s15/as19 | GACGCUGACCCUGAA$_m$GUUC AUCUU (SEQ ID NO: 28)<br>CUGCGACUGGGACUU CAAG$_m$UAGAA (SEQ ID NO: 29) | $N_m$ = 2'-OCH$_3$ |
| s20/as3 | GAC GCUGACCCUGAAGUUCA$_m$UCUU (SEQ ID NO: 30)<br>CUG$_m$CGACUGGGACUUCAAGU AGAA (SEQ ID NO: 31) | $N_m$ = 2'-OCH$_3$ |

-continued

| Name | Sequence (above 5'-3', below 3'-5') | Internal modifications |
|---|---|---|
| s15/as3 | GAC GCUGACCCUGAA$_m$GUUCAUCUU (SEQ ID NO: 32)<br>CUG$_m$CGACUGGGACUU CAAGUAGAA (SEQ ID NO: 33) | N$_m$ = 2'-OCH$_3$ |
| s3/as12 | GAC$_m$GCUGACCCU GAAGUUCAUCUU (SEQ ID NO: 34)<br>CUG CGACUGGGA$_m$CUUCAAGUAGAA (SEQ ID NO: 35) | N$_m$ = 2'-OCH$_3$ |
| s3/as19 | GAC$_m$GCUGACCCUGAAGUUC AUCUU (SEQ ID NO: 36)<br>CUG CGACUGGGACUUCAAG$_m$UAGAA (SEQ ID NO: 37) | N$_m$ = 2'-OCH$_3$ |
| Fs1 | G$_F$ACGCUGACCCUGAAGUUCAUCUU (SEQ ID NO: 38)<br>C UGCGACUGGGACUUCAAGUAGAA (SEQ ID NO: 39) | N$_F$ = 2'-F |
| Fs2 | GA$_F$CGCUGACCCUGAAGUUCAUCUU (SEQ ID NO: 40)<br>CU GCGACUGGGACUUCAAGUAGAA (SEQ ID NO: 41) | |
| Fs23 | GACGCUGACCCUGAAGUUCAUCU$_F$U (SEQ ID NO: 42)<br>CUGCGACUGGGACUUCAAGUAGA A (SEQ ID NO: 43) | |
| Fs24 | GACGCUGACCCUGAAGUUCAUCUU$_F$ (SEQ ID NO: 44)<br>CUGCGACUGGGACUUCAAGUAGAA (SEQ ID NO: 45) | |
| Fas1 | G ACGCUGACCCUGAAGUUCAUCUU (SEQ ID NO: 46)<br>C$_F$UGCGACUGGGACUUCAAGUAGAA (SEQ ID NO: 47) | N$_F$ = 2'-F |
| Fas2 | GA CGCUGACCCUGAAGUUCAUCUU (SEQ ID NO: 48)<br>CU$_F$GCGACUGGGACUUCAAGUAGAA (SEQ ID NO: 49) | |
| Fas23 | GACGCUGACCCUGAAGUUCAUCU U (SEQ ID NO: 50)<br>CUGCGACUGGGACUUCAAGUAGA$_F$A (SEQ ID NO: 51) | |
| Fas24 | GACGCUGACCCUGAAGUUCAUCUU (SEQ ID NO: 52)<br>CUGCGACUGGGACUUCAAGUAGAA$_F$ (SEQ ID NO: 53) | |
| 3P-GFP2 | ppp-GACGCUGACCCUGAAGUUCAUCUU (SEQ ID NO: 54)<br>CUGCGACUGGGACUUCAAGUAGAA (SEQ ID NO: 55) | |
| s15/as3 PTO | GAC GCUGACCCUGAA$_m$GUUCAUC U U (SEQ ID NO: 56)<br>CUG$_m$CGACUGGGACUU CAAGUAG*A*A (SEQ ID NO: 57) | * = PTO<br>N$_m$ = 2'-OCH$_3$ |
| s15 PTO/as3 | G*A*C GCUGACCCUGAA$_m$GUUCAUCUU (SEQ ID NO: 58)<br>C U G$_m$CGACUGGGACUU CAAGUAGAA (SEQ ID NO: 59) | * = PTO<br>N$_m$ = 2'-OCH$_3$ |
| s15 PTO/as3 PTO | G*A*C GCUGACCCUGAA$_m$GUUCAUC U U (SEQ ID NO: 60)<br>C U G$_m$CGACUGGGACUU CAAGUAG*A*A (SEQ ID NO: 61) | * = PTO<br>N$_m$ = 2'-OCH$_3$ |
| OH-GFP2 PTO 5' | G*A*CGCUGACCCUGAAGUUCAUC U U (SEQ ID NO: 62)<br>C U GCGACUGGGACUUCAAGUAG*A*A (SEQ ID NO: 63) | * = PTO |
| OH-GFP2 oMet15/oMet3 PTO | G*A*C GCUGACCCUGAA$_m$GUUCAUC U U (SEQ ID NO: 64)<br>C U G$_m$CGACUGGGACUU CAAGUAG*A*A (SEQ ID NO: 65) | * = PTO<br>N$_m$ = 2'-OCH$_3$ |
| OH-GFP2 F23s/13as | GACGCUGACCCUG AAGUUCAUCU$_F$U (SEQ ID NO: 66)<br>CUGCGACUGGGAC$_F$UUCAAGUAGA A (SEQ ID NO: 67) | N$_F$ = 2'-F |
| OH-GFP2 oMet15/3 F23/13 PTO | G*A*C GCUG$_F$ACCCUG AA$_m$GUUCAUC U$_F$ U (SEQ ID NO: 68)<br>C U G$_m$CGAC UGGGAC$_F$UU CAAGUAG*A *A (SEQ ID NO: 69) | N$_F$ = 2'-F<br>* = PTO<br>N$_m$ = 2'-OCH$_3$ |
| 3P-GFP2 1S2F | PPP-GAC GCUG$_F$ACCCUG AA$_m$GUUCAUC*U$_F$*U (SEQ ID NO: 70)<br>CUG$_m$CGAC UGGGAC$_F$UU CAAGUAG*A *A (SEQ ID NO: 71) | N$_F$ = 2'-F<br>* = PTO<br>N$_m$ = 2'-OCH$_3$ |
| OH-GFP2 1S2F | GAC GCUG$_F$ACCCUG AA$_m$GUUCAUC*U$_F$*U (SEQ ID NO: 72)<br>CUG$_m$CGAC UGGGAC$_F$UU CAAGUAG*A *A (SEQ ID NO: 73) | N$_F$ = 2'-F<br>* = PTO<br>N$_m$ = 2'-OCH$_3$ |
| 3P-GFP2 2S2F | PPP-G*A*C GCUG$_F$ACCCUG AA$_m$GUUCAUC*U$_F$*U<br>(SEQ ID NO: 74)<br>C U G$_m$CGAC UGGGAC$_F$UU CAAGUAG*A *A (SEQ ID NO: 75) | N$_F$ = 2'-F<br>* = PTO<br>N$_m$ = 2'-OCH$_3$ |
| OH-GFP2 2S2F | G*A*C GCUG$_F$ACCCUG AA$_m$GUUCAUC*U$_F$*U (SEQ ID NO: 76)<br>C U G$_m$CGAC UGGGAC$_F$UU CAAGUAG*A *A (SEQ ID NO: 77) | N$_F$ = 2'-F<br>* = PTO<br>N$_m$ = 2'-OCH$_3$ |

The invention claimed is:

1. An oligonucleotide comprising a sense strand and an antisense strand, wherein the oligonucleotide comprises
  a sense strand comprising nucleotide sequence
    5' GACGCUG$_f$ACCCUGAA$_m$GUUCAUC$_{PTO}$U$_{fPTO}$U 3' (SEQ ID NO: 72); and
  an antisense strand comprising nucleotide sequence
    3' CUG$_m$CGACUGGGAC$_f$UUCAAGUAG$_{PTO}$A$_{PTO}$A 5' (SEQ ID NO: 73); or
  a sense strand comprising nucleotide sequence
    5' G$_{PTO}$A$_{PTO}$CGCUG$_f$ACCCUGAA$_m$GUUCAUC$_{PTO}$U$_{fPTO}$U 3' (SEQ ID NO: 76); and
  an antisense strand comprising nucleotide sequence
    3' CUG$_m$CGACUGGGAC$_f$UUCAAGUAG$_{PTO}$A$_{PTO}$A 5' (SEQ ID NO: 77);
  wherein
    the nucleotide indexed m is 2'-O-methylated;
    the nucleotide indexed f is 2'-fluoro; and
    the index PTO between two nucleotides indicates that said two nucleotides are linked by a phosphorothioate bond; and
  wherein the sense strand has a triphosphate at the 5' end.

2. The oligonucleotide of claim 1, wherein the oligonucleotide is a RIG-I ligand.

3. A pharmaceutical composition comprising an oligonucleotide according to claim 1 and a pharmaceutically acceptable carrier, diluent and/or adjuvant.

4. The pharmaceutical composition of claim 3, wherein the pharmaceutically acceptable carrier, diluent and/or adjuvant is suitable for intraperitoneal, intramuscular, intravenous, intranasal, subcutaneous, intradermal or intrathecal administration.

5. The pharmaceutical composition of claim 4, wherein the pharmaceutically acceptable carrier, diluent and/or adjuvant is suitable for intradermal administration by tattooing, microneedling or microneedle patches.

6. A method for stimulating a patient's immune system, comprising administering an oligonucleotide comprising a sense strand and an antisense strand to a patient in need of such stimulation, wherein
  the sense strand comprises a nucleotide sequence of
    5' GACGCUGACCCUGAAGUUCAUCUU 3' (SEQ ID NO: 2); and
  the antisense strand comprises a nucleotide sequence of
    3' CUGCGACUGGGACUUCAAGUAGAA 5'(SEQ ID NO: 5); and
  the oligonucleotide further comprises at least one triphosphate at one 5' end of the oligonucleotide and at least one modification selected from the group consisting of 2'-O-methyl, 2'-fluoro and phosphorothioate bond
  wherein the modification is 2'-O-methyl and the sense strand and/or the antisense strand comprises at least one 2'-O-methylated ribonucleotide, wherein the nucleotide is nucleotide 3, 10, 13, 15, 16, 17, 20, or 23, or any combination thereof, of the sense strand, and/or the 2'-O-methylated ribonucleotide is the nucleotide at position 3, 18, 19, 21, 22 or 23, or any combination thereof, of the antisense strand; wherein the nucleotide position is counted from left to right for both the sense strand and antisense strand, and wherein the oligonucleotide further comprises at least one modification selected from 2'-fluoro and a phosphorothioate bond.

7. The method according to claim 6, wherein said oligonucleotide selectively stimulates the RIG-I signalling pathway.

8. The method according to claim 6, wherein said oligonucleotide is administered intraperitoneally, intramuscularly, intravenously, intranasally, subcutaneously, intradermally or intrathecally.

9. The method according to claim 8, wherein said modified oligonucleotide is administered intradermally by tattooing, microneedling or microneedle patches.

10. A pharmaceutical composition comprising an oligonucleotide according to claim 2 and a pharmaceutically acceptable carrier, diluent and/or adjuvant.

11. An oligonucleotide comprising a sense strand and an antisense strand, wherein the oligonucleotide comprises
  a sense strand comprising nucleotide sequence
    5' GACGCUG$_f$ACCCUGAA$_m$GUUCAUC$_{PTO}$U$_{fPTO}$U 3' (SEQ ID NO: 72); and
  an antisense strand comprising nucleotide sequence
    3' CUG$_m$CGACUGGGAC$_f$UUCAAGUAG$_{PTO}$A$_{PTO}$A 5' (SEQ ID NO: 73); or
  wherein
    the nucleotide indexed m is 2'-O-methylated;
    the nucleotide indexed f is 2'-fluoro; and
    the index PTO between two nucleotides indicates that said two nucleotides are linked by a phosphorothioate bond; and
  wherein the sense strand has a triphosphate at the 5' end.

12. An oligonucleotide consisting of a sense strand and an antisense strand, wherein the oligonucleotide consists of
  a sense strand consisting of nucleotide sequence
    5' GACGCUG$_f$ACCCUGAA$_m$GUUCAUC$_{PTO}$U$_{fPTO}$U 3' (SEQ ID NO: 72); and
  an antisense strand consisting of nucleotide sequence
    3' CUG$_m$CGACUGGGAC$_f$UUCAAGUAG$_{PTO}$A$_{PTO}$A 5' (SEQ ID NO: 73);
  wherein
    the nucleotide indexed m is 2'-O-methylated;
    the nucleotide indexed f is 2'-fluoro; and
    the index PTO between two nucleotides indicates that said two nucleotides are linked by a phosphorothioate bond; and
  wherein the sense strand has a triphosphate at the 5' end.

13. A pharmaceutical composition comprising an oligonucleotide according to claim 12 and a pharmaceutically acceptable carrier or diluent.

14. A method for stimulating a patient's immune system, comprising administering an oligonucleotide according to claim 12 to a patient in need of such treatment.

15. A pharmaceutical composition comprising an oligonucleotide according to claim 12 and a pharmaceutically acceptable carrier and/or adjuvant.

16. A pharmaceutical composition comprising an oligonucleotide according to claim 12 and a pharmaceutically acceptable carrier, wherein said carrier comprises a sodium counterion.

17. A pharmaceutical composition comprising an oligonucleotide according to claim 12 and a sodium counterion.

* * * * *